US012577242B2

(12) United States Patent
Kiss et al.

(10) Patent No.: US 12,577,242 B2
(45) Date of Patent: Mar. 17, 2026

(54) PYRROLOPYRIDINE AND IMIDAZOPYRIDINE ANTIVIRAL COMPOUNDS

(71) Applicant: KATHOLIEKE UNIVERSITEIT LEUVEN, Leuven (BE)

(72) Inventors: Eleonora Kiss, Heverlee (BE); Robert Vrancken, Berchem (BE); Nesya Goris, Schoten (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 654 days.

(21) Appl. No.: 17/793,498

(22) PCT Filed: Feb. 24, 2021

(86) PCT No.: PCT/EP2021/054486
§ 371 (c)(1),
(2) Date: Jul. 18, 2022

(87) PCT Pub. No.: WO2021/170600
PCT Pub. Date: Sep. 2, 2021

(65) Prior Publication Data

US 2023/0130598 A1 Apr. 27, 2023

(30) Foreign Application Priority Data

Feb. 24, 2020 (EP) .................................... 20158958

(51) Int. Cl.
*C07D 471/04* (2006.01)
*A61P 31/14* (2006.01)

(52) U.S. Cl.
CPC ............ *C07D 471/04* (2013.01); *A61P 31/14* (2018.01)

(58) Field of Classification Search
CPC .................................................. C07D 471/04
USPC .......................................................... 514/300
See application file for complete search history.

(56) References Cited

U.S. PATENT DOCUMENTS

| | | | | |
|---|---|---|---|---|
| 7,648,998 B2 * | 1/2010 | Bondy | A61P 43/00 546/118 |
| 2005/0239821 A1 | 10/2005 | Neyts et al. | |
| 2008/0207678 A1 | 8/2008 | Bondy et al. | |
| 2010/0028301 A1 | 2/2010 | Bondy et al. | |

FOREIGN PATENT DOCUMENTS

| | | | |
|---|---|---|---|
| CN | 110229150 | * | 9/2019 |
| JP | 2005537248 | A | 12/2005 |
| JP | 2007518720 | A | 7/2007 |
| JP | 2010513286 | A | 4/2010 |
| WO | 2004005286 | A2 | 1/2004 |
| WO | 2005063744 | A2 | 7/2005 |
| WO | 2007034277 | A1 | 3/2007 |
| WO | 2008133669 | A2 | 11/2008 |

OTHER PUBLICATIONS

Liu et al., Bioorganic & Medicinal Chemistry (2018), 26(9), 2621-2631.*
Gerhard Puerstinge et al., "Substituted 5-benzyl-2-phenyl-5H-imidazo[4,5-c]pyridines: a new class of pestivirus Inhibitors," Bioorganic & Medicinal Chemistry Letters, vol. 16, No. 20, 2006, pp. 5345-5349, 0960-894X/S, doi: 10.1016/j.bmcl.2006.07.081, Elsevier Ltd.
PCT International Search Report dated May 7, 2021 in connection with PCT/EP2021/054486.
PCT Written Opinion of the International Searching Authority Report dated May 7, 2021 in connection with PCT/EP2021/0544868.
Japanese Office Action Dated Jan. 31, 2025 With Respect to Counterpart Japanese Patent Application No. 2022-550843, and Its English Translation 12 pages.
Puerstinger, Gerhard et al., Substituted 5-benzyl-2-phenyl-5H-imidazo[4,5-c]pyridines: A new class of pestivirus inhibitors, Bioorganic & Medicinal Chemistry Letters, 2006, 16(20), 5345-5349, DOI: 10.1016/j.bmcl.2006.07.081.

* cited by examiner

*Primary Examiner* — Niloofar Rahmani
(74) *Attorney, Agent, or Firm* — Amster, Rothstein & Ebenstein LLP

(57) ABSTRACT

The present invention relates to a compound of formula (I) or a stereoisomer, or tautomer, (I) wherein $A^1$, $A^2$, $R^1$ and $R^2$, have the same meaning as that defined in the claims and the description. The present invention also relates to compositions, in particular pharmaceuticals, comprising such compounds, and to uses of such compounds and compositions for the prevention and/or treatment of an infection caused by pestivirus in an animal.

(I)

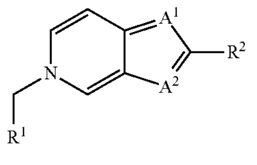

11 Claims, 3 Drawing Sheets

PYRROLOPYRIDINE AND IMIDAZOPYRIDINE ANTIVIRAL COMPOUNDS

CROSS-REFERENCE TO RELATED APPLICATIONS

This application is a U.S. national stage entry under 35 U.S.C. § 371 of PCT International Patent Application No. PCT/EP2021/054486, filed Feb. 24, 2021, which claims priority to European Patent Application No. 20158958.7, filed Feb. 24, 2020, the contents of each of which are incorporated herein by reference in their entirety.

FIELD OF THE INVENTION

The present invention relates to novel compounds and to the novel compounds for use as a medicine for the prevention or treatment of infection caused by pestivirus in an animal. The present invention further relates to methods for the preparation of said novel compounds.

BACKGROUND OF THE INVENTION

Pestivirus is a genus of viruses, in the family Flaviviridae. Viruses in the genus Pestivirus infect mammals, including members of the family Bovidae (which includes among others cattle, sheep, and goats) and the family Suidae (which includes various species of swine). Diseases associated with this genus include among others: bovine viral diarrhea, classical swine fever and border disease.

Bovine viral diarrhea (BVD), also known as bovine viral diarrhea-mucosal disease, is an acute infectious disease caused by bovine viral diarrhea virus (BVDV). BVDV infection results in a wide variety of clinical signs, in part due to its immunosuppressive effects, as well as having a direct effect on respiratory disease and fertility. In addition, BVDV infection of a susceptible dam during a certain period of gestation can result in the production of a persistently infected fetus and eventually to a persistently infected animal.

BVD is considered one of the most significant infectious diseases in the livestock industry worldwide due to its high prevalence, persistence and clinical consequences. In Europe the prevalence of antibody positive animals in countries without systematic BVD control is between 80 and 80%.

Transmission of BVDV occurs both horizontally and vertically with both persistently and acutely, transiently infected animals excreting infectious virus. Virus is transmitted via direct contact, bodily secretions and contaminated fomites, with the virus being able to persist in the environment for more than two weeks. Persistently infected animals are the most important source of the virus, continuously excreting a viral load about one thousand times that shed by acutely infected animals There are more than 140 vaccines against BVDV commercially available in the United States. Unfortunately, vaccination does not provide complete protection against BVDV infection, as some vaccinated cattle still become infected with the virus. At present, there is no known cure for BVDV infection. Moreover, persistently-infected animals cannot be protected via vaccination.

Thus there is a need in the art for an effective treatment and/or prevention of BVDV infections that is safe for use both in healthy and in persistently infected animals, that can be easily administered, and has a low cost.

SUMMARY OF THE INVENTION

The present invention is based on the unexpected finding that at least one of the above-mentioned objectives can be attained by novel compounds.

The present invention provides new compounds which have been shown to possess antiviral activity. The present invention furthermore demonstrates that these compounds efficiently inhibit proliferation of pestiviruses, and in particular bovine viral diarrhea virus (BVDV), classical swine fever virus, border disease virus, atypical porcine pestivirus or HoBi-like virus. Therefore, these compounds constitute a useful class of new potent compounds that can be used in the treatment and/or prevention of an infection caused by pestivirus in an animal; preferably a mammal; more preferably a bovine, a pig, a sheep, or a goat.

A first aspect of the present invention provides a compound of formula (I) or a stereoisomer, or tautomer thereof,

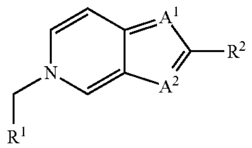

(I)

wherein, $A^1$ is N or CH;

$A^2$ is N or CH;

$R^1$ is selected from the group consisting of

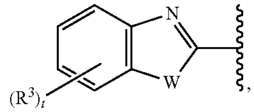,

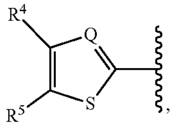,

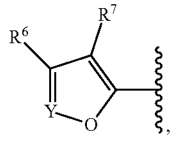,

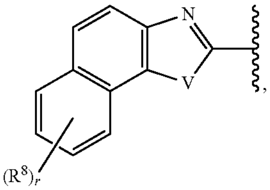, and

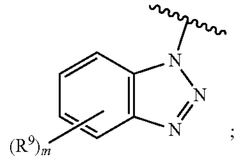;

wherein the wavy line () indicates the point of attachment to the methylene linker of the main formula (I);

t is an integer selected from 0; 1; 2; 3 and 4;

r is an integer selected from 0; 1; 2; 3 and 4;

m is an integer selected from 0; 1; 2; 3 and 4;

W is selected from the group consisting of $NR^{10}$, S or O;

Q is selected from the group consisting of $CR^{11}$ or N;

Y is selected from the group consisting of N or $CR^{12}$;

V is selected from the group consisting of $NR^{13}$, S or O;

$R^2$ is selected from the group consisting of aryl, pyrazolyl, pyridyl, thiophenyl; wherein said aryl, pyrazolyl, pyridyl, or thiophenyl; are optionally substituted with one or more $Z^1$;

each $R^3$ is independently selected from the group consisting of hydrogen, halo, trifluoromethyl, difluoromethyl, $C_{1-6}$alkoxy, trifluoromethoxy, difluoromethoxy, hydroxyl, $C_{1-5}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

$R^4$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^2$;

$R^5$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^3$;

$R^6$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^4$;

$R^7$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^5$;

each $R^8$ is independently selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

each $R^9$ is independently selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_2$, cyano, nitro, —COOH;

$R^{10}$ is selected from the group consisting of hydrogen, $C_{1-6}$alkyl, $C_{3-8}$cycloalkyl;

$R^{11}$ is selected from the group consisting of hydrogen, $C_{1-6}$alkyl, $C_{3-8}$cycloalkyl;

$R^{12}$ is selected from the group consisting of hydrogen, $C_{1-6}$alkyl, $C_{3-8}$cycloalkyl;

$R^{13}$ is selected from the group consisting of hydrogen, $C_{1-6}$alkyl, $C_{3-8}$cycloalkyl;

each $Z^1$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

each $Z^2$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH)_2$, —$O(CH_2)_2OH$, —$O(CH_2)_2OCH_3$, cyano, nitro, —COOH;

each $Z^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

each $Z^4$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

each $Z^5$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH; or a solvate, hydrate, salt or prodrug thereof.

In some embodiments, the present invention also comprises a compound of compound of formula (I) or a stereoisomer, or tautomer thereof, (I)

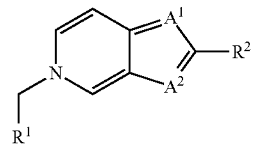

wherein, $A^1$ is N or CH;

$A^2$ is N or CH;

$R^1$ is selected from the group consisting of

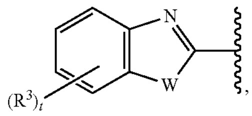

,

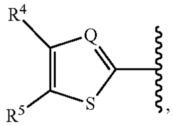

,

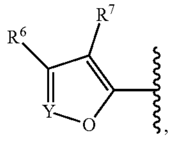

,

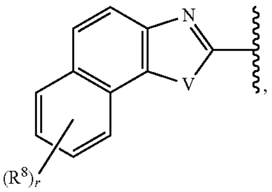

, and

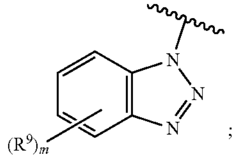

;

wherein the wavy line (〰) indicates the point of attachment to the methylene linker of the man formula (I);

t is an integer selected from 0; 1; 2; 3 and 4;

r is an integer selected from 0; 1; 2; 3 and 4;

m is an integer selected from 0; 1; 2; 3 and 4;

W is selected from the group consisting of $NR^{10}$, S or O;

Q is selected from the group consisting of $CR^{11}$ or N;

Y is selected from the group consisting of N or $CR^{12}$;

V is selected from the group consisting of $NR^{13}$, S or O;

$R^2$ is selected from the group consisting of aryl, pyrazolyl, pyridyl, thiophenyl; wherein said aryl, pyrazolyl, pyridyl, or thiophenyl; are substituted with one or more $Z^1$;

each $R^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

$R^4$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^2$;

$R^5$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^3$;

$R^6$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^4$;

$R^7$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^5$;

each $R^8$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

each $R^9$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

$R^{10}$ is selected from the group consisting of hydrogen, $C_{1-6}$alkyl, $C_{3-8}$cycloalkyl;

$R^{11}$ is selected from the group consisting of hydrogen, $C_{1-6}$alkyl, $C_{3-8}$cycloalkyl;

$R^{12}$ is selected from the group consisting of hydrogen, $C_{1-6}$alkyl, $C_{3-8}$cycloalkyl;

$R^{13}$ is selected from the group consisting of hydrogen, $C_{1-6}$alkyl, $C_{3-8}$cycloalkyl;

each $Z^1$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2{=}CH_3$, cyano, nitro, —COOH;

each $Z^2$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

each $Z^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

each $Z^4$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

each $Z^5$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH;

wherein when $R^1$ is

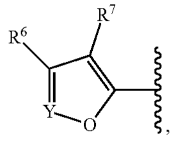

, and Y is N, then $R^2$ is not phenyl;

with the proviso that said compound is not:

2-(3-Fluoro-3',4'-dimethyl-biphenyl-4-yl)-5-(4-methyl-thiazol-2-ylmethyl)-5H-imidazo[4,5-c]pyridine;

or a solvate, hydrate, salt or prodrug thereof.

According to a second aspect, the present invention also encompasses a pharmaceutical composition comprising one or more pharmaceutically acceptable excipients and a therapeutically effective amount of a compound according to the first aspect of the invention.

According to a third aspect, the present invention also encompasses a compound according to the first aspect of the invention, or a pharmaceutical composition according to the second aspect of the invention, for use as a medicament.

According to a fourth aspect, the present invention also encompasses a compound according to the first aspect of the invention, or a pharmaceutical composition according to the second aspect of the invention, for use as a medicine for the prevention and/or treatment an infection caused by pestivirus in an animal; preferably a mammal; more preferably a bovine, a pig, a sheep, or a goat.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The independent and dependent claims set out particular and preferred features of the invention. Features from the dependent claims may be combined with features of the independent or other dependent claims as appropriate.

BRIEF DESCRIPTION OF THE FIGURES

The following description of the figures of specific embodiments of the invention is merely exemplary in nature and is not intended to limit the present teachings, their application or uses.

DETAILED DESCRIPTION OF THE INVENTION

Figure 1:
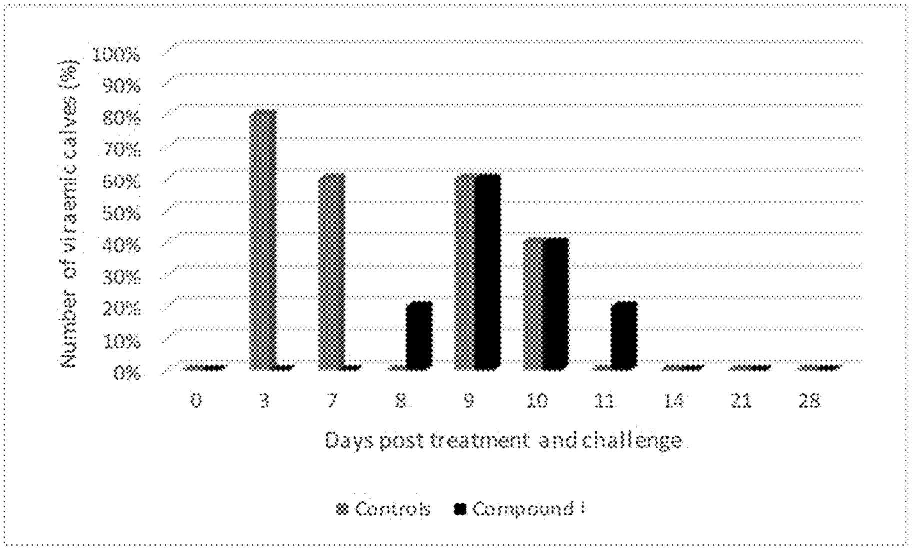
FIG. 1 represents a graph plotting the number of viremic calves (%) against days post treatment with Compound I (2 mg/kg bodyweight three times daily at 8 h intervals) and untreated controls following challenge with BVDV. The compound was administered for 7 consecutive days.

Before the present invention is described, it is to be understood that this invention is not limited to particular processes, methods, and compounds described, as such processes, methods, and compounds may, of course, vary. It is also to be understood that the terminology used herein is not intended to be limiting, since the scope of the present invention will be limited only by the appended claims.

When describing the compounds and processes of the invention, the terms used are to be construed in accordance with the following definitions, unless a context dictates otherwise.

As used in the specification and the appended claims, the singular forms “a”, “an,” and “the” include both singular and plural referents unless the context clearly dictates otherwise. By way of example, “a compound” means one compound or more than one compound.

The terms “comprising”, “comprises” and “comprised of” as used herein are synonymous with “including”, “includes” or “containing”, “contains”, and are inclusive or open-ended and do not exclude additional, non-recited members, elements or method steps. The terms “comprising”, “comprises” and “comprised of” also include the term “consisting of”.

The term “about” as used herein when referring to a measurable value such as a parameter, an amount, a temporal duration, and the Ike, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier “about” refers is itself also specifically, and preferably, disclosed.

As used herein, the term “and/or,” when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of end points also includes the end point values themselves (e.g. from 1.0 to 5.0 includes both 1.0 and 5.0). Any numerical range recited herein is intended to include all sub-ranges subsumed therein.

Reference throughout this specification to “one embodiment” or “an embodiment” means that a particular feature, structure or characteristic described in connection with the embodiment is included in at least one embodiment of the present invention. Thus, appearances of the phrases “in one embodiment” or “in an embodiment” in various places throughout this specification are not necessarily all referring to the same embodiments but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments combinations of features of different embodiments are meant to be within the scope of the invention, and form different embodiments as would be understood by those in the art. For example, in the following claims, any of the claimed embodiments can be used in any combination.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Men describing the present invention, the terms used are to be construed in accordance with the following definitions, unless a context dictates otherwise.

The terms described above and others used in the specification are well understood to those in the art.

Whenever the term “substituted” is used herein, it is meant to indicate that one or more hydrogen atoms on the atom indicated in the expression using “substituted” is replaced with a selection from the indicated group, provided that the indicated atom’s normal valence is not exceeded, and that the substitution results in a chemically stable compound, i.e. a compound that is sufficiently robust to survive isolation from a reaction mixture.

The term “halo” or “halogen” as a group or part of a group is generic for fluoro, chloro, bromo, iodo.

The term “hydroxyl” or “hydroxy” as used herein refers to the group —OH.

The term “cyano” as used herein refers to the group —C≡N.

The term “amino” as used herein refers to the $—NH_2$ group.

The term “nitro” as used herein refers to the $—NO_2$ group.

The term “$C_{1-6}$alkyl”, as a group or part of a group, refers to a hydrocarbyl group of formula $—C_nH_{2n+1}$ wherein n is a number ranging from 1 to 6. Alkyl groups may be linear or branched and may be substituted as indicated herein. Thus, for example, “$C_{1-6}$alkyl” includes all linear or branched alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers. For example, “$C_{1-5}$alkyl” includes all includes all linear or branched alkyl groups with between 1 and 5 carbon atoms, and thus includes methyl, ethyl, n-propyl, i-propyl, butyl and its isomers (e.g. n-butyl, i-butyl and t-butyl); pentyl and its isomers. For example, “$C_{1-4}$alkyl” includes all linear or branched alkyl groups with between 1 and 4 carbon atoms, and thus includes methyl, ethyl, n-propyl, i-propyl, butyl and its isomers (e.g. n-butyl, i-butyl and t-butyl). For example “$C_{1-3}$alkyl” includes all linear or branched alkyl groups with between 1 and 3 carbon atoms, and thus includes methyl, ethyl, n-propyl, i-propyl.

The term “trifluoromethyl” as used herein refers to the group $—CF_3$.

The term “difluoromethyl” as used herein refers to the group $—CHF_2$.

The term “trifluoromethoxy” as used herein refers to the group $—OCF_3$.

The term “difluoromethoxy” as used herein refers to the group $—OCHF_2$.

The term “$C_{1-6}$alkoxy” or “$C_{1-6}$alkyloxy”, as a group or part of a group, refers to a group having the formula $—OR^b$ wherein $R^b$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

The term “$C_{3-8}$cycloalkyl”, as a group or part of a group, refers to a cyclic alkyl group, that is a monovalent, saturated, hydrocarbyl group having 1 or more cyclic structure, and comprising from 3 to 8 carbon atoms, preferably from 3 to 6, more preferably from 5 to 6 carbon atoms. Cycloalkyl includes all saturated hydrocarbon groups containing one or more rings, including monocyclic or bicyclic groups. The further rings of multi-ring cycloalkyls may be either fused, bridged and/or joined through one or more spiro atoms. Examples of $C_{3-8}$cycloalkyl groups include but are not limited to cyclooctyl, cycloheptyl, cyclopropyl, cyclobutyl, cyclopentyl, and cyclohexyl.

The term "aryl", as a group or part of a group, refers to a polyunsaturated, aromatic hydrocarbyl group having a single ring (i.e. phenyl) or multiple aromatic rings fused together (e.g. naphthyl), or linked covalently, typically comprising 6 to 12 carbon atoms; wherein at least one ring is aromatic, preferably comprising 6 to 10 carbon atoms, wherein at least one ring is aromatic. The aromatic ring may optionally include one to two additional rings (either cycloalkyl, heterocyclyl or heteroaryl) fused thereto. Examples of suitable aryl include $C_{6-12}$aryl, preferably $C_{6-10}$aryl, more preferably $C_{6-8}$aryl. Non-limiting examples of aryl comprise phenyl, biphenylyl, biphenylenyl, or 1- or 2-naphthanelyl; 5- or 6-tetralinyl, 1-, 2-, 3-, 4-, 5-, 6-, 7- or 8-azulenyl, 4-, 5-, 6 or 7-indenyl, 4- or 5-indanyl, 5-, 6-, 7- or 8-tetrahydronaphthyl, 1,2,3,4-tetrahydronaphthyl, and 1,4-dihydronaphthyl; 1-, 2-, 3-, 4- or 5-pyrenyl.

The term "pyrazolyl" (also called "1H-pyrazolyl" and "1,2-diazolyl") as used herein includes pyrazol-1-yl, pyrazol-3-yl, pyrazol-4-yl and pyrazol-5-yl.

The term "pyridyl" (also called "pyridinyl") as used herein includes pyridin-2-yl, pyridin-3-yl and pyridin-4-yl (also called 2-pyridyl, 3-pyridyl and 4-pyridyl).

The term "thiophenyl" (also called "thienyl") as used herein includes thiophen-2-yl and thiophen-3-yl (also called thien-2-yl and thien-3-yl).

Whenever used in the present invention the term "compounds of the invention" or a similar term is meant to include the compounds of general formula (I) and any subgroup thereof.

This term also refers to the compounds as depicted in Table 1 and their derivatives, N-oxides, salts, solvates, hydrates, tautomeric forms, analogues, pro-drugs, esters and metabolites, as well as their quaternized nitrogen analogues. The N-oxide forms of said compounds are meant to comprise compounds wherein one or several nitrogen atoms are oxidized to the so-called N-oxide.

As used herein and unless otherwise stated, the term "stereoisomer" refers to all possible different isomeric as well as conformational forms which the compounds of structural formula herein may possess, in particular all possible stereochemically and conformationally isomeric forms, all diastereomers, enantiomers and/or conformers of the basic molecular structure. Some compounds of the present invention may exist in different tautomeric forms, all of the latter being included within the scope of the present invention.

The present invention includes all possible stereoisomers compounds of formula (I) and any subgroup thereof. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be effected by any suitable method known in the art. See, for example, Stereochemistry of Organic Compounds by E. L. Eliel, S. H. Wilen, and L. N. Mander (Wiley-Interscience, 1994), incorporated by reference with regard to stereochemistry. A structural isomer is a type of isomer in which molecules with the same molecular formula have different bonding patterns and atomic organization. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety.

The term "prodrug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int. Ed. 1992, "Biotransformation of Drugs", p 13-15) describing prodrugs generally is hereby incorporated. Prodrugs of the compounds of the invention can be prepared by modifying functional groups present in said component in such a way that the modifications are cleaved, either in routine manipulation or in vivo, to the parent component. Typical examples of prodrugs are described for instance in WO 99/33795, VO 99/33815, WO 99/33793 and WO 99/33792 all incorporated herein by reference. Prodrugs are characterized by increased bio-availability and are readily metabolized into the active inhibitors in vivo. The term "prodrug", as used herein, means any compound that will be modified to form a drug species, wherein the modification may take place either inside or outside of the body, and either before or after the pre-drug reaches the area of the body where administration of the drug is indicated.

Preferred statements (features) and embodiments of the compounds and processes of this invention are now set forth. Each statement and embodiment of the invention so defined may be combined with any other statement and/or embodiments unless clearly indicated to the contrary. In particular, any feature indicated as being preferred or advantageous may be combined with any other feature or features indicated as being preferred or advantageous.

A first aspect of the present invention provides a compound of formula (I) or a stereoisomer, or tautomer thereof, (I)

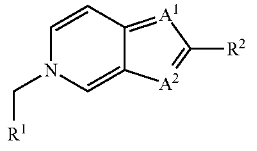

wherein, $A^1$ is N or CH;

$A^2$ is N or CH;

$R^1$ is selected from the group consisting of

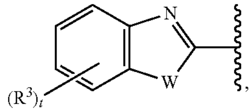,
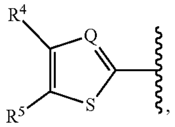,
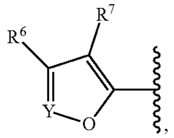,
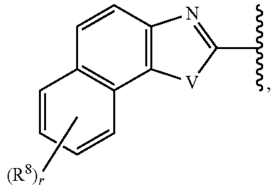, and

-continued

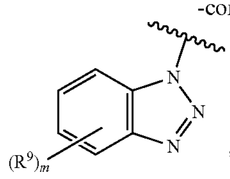

;

wherein the wavy line () indicates the point of attachment to the methylene linker of the main formula (I);

t is an integer selected from 0; 1; 2; 3 and 4;

r is an integer selected from 0; 1; 2; 3 and 4;

m is an integer selected from 0; 1; 2; 3 and 4;

W is selected from the group consisting of $NR^{10}$, S or O;

Q is selected from the group consisting of $CR^{11}$ or N;

Y is selected from the group consisting of N or $CR^{12}$;

V is selected from the group consisting of $NR^{13}$, S or O;

$R^2$ is selected from the group consisting of aryl, pyrazolyl, pyridyl, thiophenyl; wherein said aryl, pyrazolyl, pyridyl, or thiophenyl; are optionally substituted with one or more $Z^1$;

each $R^3$ is independently selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

$R^4$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^2$;

$R^5$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^3$;

$R^6$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^4$;

$R^7$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^5$;

each $R^8$ is independently selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $R^8$ is independently selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

$R^{10}$ is selected from the group consisting of hydrogen, $C_{1-6}$alkyl, $C_{3-8}$cycloalkyl;

$R^{11}$ is selected from the group consisting of hydrogen, $C_{1-6}$alkyl, $C_{3-8}$cycloalkyl;

$R^{12}$ is selected from the group consisting of hydrogen, $C_{1-6}$alkyl, $C_{3-8}$cycloalkyl;

$R^{13}$ is selected from the group consisting of hydrogen, $C_{1-6}$alkyl, $C_{3-8}$cycloalkyl;

each $Z^1$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $Z^2$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $Z^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $Z^4$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $Z^5$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

or a solvate, hydrate, salt or prodrug thereof.

In some embodiments, the compound of the present invention is a compound of formula (I) or a stereoisomer, or tautomer thereof, (I)

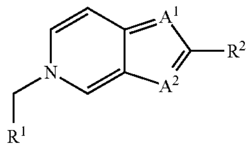

wherein, $A^1$ is N or CH;

$A^2$ is N or CH;

$R^1$ is selected from the group consisting of

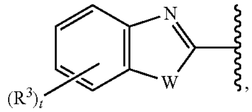

,

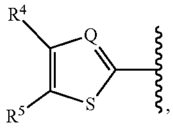

,

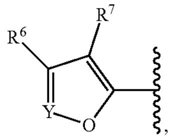

,

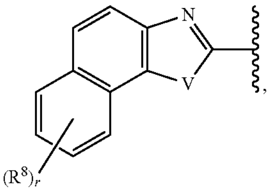

, and

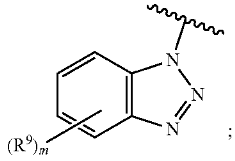

;

wherein the wavy line () indicates the point of attachment to the methylene linker of the main formula (I);

t is an integer selected from 0; 1; 2; 3 and 4;

r is an integer selected from 0; 1; 2; 3 and 4;

m is an integer selected from 0; 1; 2; 3 and 4;

W is selected from the group consisting of $NR^{10}$, S or O;

Q is selected from the group consisting of $CR^{11}$ or N;

Y is selected from the group consisting of N or $CR^{12}$;

V is selected from the group consisting of $NR^{13}$, S or O;

$R^2$ is selected from the group consisting of aryl, pyrazolyl, pyridyl, thiophenyl; wherein said aryl, pyrazolyl, pyridyl, or thiophenyl; are substituted with one or more $Z^1$;

each $R^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

$R^4$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^2$;

$R^5$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^3$;

$R^6$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^4$;

$R^7$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^5$;

each $R^8$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $R^9$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

$R^{10}$ is selected from the group consisting of hydrogen, $C_{1-6}$alkyl, $C_{3-8}$cycloalkyl;

$R^{11}$ is selected from the group consisting of hydrogen, $C_{1-6}$alkyl, $C_{3-8}$cycloalkyl;

$R^{12}$ is selected from the group consisting of hydrogen, $C_{1-6}$alkyl, $C_{3-8}$cycloalkyl;

$R^{13}$ is selected from the group consisting of hydrogen, $C_{1-6}$alkyl, $C_{3-8}$cycloalkyl;

each $Z^1$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $Z^2$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $Z^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $Z^4$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

each $Z^5$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH;

wherein when $R^1$ is

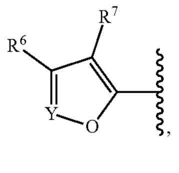

and Y is N, then $R^2$ is not phenyl;

with the proviso that said compound is not:

2-(3-Fluoro-3',4'-dimethyl-biphenyl-4-yl)-5-(4-methyl-thiazol-2-ylmethyl)-5H-imidazo[4,5-c]pyridine;

or a solvate, hydrate, salt or prodrug thereof.

In some embodiments the compound according to the present invention has structural formula (IA), (IB) or (IC)

(IA)

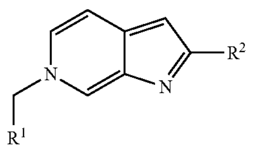

(IB)

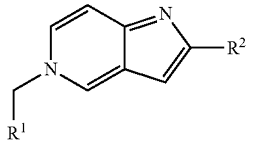

(IC)

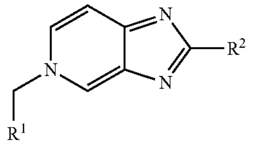

wherein, $R^1$ and $R^2$ have the same meaning as that defined herein.

In some embodiments the compounds have a structure according to formula (I), (IA), (IB) or (IC), wherein $R^1$ is selected from the group consisting of

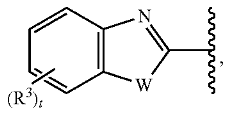

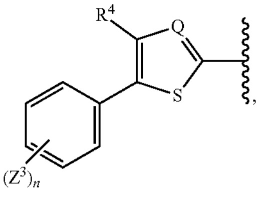

-continued

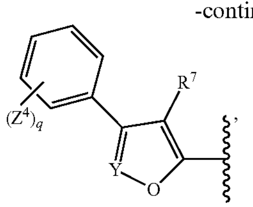

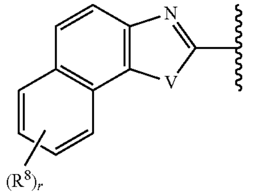

and

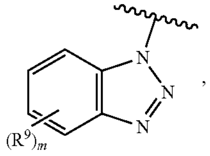

wherein n is an integer selected from 0; 1; 2; 3, 4 and 5; preferably n is selected from 0; 1; 2; and 3;

q is an integer selected from 0; 1; 2; 3, 4 and 5; preferably q is selected from 0; 1; 2; and 3;

and wherein $R^3$, $R^4$, $R^7$, $R^8$, $R^9$, $Z^3$, $Z^4$, W, Q, Y, V, t, r and m have the same meaning as defined herein.

In some embodiments the compounds have a structure according to formula (I), (IA), (IB) or (IC), wherein $R^1$ is selected from the group consisting of

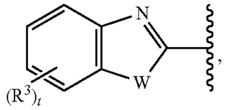

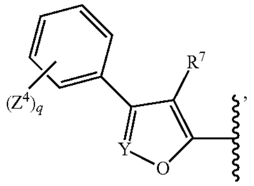

and

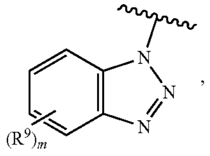

wherein q is an integer selected from 0; 1; 2; 3, 4 and 5; preferably q is selected from 0; 1; 2; and 3;

and wherein $R^3$, $R^7$, $R^9$, $Z^4$, W, Y, t and m have the same meaning as defined herein.

In some embodiments the compounds have a structure according to formula (I), (IA), (IB) or (IC), wherein W is NH, S or O.

In some embodiments the compounds have a structure according to formula (I), (IA), (IB) or (IC), wherein t is an integer selected from 0; 1; 2 and 3; preferably t is selected from 1; 2 and 3.

In some embodiments the compounds have a structure according to formula (I), (IA), (IB) or (IC), wherein Y is N or CH.

In some embodiments the compounds have a structure according to formula (I), (IA), (IB) or (IC), wherein q is an integer selected from 1; 2; 3, and 4; preferably q is selected from 1, 2 and 3.

In some embodiments the compounds have a structure according to formula (I), (IA), (IB) or (IC), wherein m is an integer selected from 0; 1; 2 and 3; preferably m is selected from 0; 1 and 2.

In some embodiments the compounds have a structure according to formula (I), (IA), (IB) or (IC), wherein $R^1$ is

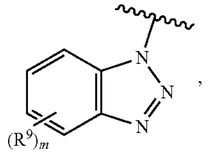

wherein $R^9$ and m have the same meaning as defined herein.

In some embodiments the compounds have a structure according to formula (I), (IA), (IB) or (IC), wherein $R^1$ is

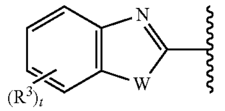

wherein $R^3$, W and t have the same meaning as defined herein.

In some embodiments the compounds have a structure according to formula (I), (IA), (IB) or (IC), wherein $R^1$ is

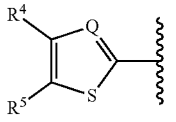

wherein $R^4$, $R^5$, and Q have the same meaning as defined herein; preferably $R^1$ is

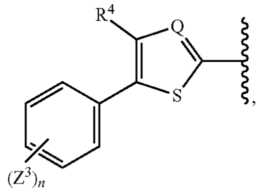

wherein n is an integer selected from 0; 1; 2; 3, 4, $R^4$, $Z^3$ have the same meaning as defined herein; preferably $R^1$ is

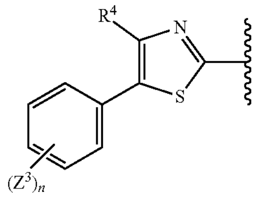

wherein n is an integer selected from 0; 1; 2; 3, 4, $R^4$ and $Z^3$ have the same meaning as defined herein.

In some embodiments the compounds have a structure according to formula (I), (IA), (IB) or (IC), wherein $R^1$ is

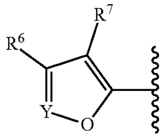

wherein $R^6$, $R^7$, and Y have the same meaning as defined herein; preferably $R^1$ is

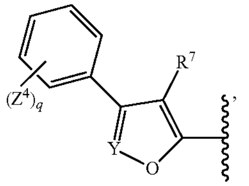

wherein q is an integer selected from 0; 1; 2; 3, 4, $R^7$, $Z^4$ and Y have the same meaning as defined herein; preferably $R^1$ is

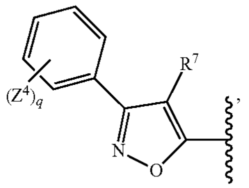

wherein q is an integer selected from 0; 1; 2; 3, 4, $R^7$, and $Z^4$ have the same meaning as defined herein.

In some embodiments the compounds have a structure according to formula (I), (IA), (IB) or (IC), wherein $R^2$ is selected from the group consisting of aryl, pyrazolyl, pyridyl, or thiophenyl, wherein said aryl, pyrazolyl, pyridyl, or thiophenyl are optionally substituted with one, two or three $Z^1$.

In some embodiments the compounds have a structure according to formula (I), (IA), (IB) or (IC), wherein $Z^1$ is selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, —$O(CH_2)_2OH$, cyano.

In some embodiments the compounds have a structure according to formula (I), (IA), (IB) or (IC) are selected from the group consisting of:

1-[[2-[2-fluoro-5-(trifluoromethoxy)phenyl]pyrrolo[2,3-c]pyridin-6-yl]methyl]benzotriazole;

1-[[2-(2-fluorophenyl)pyrrolo[2,3-c]pyridin-6-yl]methyl]benzotriazole;

2-[[2-(2-fluorophenyl)pyrrolo[2,3-c]pyridin-6-yl]methyl]-5-methyl-1,3-benzoxazole;

2-[[2-(2-fluorophenyl)pyrrolo[2,3-c]pyridin-6-yl]methy]-6-methyl-1,3-benzothiazole;

2-[[2-(1,5-dimethylpyrazol-4-yl)pyrrolo[2,3-c]pyridin-6-yl]methyl]-6-methyl-1,3-benzothiazole;

2-[[2-(2-methoxy-3-pyridyl)pyrrolo[2,3-c]pyridin-8-yl]methyl]-6-methyl-1,3-benzothiazole;

[2-[6-[(6-methyl-1,3-benzothiazol-2-yl)methyl]pyrrolo[2,3-c]pyridin-2-yl]phenyl]methanol;

2-[4-fluoro-3-[6-[(6-methyl-1,3-benzothiazol-2-yl)methyl]pyrrolo[2,3-c]pyridin-2-yl]phenoxy]ethanol;

1-[[2-[2-fluoro-5-(trifluoromethoxy)phenyl]pyrrolo[3,2-c]pyridin-5-yl]methyl]benzotriazole;

1-[[2-(2-fluorophenyl)pyrrolo[3,2-c]pyridin-5-yl]methy]benzotriazole;

2-[[2-(2-fluorophenyl)pyrrolo[3,2-c]pyridin-5-yl]methyl]-5-methyl-1,3-benzoxazole;

2-[[2-(2-fluorophenyl)pyrrolo[3,2-c]pyridin-5-yl]methy]-6-methyl-1,3-benzothiazole;

2-[[2-(1,5-dimethylpyrazol-4-yl)pyrrolo[3,2-c]pyridin-5-yl]methyl]-6-methyl-1,3-benzothiazole;

2-[[2-(2-methoxy-3-pyridyl)pyrrolo[3,2-c]pyridin-5-yl]methyl]-6-methyl-1,3-benzothiazole;

[2-[5-[(6-methyl-1,3-benzothiazol-2-yl)methyl]pyrrolo[3,2-c]pyridin-2-yl]phenyl]methanol;

2-[4-fluoro-3-[5-[(6-methyl-1,3-benzothiazol-2-yl)methyl]pyrrolo[3,2-c]pyridin-2-yl]phenoxy]ethanol;

[3-[6-(benzotriazol-1-ylmethyl)pyrrolo[2,3-c]pyridin-2-yl]-4-fluoro-phenoxy]methanol;

1-[[2-(2-methoxyphenyl)pyrrolo[2,3-c]pyridin-6-yl]methyl]benzotriazole;

[2-[6-(benzotriazol-1-ylmethyl)pyrrolo[2,3-c]pyridin-2-yl]phenyl]methanol;

4-[6-(benzotriazol-1-ylmethyl)pyrrolo[2,3-c]pyridin-2-yl]benzonitrile;

1-[[2-(2-methoxy-3-pyridyl)pyrrolo[2,3-c]pyridin-6-yl]methyl]benzotriazole;

2-[[2-(2-methoxy-3-pyridyl)pyrrolo[2,3-c]pyridin-6-yl]methy]-5-methyl-1,3-benzoxazole;

1-[[2-(1,5-dimethylpyrazol-4-yl)pyrrolo[2,3-c]pyridin-6-yl]methyl]benzotriazole;

[2-[6-[(6-methyl-1H-benzimidazol-2-yl)methyl]pyrrolo[2,3-c]pyridin-2-yl]phenyl]methanol;

1-[[2-(1,5-dimethylpyrazol-4-yl)pyrrolo[3,2-c]pyridin-5-yl]methyl]benzotriazole;

2-[3-[5-(benzotriazol-1-ylmethyl)pyrrolo[3,2-c]pyridin-2-yl]-4-fluoro-phenoxy]ethanol;

1-[[2-(2-methoxyphenyl)pyrrolo[3,2-c]pyridin-5-yl]methyl]benzotriazole;

[2-[5-(benzotriazol-1-ylmethyl)pyrrolo[3,2-c]pyridin-2-yl]phenyl]methanol;

4-[5-(benzotriazol-1-ylmethyl)pyrrolo[3,2-c]pyridin-2-yl]benzonitrile;

1-[[2-(2-methoxy-3-pyridyl)pyrrolo[3,2-c]pyridin-5-yl]methyl]benzotriazole

[2-[5-[(5-methyl-1,3-benzoxazol-2-yl)methyl]pyrrolo[3,2-c]pyridin-2-yl]phenyl]methanol;

2-[[2-(2-methoxy-3-pyridyl)pyrrolo[3,2-c]pyridin-5-yl]methyl]-5-methyl-1,3-benzoxazole;

[2-[5-[(6-methyl-1H-benzimidazol-2-yl)methyl]pyrrolo[3,2-c]pyridin-2-yl]phenyl]methanol;

2-(2-methoxy-3-pyridyl)-5-[(6-methyl-1H-benzimidazol-2-yl)methyl]pyrrolo[3,2-c]pyridine;

2-((2-(1,5-dimethyl-1H-pyrazol-4-yl)-5H-imidazo[4,5-c]pyridin-5-yl)methyl)-6-methylbenzo[d]thiazole;

2-((2-(1,5-dimethyl-1H-pyrazol-4-yl)-5H-imidazo[4,5-c]pyridin-5-yl)methyl)-5-methylbenzo[d]thiazole;

2-((2-(1,5-dimethyl-1H-pyrazol-4-yl)-5H-imidazo[4,5-c]pyridin-5-yl)methyl)benzo[d]thiazole;

5-chloro-2-((2-(1,5-dimethyl-1H-pyrazol-4-yl)-5H-imidazo[4,5-c]pyridin-5-yl)methyl)benzo[d]thiazole;

6-chloro-2-((2-(1,5-dimethyl-1H-pyrazol-4-yl)-5H-imidazo[4,5-c]pyridin-5-yl)methyl)benzo[d]thiazole;

2-((2-(1,5-dimethyl-1H-pyrazol-4-yl)-5H-imidazo[4,5-c]pyridin-5-yl)methyl)naphtho[2,1-d]thiazole;

3-(2,5-difluorophenyl)-5-((2-(1,5-dimethyl-1H-pyrazol-4-yl)-5H-imidazo[4,5-c]pyridin-5-yl)methyl)isoxazole;

2-((2-(1,5-dimethyl-1H-pyrazol-4-yl)-5H-imidazo[4,5-c]pyridin-5-yl)methyl)-5-methylbenzo[d]oxazole;

2-((2-(1,5-dimethyl-1H-pyrazol-4-yl)-5H-imidazo[4,5-c]pyridin-5-yl)methyl)-5-methylbenzo[d]oxazole;

3-(2,5-difluorophenyl)-5-((2-(1,5-dimethyl-1H-pyrazol-4-yl)-5H-imidazo[4,5-c]pyridin-5-yl)methyl)isoxazole;

2-((2-(1,5-dimethyl-1H-pyrazol-4-yl)-5H-imidazo[4,5-c]pyridin-5-yl)methyl)-5-methylbenzo[d]oxazole;

1-((2-(1,5-dimethyl-1H-pyrazol-4-yl)-5H-imidazo[4,5-c]pyridin-5-yl)methyl)-1H-benzo[d][1,2,3]triazole;

2-((2-(1,3-dimethyl-1H-pyrazol-4-yl)-5H-imidazo[4,5-c]pyridin-5-yl)methyl)-6-methylbenzo[d]thiazole;

2-((2-(1,3-dimethyl-1H-pyrazol-4-yl)-5H-imidazo[4,5-c]pyridin-5-yl)methyl)-5-methylbenzo[d]thiazole;

2-((2-(1,3-dimethyl-1H-pyrazol-4-yl)-5H-imidazo[4,5-c]pyridin-5-yl)methyl)-5-methylbenzo[d]oxazole;

3-(2,5-difluorophenyl)-5-((2-(1,3,5-trimethyl-1H-pyrazol-4-yl)-5H-imidazo[4,5-c]pyridin-5-yl)methyl)isoxazole;

2-((2-(2-methoxypyridin-3-yl)-5H-imidazo[4,5-c]pyridin-5-yl)methyl)-8-methylbenzo[d]thiazole;

2-((2-(2-methoxypyridin-3-yl)-5H-imidazo[4,5-c]pyridin-5-yl)methyl)-5-methylbenzo[d]thiazole;

2-((2-(2-methoxypyridin-3-yl)-5H-imidazo[4,5-c]pyridin-5-yl)methyl)-5-methylbenzo[d]oxazole;

3-(2,5-difluorophenyl)-5-((2-(2-methoxypyridin-3-yl)-5H-imidazo[4,5-c]pyridin-5-yl)methyl)isoxazole;

2-((2-(2-methoxyphenyl)-5H-imidazo[4,5-c]pyridin-5-yl)methyl)-8-methylbenzo[d]thiazole;

3-(2,5-difluorophenyl)-5-((2-(2-methoxyphenyl)-5H-imidazo[4,5-c]pyridin-5-yl)methyl)isoxazole;

1-((2-(2-methoxyphen)-5H-imidazo[4,5-c]pyridin-5-yl)methyl)-1H-benzo[d][1,2,3]triazole;

2-((2-(2-(difluoromethoxy)phenyl)-5H-imidazo[4,5-c]pyridin-5-yl)methyl)-6-methylbenzo[d]thiazole;

2-((2-(2-fluorophenyl)-5H-imidazo[4,5-c]pyridin-5-yl)methyl)-6-methylbenzo[d]thiazole;

2-((2-(2-fluorophenyl)-5H-imidazo[4,5-c]pyridin-5-yl)methyl)-5-methylbenzo[d]thiazole;

2-((2-(2-fluorophenyl)-5H-imidazo[4,5-c]pyridin-5-yl)methyl)benzo[d]thiazole;

6-chloro-2-((2-(2-fluorophenyl)-5H-imidazo[4,5-c]pyridin-5-yl)methyl)benzo[d]thiazole;

5-chlor-2-((2-(2-fluorophenyl)-5H-imidazo[4,5-c]pyridin-5-yl)methyl)benzo[d]thiazole;

(2-((2-(2-fluorophenyl)-5H-imidazo[4,5-c]pyridin-5-yl)methyl)benzo[d]thiazol-6-yl)methanol;

2-((2-(2-fluorophenyl)-5H-imidazo[4,5-c]pyridin-5-yl)methyl)-5-phenylthiazole;

2-((2-(2-fluorophenyl)-5H-imidazo[4,5-c]pyridin-5-yl)methyl)-4-methyl-5-phenylthiazole;

5-((5-chlorothiophen-2-yl)methyl)-2-(2-fluorophenyl)-5H-imidazo[4,5-c]pyridine;

2-((2-(2-fluorophenyl)-5H-imidazo[4,5-c]pyridin-5-yl)methyl)-5-methylbenzo[d]oxazole;

2-((2-(2-fluorophenyl)-5H-imidazo[4,5-c]pyridin-5-yl)methyl)-6-methylbenzo[d]oxazole;

2-((2-(2-fluorophenyl)-5H-imidazo[4,5-c]pyridin-5-yl)methyl)-5-methoxybenzo[d]oxazole;

3-(2,4-difluorophenyl)-5-((2-(2-fluorophenyl)-5H-imidazo[4,5-c]pyridin-5-yl)methyl)isoxazole;

3-(2,5-difluorophenyl)-5-((2-(2-fluorophenyl)-5H-imidazo[4,5-c]pyridin-5-yl)methyl)isoxazole;

2-(2-fluorophenyl)-5-((6-methyl-1H-benzo[d]imidazol-2-yl)methyl)-5H-imidazo[4,5-c]pyridine;

5-((6-fluoro-1H-benzo[d]imidazol-2-yl)methyl)-2-(2-fluorophenyl)-5H-imidazo[4,5-c]pyridine;

1-((2-(2-fluorophenyl)-5H-imidazo[4,5-c]pyridin-5-yl)methyl)-1H-benzo[d][1,2,3]triazole;

3-(2,5-difluorophenyl)-5-((2-(3-fluorophenyl)-5H-imidazo[4,5-c]pyridin-5-yl)methyl)isoxazole;

1-((2-(2-fluoro-5-(trifluoromethoxy)phenyl)-5H-imidazo[4,5-c]pyridin-5-yl)methyl)-1H-benzo[d][1,2,3]triazole;

2-(4-fluoro-3-(5-((6-methylbenzo[d]thiazol-2-yl)methyl)-5H-imidazo[4,5-c]pyridin-2-yl)phenoxy)ethan-1-ol;

2-(3-(5-((3-(2,5-difluorophenyl)isoxazol-5-yl)methyl)-5H-imidazo[4,5-c]pyridin-2-yl)-4-fluorophenoxy)ethan-1-ol;

4-(5-((3-(2,5-difluorophenyl)isoxazol-5-yl)methyl)-5H-imidazo[4,5-c]pyridin-2-yl)benzonitrile;

3-(5-((3-(2,5-difluorophenyl)isoxazol-5-yl)methyl)-5H-imidazo[4,5-c]pyridin-2-yl)-N,N-dimethylaniline;

(2-(5-((6-methylbenzo[d]thiazol-2-yl)methyl)-5H-imidazo[4,5-c]pyridin-2-yl)phenyl)methanol;

(2-(5-((3-(2,5-difluorophenyl)isoxazol-5-yl)methyl)-5H-imidazo[4,5-c]pyridin-2-yl)phenyl)methanol;

3-(2,5-difluorophenyl)-5-((2-(5-methylthiophen-2-yl)-5H-imidazo[4,5-c]pyridin-5-yl)methyl)isoxazole;

3-(2,5-difluorophenyl)-5-((2-(5-methylthiophen-3-yl)-5H-imidazo[4,5-c]pyridin-5-yl)methyl)isoxazole;

3-(2,5-difluorophenyl)-5-((2-(4,5-dimethylthiophen-3-yl)-5H-imidazo[4,5-c]pyridin-5-yl)methyl)isoxazole.

According to a second aspect, the present invention also encompasses a pharmaceutical composition comprising one or more pharmaceutically acceptable excipients and a therapeutically effective amount of a compound according to the first aspect of the invention.

The inventors are the first to demonstrate, by in vivo studies, that the compounds of the present invention are effective in the treatment of viral infections. Accordingly, in a further and third aspect, the present invention also encompasses a compound according to the first aspect of the invention, or a pharmaceutical composition according to the second aspect of the invention, for use as a medicament. According to a fourth aspect, the present invention also encompasses a compound according to the first aspect of the invention, or a pharmaceutical composition according to the second aspect of the invention, for use as a medicine for the prevention and/or treatment an infection caused by pestivirus in an animal; preferably a mammal; more preferably a bovine, a pig, a sheep, or a goat. In particular embodiments, the animals are cows, most particularly calves.

In particular embodiments, the anti-pestivirus activity, such as the anti-BVD activity, of the claimed compounds is particularly strong compared to prior art compounds. In particular embodiments, the compounds of the present invention have low toxicity.

In some embodiments, the present invention also encompasses a compound according to the first aspect of the invention, or compound 2-(3-Fluoro-3',4'-dimethyl-biphenyl-4-yl)-5-(4-methyl-thiazol-2-ylmethyl)-5H-imidazo[4,5-c]pyridine, for use as a medicine for the prevention and/or treatment an infection caused by pestivirus in an animal; preferably a mammal; more preferably a bovine, a pig, a sheep, or a goat.

In some embodiments of the present invention, the pestivirus infection is an infection caused by bovine viral diarrhea virus, classical swine fever virus, border disease virus, atypical porcine pestivirus, or HoBi-like virus.

The present invention also contemplates a method of prevention and/or treatment of an infection caused by bovine viral diarrhea virus comprising administering an effective amount of a compound as defined herein, or a pharmaceutical composition as defined herein to a subject in need thereof, wherein the subject is an animal; preferably a mammal; more preferably a bovine, a pig, a sheep, or a goat.

The application provides compounds of formula (I) or a stereoisomer, or tautomer, wherein $A^1$ is N or CH;

$A^2$ is N or CH;

$R^1$ is selected from the group consisting of

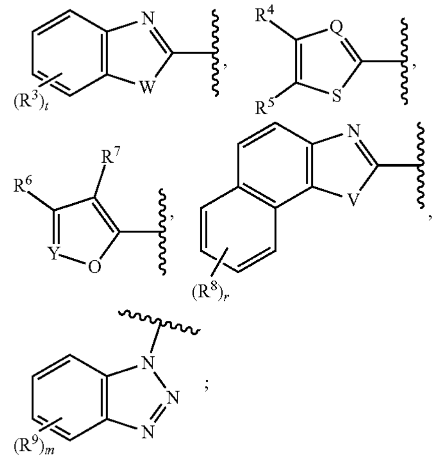

, and ;

wherein the wavy line ( ) indicates the point of attachment to the methylene linker of the main formula (I);

t is an integer selected from 0; 1; 2; 3 and 4; preferably t is selected from 0; 1; 2; 3; preferably t is selected from 0; 1; and 2; preferably t is selected from 1; and 2; preferably t is 1;

r is an integer selected from 0; 1; 2; 3 and 4; preferably r is selected from 0; 1; 2; 3;

preferably r is selected from 0; 1; and 2; preferably r is selected from 0; and 1; preferably r is 0;

m is an integer selected from 0; 1; 2; 3 and 4; preferably m is selected from 0; 1; 2; 3; preferably m is selected from 0; 1; and 2; preferably m is selected from 0; and 1; preferably m is 0;

W is selected from the group consisting of $NR^{10}$, S or O; preferably W is selected from NH, S or O; preferably W is S; preferably W is O;

Q is selected from the group consisting of N or $CR^{11}$; preferably Q is selected from of N or CH;

Y is selected from the group consisting of N or $CR^{12}$; preferably Y is selected from of N or CH; preferably Y is N;

V is selected from the group consisting of $NR^{13}$, S or O; preferably V is selected from NH, S or O; preferably V is S; preferably V is O;

In particular embodiments in $R^1$, W is S or O; In particular embodiments, in $R^1$, V is S.

$R^2$ is selected from the group consisting of aryl, pyrazolyl, pyridyl, thiophenyl; wherein said aryl, pyrazolyl, pyridyl, or thiophenyl; are optionally substituted with one or more $Z^1$; preferably $R^2$ is $C_{1-12}$aryl, pyrazolyl, pyridyl, thiophenyl; preferably $R^2$ is $C_{1-10}$aryl, pyrazolyl, pyridyl, thiophenyl; preferably $R^2$ is aryl, pyrazol-3-yl, pyrazol-4-yl, pyrazol-5-yl, 2-pyridyl, 3-pyridyl, 4-pyridyl, thiophenyl; preferably $R^2$ is $C_{1-2}$aryl, pyrazol-3-yl, pyrazol-4-yl, pyrazol-5-yl, 2-pyridyl, 3-pyridyl, 4-pyridyl, thiophenyl; preferably $R^2$ is $C_{1-10}$aryl, pyrazol-3-yl, pyrazol-4-yl, pyrazol-5-yl, 2-pyridyl, 3-pyridyl, 4-pyridyl, thiophenyl;

each $R^3$ is independently selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH; preferably $R^3$ is hydrogen, halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$; preferably $R^3$ is hydrogen, halo, trifluoromethyl, difluoromethyl, $C_{1-3}$alkoxy, trifluoromethoxy, difluoromethoxy, hydroxyl, $C_{1-3}$alkyl, —$CH_2OH$, —$CH_2N(CH_3)_2$, —$O(CH_2)_2OH$, —$O(CH_2)_2OCH_3$; preferably $R^3$ is hydrogen, halo, trifluoromethyl, difluoromethyl, methoxy, trifluoromethoxy, difluoromethoxy, hydroxyl, methyl, —$CH_2OH$, —$CH_2N(CH_3)_2$, —$O(CH_2)_2OH$, —$O(CH_2)_2OCH_3$;

$R^4$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^2$; preferably $R^4$ is hydrogen, halo, $C_{1-6}$alkyl, $C_{1-12}$aryl, trifluoromethyl, difluoromethyl, $C_{1-6}$alkoxy, trifluoromethoxy, difluoromethoxy, hydroxyl, pyrazolyl, pyridyl, thiophenyl; preferably $R^4$ is hydrogen, halo, $C_{1-6}$alkyl, aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl; preferably $R^4$ is hydrogen, halo, $C_{1-6}$alkyl, $C_{1-12}$aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl; preferably $R^4$ is hydrogen, halo, $C_{1-6}$alkyl, $C_{1-10}$aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl;

$R^5$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^3$; preferably $R^5$ is hydrogen, halo, $C_{1-6}$alkyl, $C_{1-12}$aryl, trifluoromethyl, difluoromethyl, $C_{1-6}$alkoxy, trifluoromethoxy, difluoromethoxy, hydroxyl, pyrazolyl, pyridyl, thiophenyl; preferably $R^5$ is hydrogen, halo, $C_{1-6}$alkyl, aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl; preferably $R^5$ is hydrogen, halo, $C_{1-6}$alkyl, $C_{1-12}$aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl; preferably $R^5$ is hydrogen, halo, $C_{1-6}$alkyl, $C_{1-10}$aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl;

$R^8$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^4$; preferably $R^5$ is hydrogen, halo, $C_{1-6}$alkyl, $C_{1-12}$aryl, trifluoromethyl, difluoromethyl, $C_{1-6}$alkoxy, trifluoromethoxy, difluoromethoxy, hydroxyl, pyrazolyl, pyridyl, thiophenyl; preferably $R^6$ is hydrogen, halo, $C_{1-6}$alkyl, aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl; preferably $R^6$ is hydrogen, halo, $C_{1-6}$alkyl, $C_{1-12}$aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl; preferably $R^6$ is hydrogen, halo, $C_{1-6}$alkyl, $C_{1-10}$aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl;

$R^7$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^5$; preferably $R^7$ is hydrogen, halo, $C_{1-6}$alkyl, $C_{1-12}$aryl, trifluoromethyl, difluoromethyl, $C_{1-6}$alkoxy, trifluoromethoxy, difluoromethoxy, hydroxyl, pyrazolyl, pyridyl, thiophenyl; preferably $R^7$ is hydrogen, halo, $C_{1-6}$alkyl, aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl; preferably $R^7$ is hydrogen, halo, $C_{1-6}$alkyl, $C_{1-12}$aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl; preferably $R^7$ is hydrogen, halo, $C_{1-6}$alkyl, $C_{1-10}$aryl, trifluoromethyl, difluoromethyl, $C_{1-6}$alkoxy, pyrazol-3-yl, pyrazol-4-yl, pyrazol-5-yl, 2-pyridyl, 3-pyridyl, 4-pyridyl, thiophenyl;

each $R^8$ is selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH; preferably $R^8$ is hydrogen, halo, trifluoromethyl, difluoromethyl, $C_{1-4}$alkoxy, trifluoromethoxy, difluoromethoxy, hydroxyl, $C_{1-4}$alkyl, $—CH_2OH$, $—CH_2N(CH_3)_2$, $—O(CH_2)_2OH$, $—O(CH_2)_2OCH_3$; preferably $R^8$ is hydrogen, halo, trifluoromethyl, difluoromethyl, $C_{1-6}$alkoxy, trifluoromethoxy, difluoromethoxy, hydroxyl, $C_{1-3}$alkyl, $—CH_2OH$, $—CH_2N(CH_3)_2$, $—O(CH_2)_2OH$, $—O(CH_2)_2OCH_3$; preferably $R^8$ is hydrogen, halo, trifluoromethyl, difluoromethyl, methoxy, trifluoromethoxy, difluoromethoxy, hydroxyl, methyl $—CH_2OH$, $—CH_2N(CH_3)_2$, $—O(CH_2)_2OH$, $—O(CH_2)_2OCH_3$;

each $R^9$ is selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH; preferably $R^9$ is hydrogen, halo, trifluoromethyl, difluoromethyl, $C_{1-4}$alkoxy, trifluoromethoxy, difluoromethoxy, hydroxyl, $C_{1-4}$alkyl, $—CH_2OH$, $—CH_2N(CH_3)_2$, $—O(CH_2)_2OH$, $—O(CH_2)_2OCH_3$; preferably $R^9$ is hydrogen, halo, trifluoromethyl, difluoromethyl, $C_{1-3}$alkoxy, trifluoromethoxy, difluoromethoxy, hydroxyl, $C_{1-6}$alkyl, $—CH_2OH$, $—CH_2N(CH_3)_2$, $—O(CH_2)_2OH$, $—O(CH_2)_2OCH_3$; preferably $R^9$ is hydrogen, halo, trifluoromethyl, difluoromethyl, methoxy, trifluoromethoxy, difluoromethoxy, hydroxyl, methyl $—CH_2OH$, $—CH_2N(CH_3)_2$, $—O(CH_2)_2OH$, $—O(CH_2)_2OCH_3$;

$R^{10}$ is selected from the group consisting of hydrogen, $C_{1-6}$alkyl, $C_{3-8}$cycloalkyl; preferably $R^{10}$ is hydrogen, $C_{1-4}$alkyl, $C_{3-8}$cycloalkyl; preferably $R^{10}$ is hydrogen, $C_{1-3}$alkyl, $C_{5-8}$cycloalkyl;

$R^{11}$ is selected from the group consisting of hydrogen, $C_{1-6}$alkyl, $C_{3-8}$cycloalkyl; preferably $R^{11}$ is hydrogen, $C_{1-4}$alkyl, $C_{3-8}$cycloalkyl; preferably $R^{11}$ is hydrogen, $C_{1-3}$alkyl, $C_{5-8}$cycloalkyl;

$R^{12}$ is selected from the group consisting of hydrogen, $C_{1-6}$alkyl, $C_{3-8}$cycloalkyl; preferably $R^{12}$ is hydrogen, $C_{1-4}$alkyl, $C_{3-8}$cycloalkyl; preferably $R^{12}$ is hydrogen, $C_{1-3}$alkyl, $C_{5-8}$cycloalkyl;

$R^{13}$ is selected from the group consisting of hydrogen, $C_{1-6}$alkyl, $C_{3-8}$cycloalkyl; preferably $R^{13}$ is hydrogen, $C_{1-4}$alkyl, $C_{3-6}$cycloalkyl; preferably $R^{13}$ is hydrogen, $C_{1-3}$alkyl, $C_{5-8}$cycloalkyl;

each $Z^1$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH; preferably $Z^1$ is halo, trifluoromethyl, difluoromethyl, $C_{1-4}$alkoxy, trifluoromethoxy, difluoromethoxy, hydroxyl, $C_{1-4}$alkyl, $—CH_2OH$, $—CH_2N(CH_3)_2$, $—O(CH_2)_2OH$, $—O(CH_2)_2OCH_3$, cyano; preferably $Z^1$ is halo, trifluoromethyl, difluoromethyl, $C_{1-6}$alkoxy, trifluoromethoxy, difluoromethoxy, hydroxyl, $C_{1-6}$alkyl, $—CH_2OH$, $—CH_2N(CH_3)_2$, $—O(CH_2)_2OH$, $—O(CH_2)_2OCH_3$, cyano; preferably $Z^1$ is halo, trifluoromethyl, difluoromethyl, methoxy, trifluoromethoxy, difluoromethoxy, hydroxyl, methyl, ethyl, propyl, $—CH_2OH$, $—CH_2N(CH_3)_2$, $—O(CH_2)_2OH$, $—O(CH_2)_2OCH_3$, cyano; preferably $Z^1$ is F, Cl, trifluoromethyl, difluoromethyl, methoxy, ethoxy, trifluoromethoxy, difluoromethoxy, hydroxyl, $C_{1-6}$alkyl, $—CH_2OH$, $—CH_2N(CH_3)_2$, $—O(CH_2)_2OH$, $—O(CH_2)_2OCH_3$, cyano;

each $Z^2$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH; preferably $Z^2$ is halo, trifluoromethyl, difluoromethyl, $C_{1-4}$alkoxy, trifluoromethoxy, difluoromethoxy, hydroxyl, $C_{1-6}$alkyl, $—CH_2OH$, $—CH_2N(CH_3)_2$, $—O(CH_2)_2OH$, $—O(CH_2)_2OCH_3$, cyano; preferably $Z^2$ is halo, trifluoromethyl, difluoromethyl, $C_{1-6}$alkoxy, trifluoromethoxy, difluoromethoxy, hydroxyl, $C_{1-6}$alkyl, $—CH_2OH$, $—CH_2N(CH_3)_2$, $—O(CH_2)_2OH$, $—O(CH_2)_2OCH_3$, cyano; preferably $Z^2$ is halo, trifluoromethyl, difluoromethyl, methoxy, trifluoromethoxy, difluoromethoxy, hydroxyl, methyl, ethyl, propyl, $—CH_2OH$, $—CH_2N(CH_3)_2$, $—O(CH_2)_2OH$, $—O(CH_2)_2OCH_3$, cyano; preferably $Z^2$ is F, Cl, trifluoromethyl, difluoromethyl, methoxy, ethoxy, trifluoromethoxy, difluoromethoxy, hydroxyl, $C_{1-4}$alkyl, $—CH_2OH$, $—CH_2N(CH_3)_2$, $—O(CH_2)_2OH$, $—O(CH_2)_2OCH_3$, cyano;

each $Z^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro, —COOH; preferably $Z^3$ is halo, trifluoromethyl, difluoromethyl, $C_{1-4}$alkoxy, trifluoromethoxy, difluoromethoxy, hydroxyl, $C_{1-4}$alkyl, $—CH_2OH$, $—CH_2N(CH_3)_2$, $—O(CH_2)_2OH$, $—O(CH_2)_2OCH_3$, cyano; preferably $Z^3$ is halo, trifluoromethyl, difluoromethyl, $C_{1-6}$alkoxy, trifluoromethoxy, difluoromethoxy, hydroxyl, $C_{1-6}$alkyl, $—CH_2OH$, $—CH_2N(CH_3)_2$, $—O(CH_2)_2OH$, $—O(CH_2)_2OCH_3$, cyano; preferably $Z^3$ is halo, trifluoromethyl, difluoromethyl, methoxy, trifluoromethoxy, difluoromethoxy, hydroxyl, methyl, ethyl, propyl, $—CH_2OH$, $—CH_2N(CH_3)_2$, $—O(CH_2)_2OH$, $—O(CH_2)_2OCH_3$, cyano; preferably $Z^3$ is F, Cl, trifluoromethyl, difluoromethyl, methoxy, ethoxy, trifluoromethoxy, difluoromethoxy, hydroxyl, $C_{1-4}$alkyl, $—CH_2OH$, $—CH_2N(CH_3)_2$, $—O(CH_2)_2OH$, $—O(CH_2)_2OCH_3$, cyano;

each $Z^4$ is independently selected from the group consisting of halo, trifluoromethyl, difluoromethyl, $C_{1-4}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH; preferably $Z^4$ is halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano; preferably $Z^4$ is halo, trifluoromethyl, difluoromethyl, $C_{1-6}$alkoxy, trifluoromethoxy, difluoromethoxy, hydroxyl, $C_{1-6}$alkyl, —$CH_2OH$, —$CH_2N(CH_3)_2$, —$O(CH_2)_2OH$, —$O(CH_2)_2OCH_3$, cyano; preferably $Z^4$ is halo, trifluoromethyl, difluoromethyl, methoxy, trifluoromethoxy, difluoromethoxy, hydroxyl, methyl, ethyl, propyl, —$CH_2OH$, —$CH_2N(CH_3)_2$, —$O(CH_2)_2OH$, —$O(CH_2)_2OCH_3$, cyano; preferably $Z^4$ is F, Cl, trifluoromethyl, difluoromethyl, methoxy, ethoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano;

each $Z^5$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH; preferably $Z^5$ is halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano; preferably $Z^5$ is halo, trifluoromethyl, difluoromethyl, $C_{1-3}$alkoxy, trifluoromethoxy, difluoromethoxy, hydroxyl, $C_{1-3}$alkyl, —$CH_2OH$, —$CH_2N(CH_3)_2$, —$O(CH_2)_2OH$, —$O(CH_2)_2OCH_3$, cyano; preferably $Z^5$ is halo, trifluoromethyl, difluoromethyl, methoxy, trifluoromethoxy, difluoromethoxy, hydroxyl, methyl, ethyl, propyl, —$CH_2OH$, —$CH_2N(CH_3)_2$, —$O(CH_2)_2OH$, —$O(CH_2)_2OCH_3$, cyano; preferably $Z^5$ is F, Cl, trifluoromethyl, difluoromethyl, methoxy, ethoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano.

In some embodiments $A^1$ and $A^2$ are different from each other.

In some embodiments $R^2$ is selected from the group consisting of aryl, pyrazolyl, pyridyl, thiophenyl; wherein said aryl, pyrazolyl, pyridyl, or thiophenyl; are optionally substituted with one or more $Z^1$; preferably $R^2$ is $C_{1-12}$aryl, pyrazolyl, pyridyl, thiophenyl; preferably $R^2$ is $C_{1-10}$aryl, pyrazolyl, pyridyl, thiophenyl; preferably $R^2$ is aryl, pyrazol-3-yl, pyrazol-4-yl, pyrazol-5-yl, 2-pyridyl, 3-pyridyl, 4-pyridyl, thiophenyl; preferably $R^2$ is $C_{1-12}$aryl, pyrazol-3-yl, pyrazol-4-yl, pyrazol-5-yl, 2-pyridyl, 3-pyridyl, 4-pyridyl, thiophenyl; preferably $R^2$ is $C_{1-10}$aryl, pyrazol-3-yl, pyrazol-4-yl, pyrazol-5-yl, 2-pyridyl, 3-pyridyl, 4-pyridyl, thiophenyl.

In some embodiments $R^2$ is pyrazolyl optionally substituted with one or more $Z^1$; preferably $R^2$ is pyrazolyl optionally substituted with one, two or three $Z^1$; preferably $R^2$ is pyrazolyl optionally substituted with one or two $Z^1$.

In some embodiments $R^3$ is selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, —$CH_2OH$, —$CH_2N(CH_2)_2$, —$O(CH_2)_2OH$, —$O(CH_2)_2OCH_3$; cyano, nitro, —COOH; preferably $R^3$ is hydrogen, halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$; preferably $R^3$ is hydrogen, halo, trifluoromethyl, difluoromethyl, $C_{1-3}$alkoxy, trifluoromethoxy, difluoromethoxy, hydroxyl, $C_{1-3}$alkyl, —$CH_2OH$, —$CH_2N(CH_3)_2$, —$O(CH_2)_2OH$, —$O(CH_2)$ $_2OCH_3$; preferably $R^3$ is hydrogen, halo, trifluoromethyl, difluoromethyl, methoxy, trifluoromethoxy, difluoromethoxy, hydroxyl, methyl, —$CH_2OH$, —$CH_2N(CH_3)_2$, —$O(CH_2)_2OH$, —$O(CH_2)_2OCH_3$.

In some embodiments $R^4$ is selected from the group consisting of hydrogen, halo, $C_{1-6}$alkyl, $C_{1-12}$aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^2$; preferably $R^4$ is hydrogen, halo, $C_{1-4}$alkyl, trifluoromethyl, difluoromethyl, $C_{1-4}$alkoxy, trifluoromethoxy, difluoromethoxy, hydroxyl, pyrazol-3-yl, pyrazol-4-yl, pyrazol-5-yl, 2-pyridyl, 3-pyridyl, 4-pyridyl, thiophenyl; preferably $R^4$ is hydrogen, halo, $C_{1-3}$alkyl, $C_{1-10}$aryl, trifluoromethyl, difluoromethyl, $C_{1-3}$alkoxy, trifluoromethoxy, difluoromethoxy, hydroxyl, pyrazol-3-yl, pyrazol-4-yl, pyrazol-5-yl, 2-pyridyl, 3-pyridyl, 4-pyridyl, thiophenyl; preferably $R^4$ is hydrogen, halo, trifluoromethyl, difluoromethyl, methoxy, trifluoromethoxy, difluoromethoxy, hydroxyl, methyl, phenyl, pyrazol-3-yl, pyrazol-4-yl, pyrazol-5-yl, 2-pyridyl, 3-pyridyl, 4-pyridyl, thiophenyl.

In some embodiments R is selected from the group consisting of hydrogen, halo, $C_{1-6}$alkyl, $C_{1-12}$aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^3$; preferably $R^5$ is hydrogen, halo, $C_{1-4}$alkyl, trifluoromethyl, difluoromethyl, $C_{1-4}$alkoxy, trifluoromethoxy, difluoromethoxy, hydroxyl, pyrazol-3-yl, pyrazol-4-yl, pyrazol-5-yl, 2-pyridyl, 3-pyridyl, 4-pyridyl, thiophenyl; preferably $R^5$ is hydrogen, halo, $C_{1-3}$alkyl, $C_{1-10}$aryl, trifluoromethyl, difluoromethyl, $C_{1-3}$alkoxy, trifluoromethoxy, difluoromethoxy, hydroxyl, pyrazol-3-yl, pyrazol-4-yl, pyrazol-5-yl, 2-pyridyl, 3-pyridyl, 4-pyridyl, thiophenyl; preferably $R^5$ is hydrogen, halo, trifluoromethyl, difluoromethyl, methoxy, trifluoromethoxy, difluoromethoxy, hydroxyl, methyl, phenyl, pyrazol-3-yl, pyrazol-4-yl, pyrazol-5-yl, 2-pyridyl, 3-pyridyl, 4-pyridyl, thiophenyl.

In some embodiments $R^6$ is selected from the group consisting of hydrogen, halo, $C_{1-6}$alkyl, $C_{1-12}$aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^4$; preferably $R^6$ is hydrogen, halo, $C_{1-4}$alkyl, trifluoromethyl, difluoromethyl, $C_{1-4}$alkoxy, trifluoromethoxy, difluoromethoxy, hydroxyl, pyrazol-3-yl, pyrazol-4-yl, pyrazol-5-yl, 2-pyridyl, 3-pyridyl, 4-pyridyl, thiophenyl; preferably $R^6$ is hydrogen, halo, $C_{1-3}$alkyl, $C_{1-10}$aryl, trifluoromethyl, difluoromethyl, $C_{1-3}$alkoxy, trifluoromethoxy, difluoromethoxy, hydroxyl, pyrazol-3-yl, pyrazol-4-yl, pyrazol-5-yl, 2-pyridyl, 3-pyridyl, 4-pyridyl, thiophenyl; preferably $R^6$ is hydrogen, halo, trifluoromethyl, difluoromethyl, methoxy, trifluoromethoxy, difluoromethoxy, hydroxyl, methyl, phenyl, pyrazol-3-yl, pyrazol-4-yl, pyrazol-5-yl, 2-pyridyl, 3-pyridyl, 4-pyridyl, thiophenyl.

In some embodiments $R^7$ is selected from the group consisting of hydrogen, halo, $C_{1-6}$alkyl, $C_{1-12}$aryl, trifluoromethyl, difluoromethyl, $C_{1-6}$alkoxy, trifluoromethoxy, difluoromethoxy, hydroxyl, pyrazolyl, pyridyl, thiophenyl; wherein said aryl, pyrazolyl, pyridyl, or thiophenyl; are optionally substituted with one or more $Z^5$; preferably $R^7$ is hydrogen, halo, $C_{1-4}$alkyl, trifluoromethyl, difluoromethyl, $C_{1-4}$alkoxy, trifluoromethoxy, difluoromethoxy, hydroxyl, pyrazol-3-yl, pyrazol-4-yl, pyrazol-5-yl, 2-pyridyl, 3-pyridyl, 4-pyridyl, thiophenyl; preferably $R^7$ is hydrogen, halo, $C_{1-3}$alkyl, $C_{1-10}$aryl, trifluoromethyl, difluoromethyl, $C_{1-3}$ alkoxy, trifluoromethoxy, difluoromethoxy, hydroxyl, pyrazol-3-yl, pyrazol-4-yl, pyrazol-5-yl, 2-pyridyl, 3-pyridyl, 4-pyridyl, thiophenyl; preferably $R^7$ is hydrogen, halo, trifluoromethyl, difluoromethyl, methoxy, trifluoromethoxy, difluoromethoxy, hydroxyl, methyl, phenyl, pyrazol-3-yl, pyrazol-4-yl, pyrazol-5-yl, 2-pyridyl, 3-pyridyl, 4-pyridyl, thiophenyl.

In some embodiments $R^8$ is selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, —$CH_2OH$, —$CH_2N(CH_3)_2$, —$O(CH_2)_2OH$, —$O(CH_2)_2OCH_3$; cyano, nitro, —COOH; preferably $R^8$ is hydrogen, halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$; preferably $R^8$ is hydrogen, halo, trifluoromethyl, difluoromethyl, $C_{1-3}$alkoxy, trifluoromethoxy, difluoromethoxy, hydroxyl, $C_{1-3}$alkyl, —$CH_2OH$, —$CH_2N(CH_3)_2$, —$O(CH_2)_2OH$, —$O(CH_2)_2OCH_3$; preferably $R^8$ is hydrogen, halo, trifluoromethyl, difluoromethyl, methoxy, trifluoromethoxy, difluoromethoxy, hydroxyl, methyl —$CH_2OH$, —$CH_2N(CH)_2$, —$O(CH_2)_2OH$, —$O(CH_2OCH_3$.

In some embodiments $R^9$ is selected from the group consisting of hydrogen, halo, trifluoromethyl, difluoromethyl, $C_{1-6}$alkoxy, trifluoromethoxy, difluoromethoxy, hydroxyl, $C_{1-6}$alkyl, —$CH_2OH$, —$CH_2N(CH_3)_2$, —$O(CH_2)_2OH$, —$O(CH_2)_2OCH_3$; cyano, nitro, —COOH; preferably $R^9$ is hydrogen, halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$; preferably $R^9$ is hydrogen, halo, trifluoromethyl, difluoromethyl, $C_{1-3}$alkoxy, trifluoromethoxy, difluoromethoxy, hydroxyl, $C_{1-3}$alkyl, —$CH_2OH$, —$CH_2N(CH_3)_2$, —$O(CH_2)_2OH$, —$O(CH_2)_2OCH_3$; preferably $R^9$ is hydrogen, halo, trifluoromethyl, difluoromethyl, methoxy, trifluoromethoxy, difluoromethoxy, hydroxyl, methyl —$CH_2OH$, —$CH_2N(CH_3)_2$, —$O(CH_2)_2OH$, —$O(CH_2)_2OCH_3$.

In some embodiments $R^{10}$ is selected from the group consisting of hydrogen, $C_{1-6}$alkyl, $C_{3-8}$cycloalkyl; preferably $R^{10}$ is hydrogen, $C_{1-4}$alkyl, $C_{3-6}$cycloalkyl; preferably $R^{10}$ is hydrogen, $C_{1-3}$alkyl, $C_{5-6}$cycloalkyl.

In some embodiments $R^{11}$ is selected from the group consisting of hydrogen, $C_{1-6}$alkyl, $C_{3-8}$cycloalkyl; preferably $R^{11}$ is hydrogen, $C_{1-4}$alkyl, $C_{3-6}$cycloalkyl; preferably $R^{11}$ is hydrogen, $C_{1-3}$alkyl, $C_{5-6}$cycloalkyl.

In some embodiments $R^{12}$ is selected from the group consisting of hydrogen, $C_{1-6}$alkyl, $C_{3-8}$cycloalkyl; preferably $R^{12}$ is hydrogen, $C_{1-4}$alkyl, $C_{3-6}$cycloalkyl; preferably $R^{12}$ is hydrogen, $C_{1-3}$alkyl, $C_{5-6}$cycloalkyl.

In some embodiments $R^{13}$ is selected from the group consisting of hydrogen, $C_{1-6}$alkyl, $C_{3-8}$cycloalkyl; preferably $R^{13}$ is hydrogen, $C_{1-4}$alkyl, $C_{3-6}$cycloalkyl; preferably $R^{13}$ is hydrogen, $C_{1-3}$alkyl, $C_{5-6}$cycloalkyl.

In some embodiments each $Z^1$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH; preferably $Z^1$ is halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano; preferably $Z^1$ is halo, trifluoromethyl, difluoromethyl, $C_{1-6}$alkoxy, trifluoromethoxy, difluoromethoxy, hydroxyl, $C_{1-6}$alkyl, —$CH_2OH$, —$CH_2N(CH_3)_2$, —$O(CH_2)_2OH$, —$O(CH_2)_2OCH_3$, cyano; preferably $Z^1$ is halo, trifluoromethyl, difluoromethyl, methoxy, trifluoromethoxy, difluoromethoxy, hydroxyl, methyl, ethyl, propyl, —$CH_2OH$, —$CH_2N(CH_2)_2$, —$O(CH_2)_2OH$, —$O(CH_2)_2OCH_3$, cyano; preferably $Z^1$ is F, Cl, trifluoromethyl, difluoromethyl, methoxy, ethoxy, trifluoromethoxy, difluoromethoxy, hydroxyl, $C_{1-6}$alkyl, —$CH_2OH$, —$CH_2N(CH_3)_2$, —$O(CH_2)_2OH$, —$O(CH_2)_2OCH_3$, cyano.

In some embodiments each $Z^2$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH; preferably $Z^2$ is halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano; preferably $Z^2$ is halo, trifluoromethyl, difluoromethyl, $C_{1-6}$alkoxy, trifluoromethoxy, difluoromethoxy, hydroxyl, $C_{1-6}$alkyl, —$CH_2OH$, —$CH_2N(CH_3)_2$, —$O(CH_2)_2OH$, —$O(CH_2)_2OCH_3$, cyano; preferably $Z^2$ is halo, trifluoromethyl, difluoromethyl, methoxy, trifluoromethoxy, difluoromethoxy, hydroxyl, methyl, ethyl, propyl, —$CH_2OH$, —$CH_2N(CH_3)_2$, —$O(CH_2)_2OH$, —$O(CH_2)_2OCH_3$, cyano; preferably $Z^2$ is F, Cl, trifluoromethyl, difluoromethyl, methoxy, ethoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano.

In some embodiments each $Z^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH; preferably $Z^3$ is halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano; preferably $Z^3$ is halo, trifluoromethyl, difluoromethyl, $C_{1-3}$alkoxy, trifluoromethoxy, difluoromethoxy, hydroxyl, $C_{1-3}$alkyl, —$CH_2OH$, —$CH_2N(CH_3)_2$, —$O(CH_2)_2OH$, —$O(CH_2)_2OCH_3$, cyano; preferably $Z^3$ is halo, trifluoromethyl, difluoromethyl, methoxy, trifluoromethoxy, difluoromethoxy, hydroxyl, methyl, ethyl, propyl, —$CH_2OH$, —$CH_2N(CH_3)_2$, —$O(CH_2)_2OH$, —$O(CH_2)_2OCH_3$, cyano; preferably $Z^3$ is F, Cl, trifluoromethyl, difluoromethyl, methoxy, ethoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano.

In some embodiments each $Z^4$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH; preferably $Z^4$ is halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano; preferably $Z^4$ is halo, trifluoromethyl, difluoromethyl, $C_{1-3}$alkoxy, trifluoromethoxy, difluoromethoxy, hydroxyl, $C_{1-6}$alkyl, —$CH_2OH$, —$CH_2N(CH_3)_2$, —$O(CH_2)_2OH$, —$O(CH_2)_2OCH_3$, cyano; preferably $Z^4$ is halo, trifluoromethyl, difluoromethyl, methoxy, trifluoromethoxy, difluoromethoxy, hydroxyl, methyl, ethyl, propyl, —$CH_2OH$, —$CH_2N(CH_3)_2$, —$O(CH_2)_2OH$, —$O(CH_2)_2OCH_3$, cyano; preferably $Z^4$ is F, Cl, trifluoromethyl, difluoromethyl, methoxy, ethoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano.

In some embodiments each $Z^5$ is independently selected from the group consisting of halo, trifluoromethyl, difluoromethyl, $C_{1-6}$alkoxy, trifluoromethoxy, difluoromethoxy, hydroxyl, $C_{1-6}$alkyl, —$CH_2OH$, amino, —$N(CH_3)_2$, —$CH_2N(CH_3)_2$, —$O(CH_2)_2OH$, —$O(CH_2)_2OCH_3$, cyano, nitro, —COOH; preferably $Z^5$ is halo, trifluoromethyl, difluoromethyl, $C_{1-4}$alkoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano; preferably $Z^5$ is halo, trifluoromethyl, difluoromethyl, $C_{1-3}$alkoxy, trifluoromethoxy, difluoromethoxy, hydroxyl, $C_{1-3}$alkyl, —$CH_2OH$, —$CH_2N(CH_3)_2$, —$O(CH_2)_2OH$, —$O(CH_2)_2OCH_3$, cyano; preferably $Z^5$ is halo, trifluoromethyl, difluoromethyl, methoxy, trifluoromethoxy, difluoromethoxy, hydroxyl, methyl, ethyl, propyl, —$CH_2OH$, —$CH_2N(CH_3)_2$, —$O(CH_2)_2OH$, —$O(CH_2)_2OCH_3$, cyano; preferably $Z^5$ is F, Cl, trifluoromethyl, difluoromethyl, methoxy, ethoxy, trifluoromethoxy, difluoromethoxy, hydroxyl, $C_{1-4}$alkyl, —$CH_2OH$, —$CH_2N(CH_3)_2$, —$O(CH_2)_2OH$, —$O(CH_2)_2OCH_3$, cyano.

Particularly preferred compounds of the invention are those compounds of formula (IA), (IB) or (IC) listed in Tables 1, 2 and 3 hereafter.

TABLE 1

(IA)

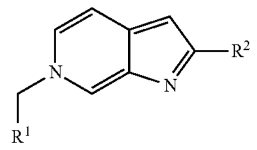

| Compound | $R^1$ | $R^2$ |
|---|---|---|
| I | 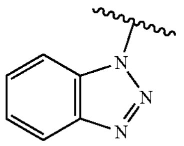 [SMILES: *n1nnc2ccccc21] | 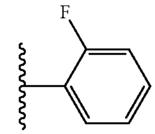 [SMILES: *c1ccccc1F] |
| II | | 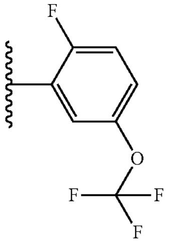 [SMILES: *c1cc(OC(F)(F)F)ccc1F] |
| III | | 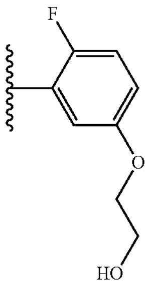 [SMILES: *c1cc(OCCO)ccc1F] |

TABLE 1-continued (IA)

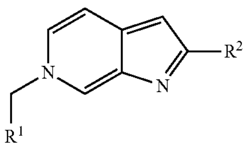

| Compound | $R^1$ | $R^2$ |
|---|---|---|
| IV | | 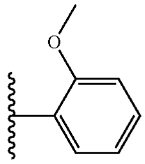 [SMILES: *c1ccccc1OC] |
| V | | 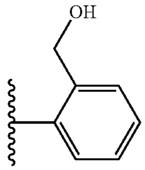 [SMILES: *c1ccccc1CO] |
| VI | | 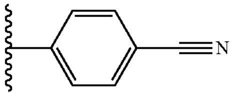 [SMILES: *c1ccc(C#N)cc1] |
| VII | | 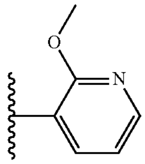 |
| VIII | | 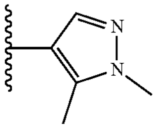 [SMILES: *c1cnn(C)c1C] |
| IX | 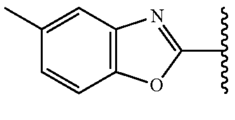 [SMILES: *c1nc2cc(C)ccc2o1] | 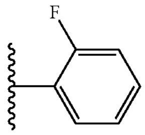 [SMILES: *c1ccccc1F] |
| X | | 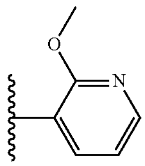 |
| XI | 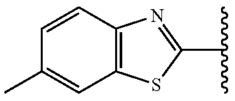 [SMILES: *c1nc2ccc(C)cc2s1] | 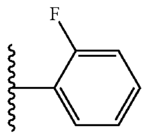 [SMILES: *c1ccccc1F] |

TABLE 1-continued
(IA)
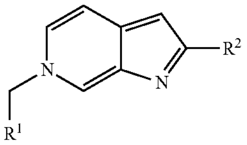
| Compound | $R^1$ | $R^2$ |
|---|---|---|
| XII | | 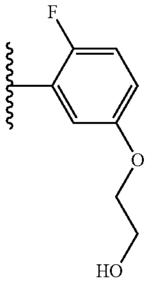 [SMILES: *c1cc(OCCO)ccc1F] |
| XIII | | 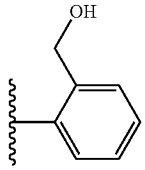 [SMILES: *c1ccccc1CO] |
| XIV | | 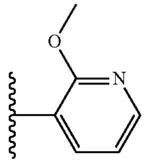 |
| XV | | 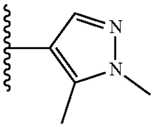 [SMILES: *c1cnn(C)c1C] |
| XVI | 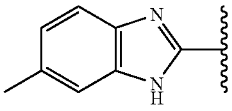 [SMILES: *c1nc2ccc(C)cc2[nH]1] | 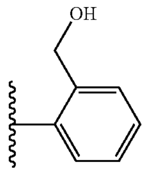 [SMILES: *c1ccccc1CO] |
TABLE 2
(IB)
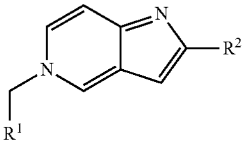
| Compound | $R^1$ | $R^2$ |
|---|---|---|
| XVII | 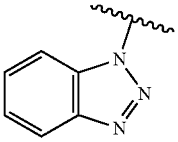 | 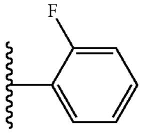 [SMILES: *c1ccccc1F] |
| XVIII | | 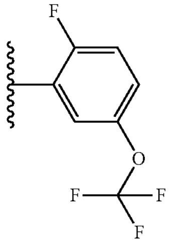 [SMILES: *c1cc(OC(F)(F)F)ccc1F] |
| XIX | | 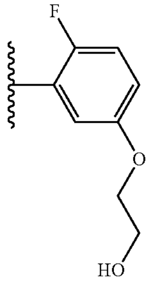 [SMILES: *c1cc(OCCO)ccc1F] |
| XX | | 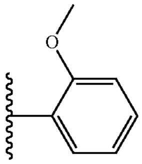 [SMILES: *c1ccccc1OC] |
| XXI | | 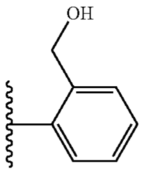 [SMILES: *c1ccccc1CO] |
| XXII | | 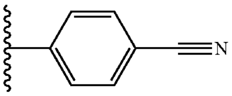 |
| XXIII | | 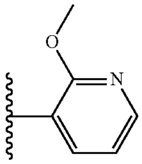 [SMILES: *c1cccnc1OC] |

TABLE 2-continued
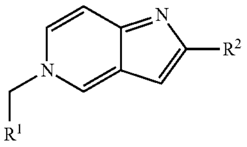
(IB)
| Compound | $R^1$ | $R^2$ |
|---|---|---|
| XXIV | | 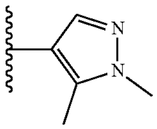 [SMILES: *c1cnn(C)c1C] |
| XXV | 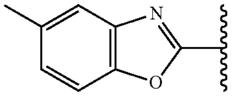 [SMILES: *c1nc2cc(C)ccc2o1] | 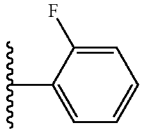 |
| XXVI | | 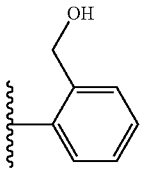 [SMILES: *c1ccccc1CO] |
| XXVII | | 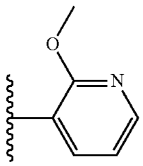 |
| XXVIII | 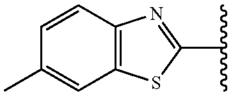 [SMILES: *c1nc2ccc(C)cc2s1] | 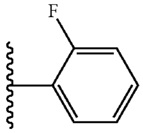 [SMILES: *c1ccccc1F] |
| XXIX | | 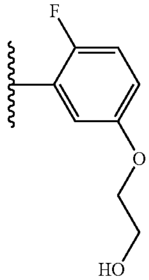 [SMILES: *c1cc(OCCO)ccc1F] |
| XXX | | 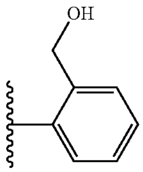 [SMILES: *c1ccccc1CO] |
TABLE 2-continued
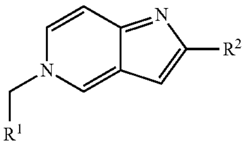
(IB)
| Compound | $R^1$ | $R^2$ |
|---|---|---|
| XXXI | | 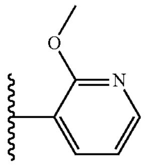 [SMILES: *c1cccnc1OC] |
| XXXII | | 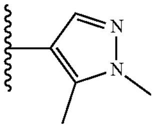 |
| XXXIII | 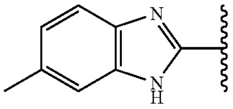 [SMILES: *c1nc2ccc(C)cc2[nH]1] | 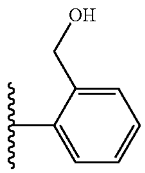 [SMILES: *c1ccccc1CO] |
| XXXIV | | 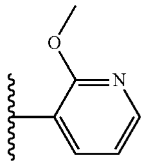 [SMILES: *c1cccnc1OC] |
TABLE 3
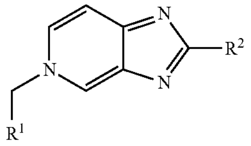
(IC)
| Compound | Structure |
|---|---|
| CPD-1 | 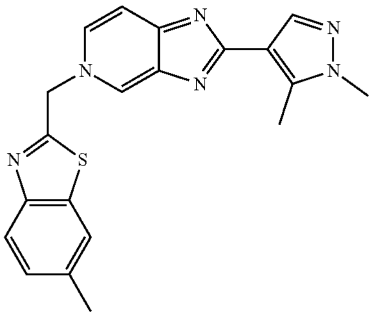 [SMILES: Cc1ccc2nc(Cn3ccc4nc(-c5cnn(C)c5C)nc-4c3)sc2c1] |

TABLE 3-continued
(IC)
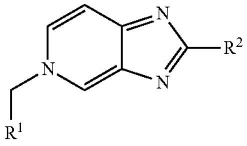
| Compound | Structure |
|---|---|
| CPD-2 | 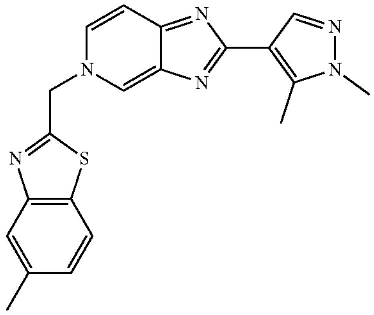 [SMILES: Cc1ccc2sc(Cn3ccc4nc(-c5cnn(C)c5C)nc-4c3)nc2c1] |
| CPD-3 | 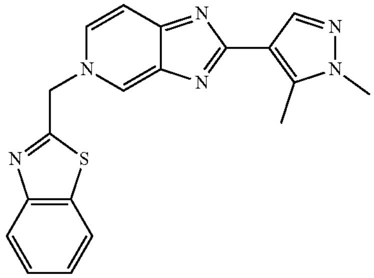 [SMILES: Cc1c(-c2nc3ccn(Cc4nc5ccccc5s4)cc-3n2)cnn1C] |
| CPD-4 | 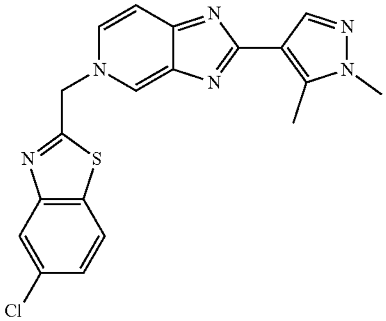 [SMILES: Cc1c(-c2nc3ccn(Cc4nc5cc(Cl)ccc5s4)cc-3n2)cnn1C] |
| CPD-5 | 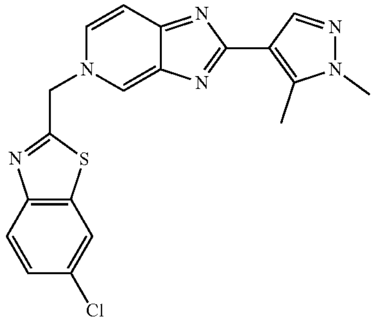 [SMILES: Cc1c(-c2nc3ccn(Cc4nc5ccc(Cl)cc5s4)cc-3n2)cnn1C] |
TABLE 3-continued
(IC)
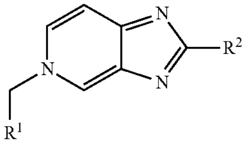
| Compound | Structure |
|---|---|
| CPD-6 | 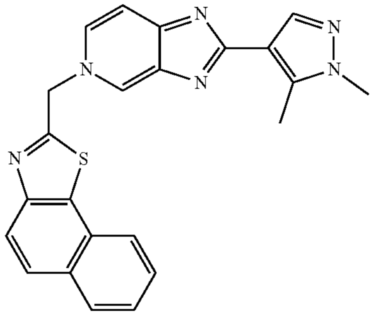 [SMILES: Cc1c(-c2nc3ccn(Cc4nc5ccc6ccccc6c5s4)cc-3n2)cnn1C] |
| CPD-7 | 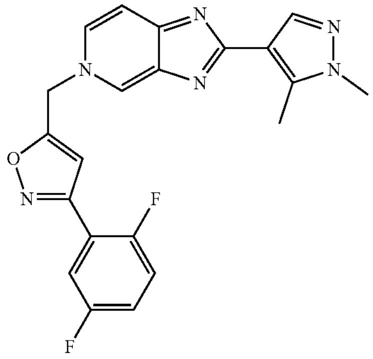 [SMILES: Cc1c(-c2nc3ccn(Cc4cc(-c5cc(F)ccc5F)no4)cc-3n2)cnn1C] |
| CPD-8 | 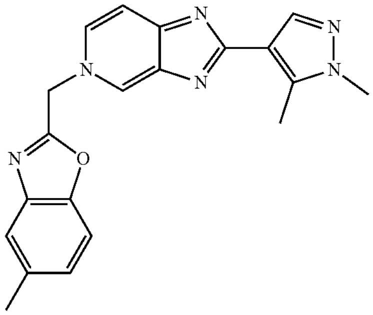 [SMILES: Cc1ccc2oc(Cn3ccc4nc(-c5cnn(C)c5C)nc-4c3)nc2c1] |
| CPD-9 | 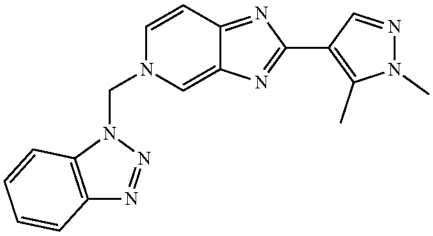 [SMILES: Cc1c(-c2nc3ccn(Cn4nnc5ccccc54)cc-3n2)cnn1C] |

TABLE 3-continued
(IC)
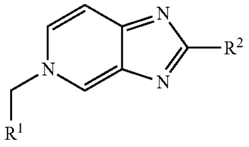
| Compound | Structure |
|---|---|
| CPD-10 | 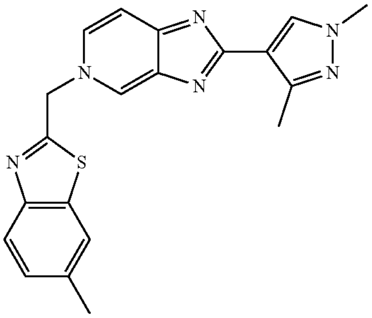 [SMILES: Cc1ccc2nc(Cn3ccc4nc(-c5cn(C)nc5C)nc-4c3)sc2c1] |
| CPD-11 | 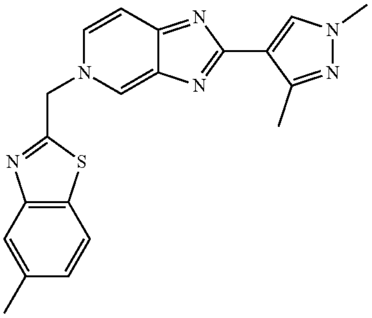 |
| CPD-12 | 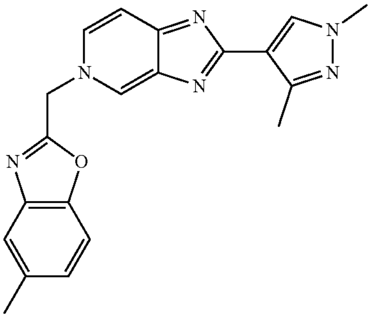 [SMILES: Cc1ccc2sc(Cn3ccc4nc(-c5cn(C)nc5C)nc-4c3)nc2c1] |
| CPD-13 | 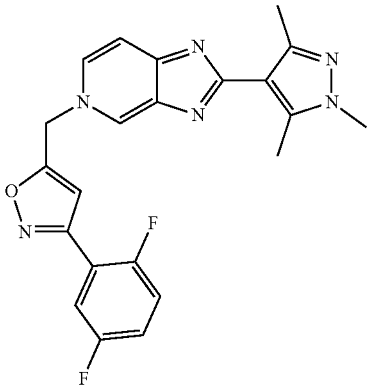 [SMILES: Cc1nn(C)c(C)c1-c1nc2ccn(Cc3cc(-c4cc(F)ccc4F)no3)cc-2n1] |
TABLE 3-continued
(IC)
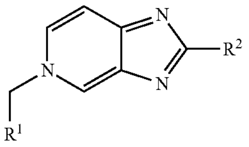
| Compound | Structure |
|---|---|
| CPD-14 | 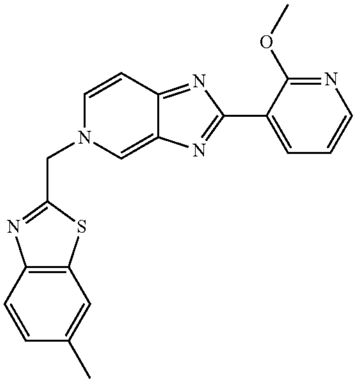 |
| CPD-15 | 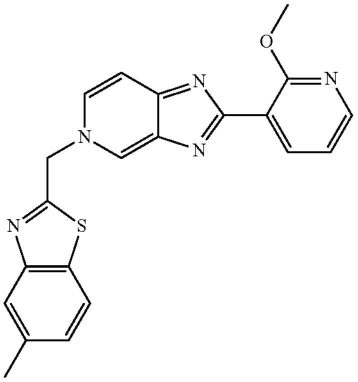 [SMILES: COc1ncccc1-c1nc2ccn(Cc3nc4cc(C)ccc4s3)cc-2n1] |
| CPD-16 | 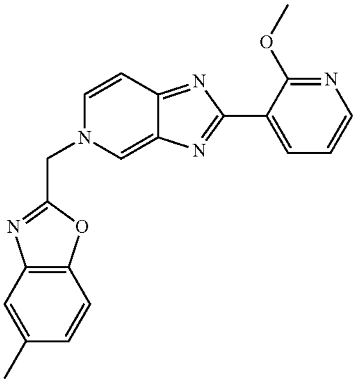 [SMILES: COc1ncccc1-c1nc2ccn(Cc3nc4cc(C)ccc4o3)cc-2n1] |

TABLE 3-continued
(IC)
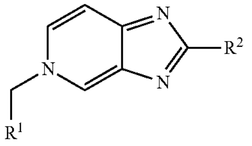
| Compound | Structure |
|---|---|
| CPD-17 | 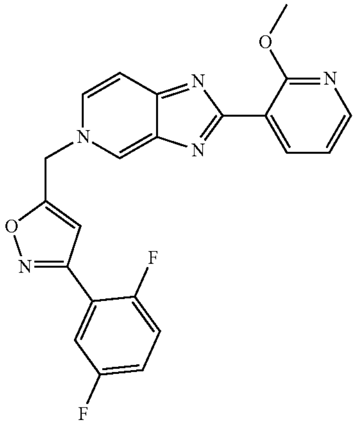 [SMILES: COc1ncccc1-c1nc2ccn(Cc3cc(-c4cc(F)ccc4F)no3)cc-2n1] |
| CPD-18 | 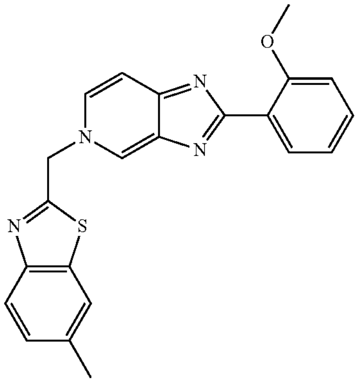 [SMILES: COc1ccccc1-c1nc2ccn(Cc3nc4ccc(C)cc4s3)cc-2n1] |
| CPD-19 | 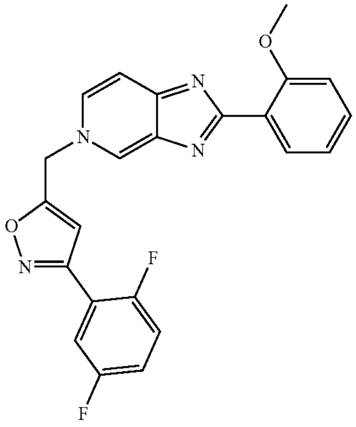 [SMILES: COc1ccccc1-c1nc2ccn(Cc3cc(-c4cc(F)ccc4F)no3)cc-2n1] |
TABLE 3-continued
(IC)
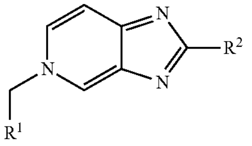
| Compound | Structure |
|---|---|
| CPD-20 | 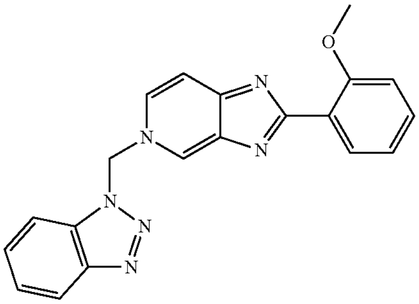 [SMILES: COc1ccccc1-c1nc2ccn(Cn3nnc4ccccc43)cc-2n1] |
| CPD-21 | 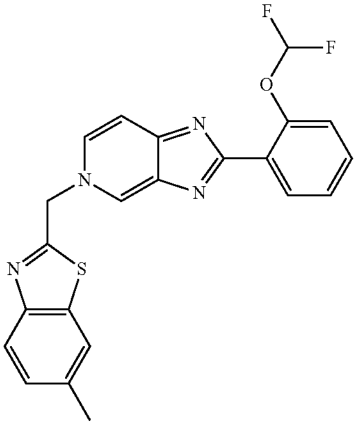 [SMILES: Cc1ccc2nc(Cn3ccc4nc(-c5ccccc5OC(F)F)nc-4c3)sc2c1] |
| CPD-22 | 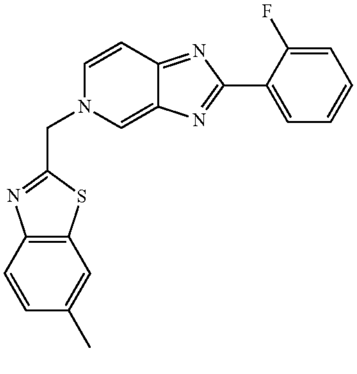 [SMILES: Cc1ccc2nc(Cn3ccc4nc(-c5ccccc5F)nc-4c3)sc2c1] |

TABLE 3-continued
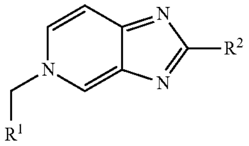
(IC)
| Compound | Structure |
|---|---|
| CPD-23 | 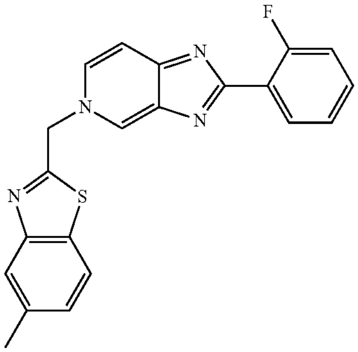 |
| CPD-24 | 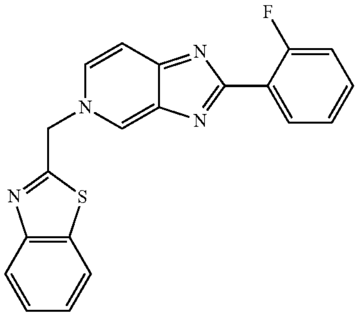 [SMILES: Fc1ccccc1-c1nc2ccn(Cc3nc4ccccc4s3)cc-2n1] |
| CPD-25 | 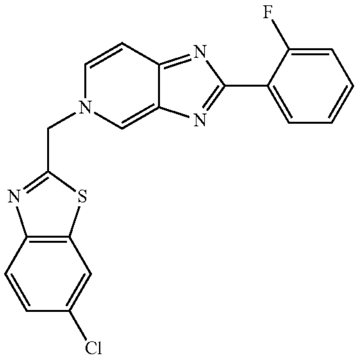 [SMILES: Fc1ccccc1-c1nc2ccn(Cc3nc4ccc(Cl)cc4s3)cc-2n1] |
| CPD-26 | 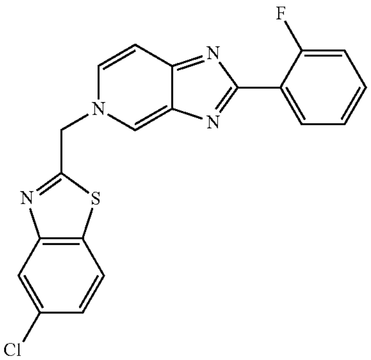 [SMILES: Fc1ccccc1-c1nc2ccn(Cc3nc4cc(Cl)ccc4s3)cc-2n1] |
TABLE 3-continued
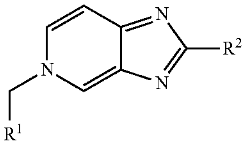
(IC)
| Compound | Structure |
|---|---|
| CPD-27 | 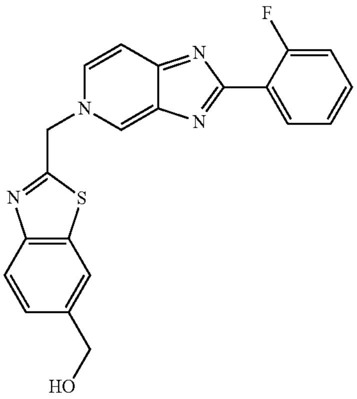 [SMILES: OCc1ccc2nc(Cn3ccc4nc(-c5ccccc5F)nc-4c3)sc2c1] |
| CPD-28 | 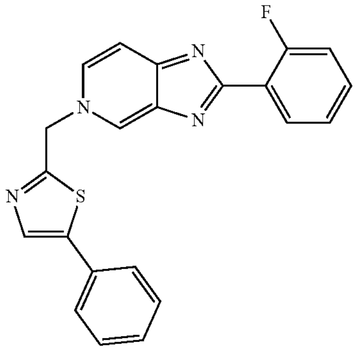 [SMILES: Fc1ccccc1-c1nc2ccn(Cc3ncc(-c4ccccc4)s3)cc-2n1] |
| CPD-29 | 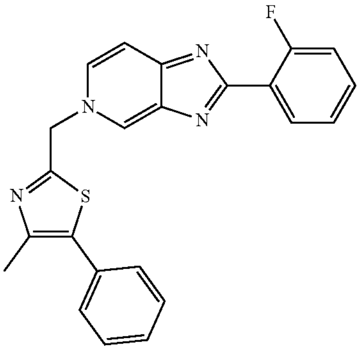 [SMILES: Cc1nc(Cn2ccc3nc(-c4ccccc4F)nc-3c2)sc1-c1ccccc1] |
| CPD-30 | 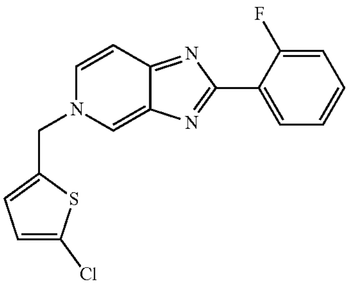 [SMILES: Fc1ccccc1-c1nc2ccn(Cc3ccc(Cl)s3)cc-2n1] |

TABLE 3-continued
(IC)
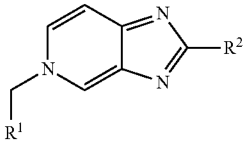
| Compound | Structure |
|---|---|
| CPD-31 | 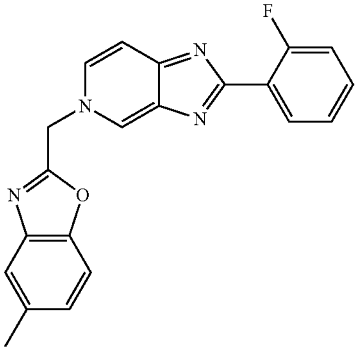 [SMILES: Cc1ccc2oc(Cn3ccc4nc(-c5ccccc5F)nc-4c3)nc2c1] |
| CPD-32 | 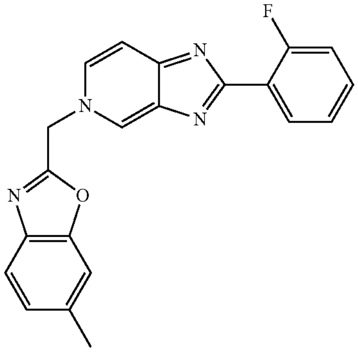 |
| CPD-33 | 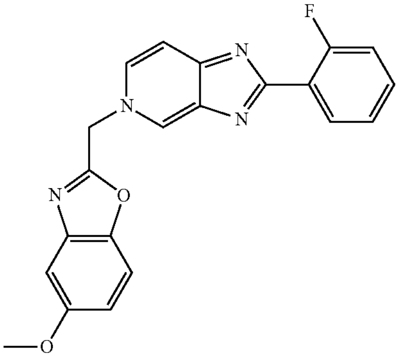 [SMILES: COc1ccc2oc(Cn3ccc4nc(-c5ccccc5F)nc-4c3)nc2c1] |
TABLE 3-continued
(IC)
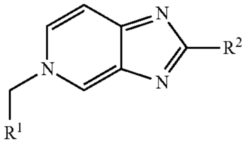
| Compound | Structure |
|---|---|
| CPD-34 | 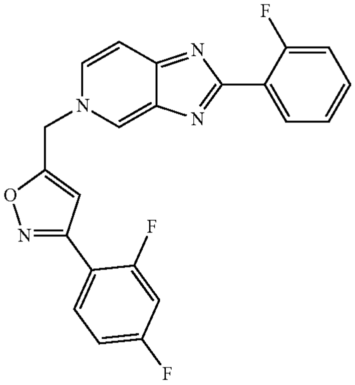 [SMILES: Fc1ccc(-c2cc(Cn3ccc4nc(-c5ccccc5F)nc-4c3)on2)c(F)c1] |
| CPD-35 | 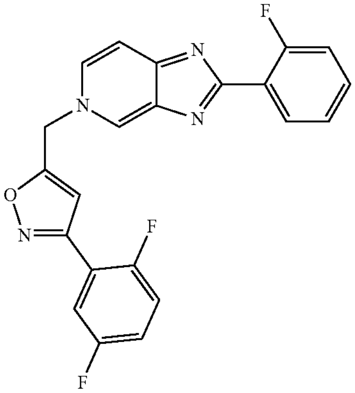 [SMILES: Fc1ccc(F)c(-c2cc(Cn3ccc4nc(-c5ccccc5F)nc-4c3)on2)c1] |
| CPD-36 | 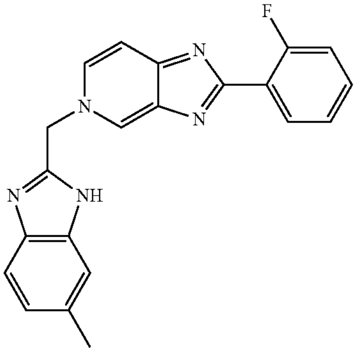 [SMILES: Cc1ccc2nc(Cn3ccc4nc(-c5ccccc5F)nc-4c3)[nH]c2c1] |

TABLE 3-continued
(IC)
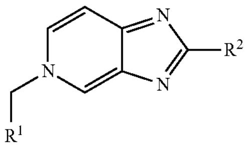
| Compound | Structure |
| --- | --- |
| CPD-37 | 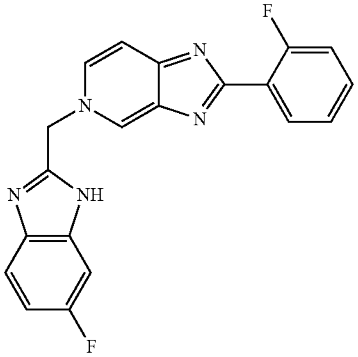 [SMILES: Fc1ccc2nc(Cn3ccc4nc(-c5ccccc5F)nc-4c3)[nH]c2c1] |
| CPD-38 | 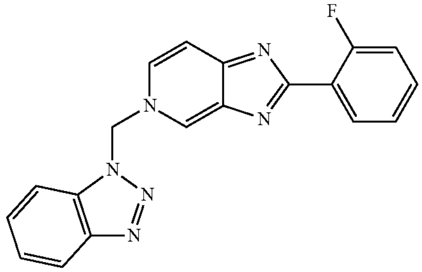 [SMILES: Fc1ccccc1-c1nc2ccn(Cn3nnc4ccccc43)cc-2n1] |
| CPD-39 | 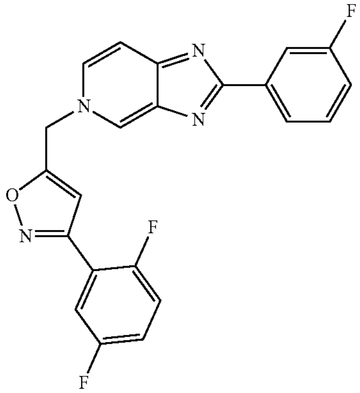 [SMILES: Fc1cccc(-c2nc3ccn(Cc4cc(-c5cc(F)ccc5F)no4)cc-3n2)c1] |
| CPD-40 | 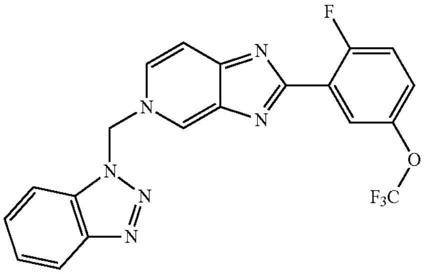 [SMILES: Fc1ccc(OC(F)(F)F)cc1-c1nc2ccn(Cn3nnc4ccccc43)cc-2n1] |
TABLE 3-continued
(IC)
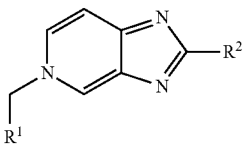
| Compound | Structure |
| --- | --- |
| CPD-41 | 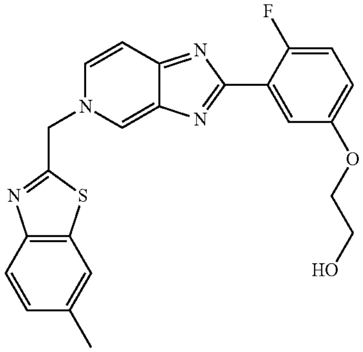 [SMILES: Cc1ccc2nc(Cn3ccc4nc(-c5cc(OCCO)ccc5F)nc-4c3)sc2c1] |
| CPD-42 | 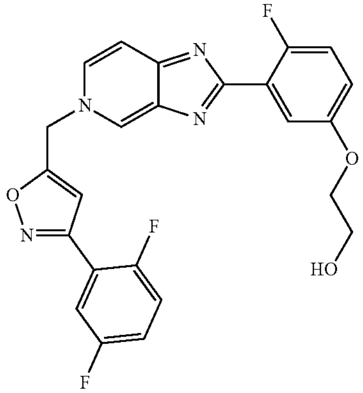 [SMILES: OCCOc1ccc(F)c(-c2nc3ccn(Cc4cc(-c5cc(F)ccc5F)no4)cc-3n2)c1] |
| CPD-43 | 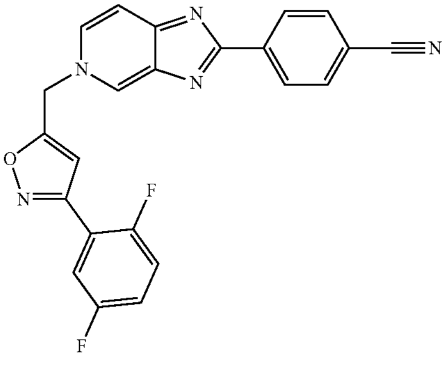 [SMILES: N#Cc1ccc(-c2nc3ccn(Cc4cc(-c5cc(F)ccc5F)no4)cc-3n2)cc1] |

TABLE 3-continued (IC)

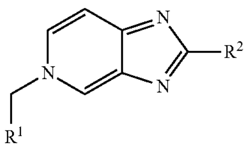

| Compound | Structure |
|---|---|
| CPD-44 | 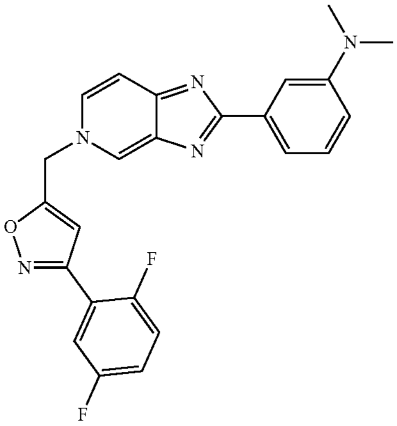 [SMILES: CN(C)c1cccc(-c2nc3ccn(Cc4cc(-c5cc(F)ccc5F)no4)cc-3n2)c1] |
| CPD-45 | 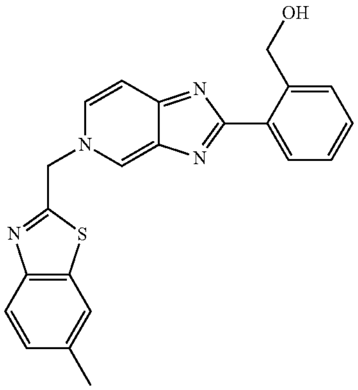 [SMILES: Cc1ccc2nc(Cn3ccc4nc(-c5ccccc5CO)nc-4c3)sc2c1] |
| CPD-46 | 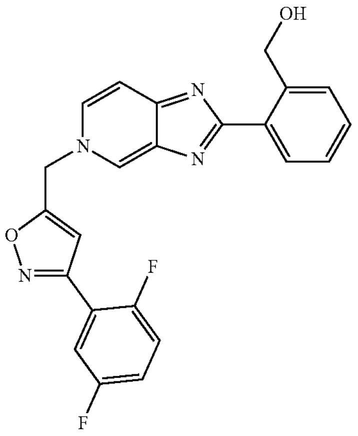 [SMILES: OCc1ccccc1-c1nc2ccn(Cc3cc(-c4cc(F)ccc4F)no3)cc-2n1] |

TABLE 3-continued (IC)

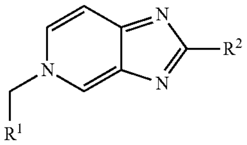

| Compound | Structure |
|---|---|
| CPD-47 | 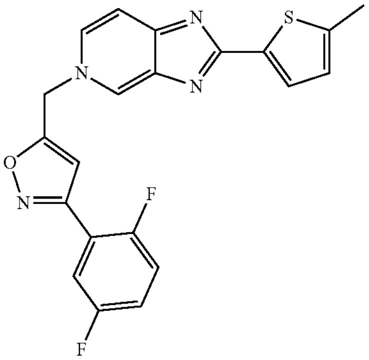 [SMILES: Cc1ccc(-c2nc3ccn(Cc4cc(-c5cc(F)ccc5F)no4)cc-3n2)s1] |
| CPD-48 | 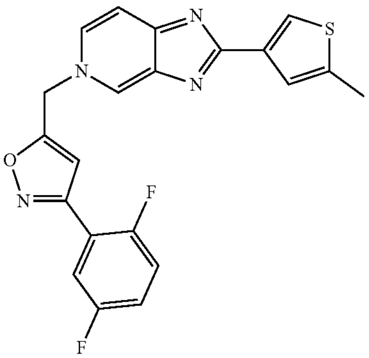 [SMILES: Cc1cc(-c2nc3ccn(Cc4cc(-c5cc(F)ccc5F)no4)cc-3n2)cs1] |
| CPD-49 | 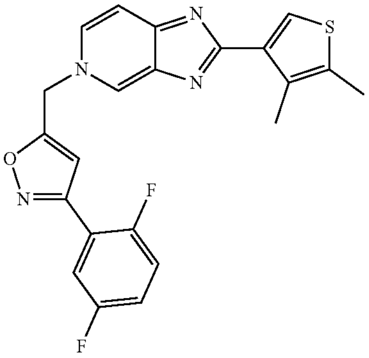 [SMILES: Cc1scc(-c2nc3ccn(Cc4cc(-c5cc(F)ccc5F)no4)cc-3n2)c1C] |

The compounds of the invention may be in the form of salts, preferably pharmaceutically acceptable salts, as generally described below. Some preferred, but non-limiting examples of suitable pharmaceutically acceptable organic and/or inorganic acids are as hydrochloric acid, hydrobromic acid, sulfuric acid, nitric acid, acetic acid and citric acid, as well as other pharmaceutically acceptable acids known per se (for which reference is made to the prior art referred to below).

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of the compounds of formula (I) and any subgroup thereof include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts.

Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Pharmaceutically acceptable salts of compounds of formula (I) may be prepared by one or more of these methods:
(i) by reacting the compound of formula (I) with the desired acid;
(ii) by reacting the compound of formula (I) with the desired base;
(iii) by removing an acid- or base-labile protecting group from a suitable precursor of the compound of formula (I) or by ring-opening a suitable cyclic precursor, for example, a lactone or lactam, using the desired acid; or
(iv) by converting one salt of the compound of formula (I) to another by reaction with an appropriate acid or by means of a suitable ion exchange column.

All these reactions are typically carried out in solution. The salt may precipitate from solution and be collected by filtration or may be recovered by evaporation of the solvent.

The degree of ionization in the salt may vary from completely ionized to almost non-ionized.

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Britain, Marcel Dekker, 1995), incorporated herein by reference. Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt Co-crystals may be prepared by melt crystallization, by recrystallization from solvents, or by physically grinding the components together—see Chem Commun, 17, 1889-1896, by O. Almarsson and M. J. Zaworotko (2004), incorporated herein by reference. For a general review of multi-component complexes, see J Pharm Sci, 64 (8), 1269-1288, by Haleblian (August 1975), incorporated herein by reference.

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as $—COO^-Na^+$, $—COO^-K^+$, or $—SO_3^-Na^+$) or non-ionic (such as $—N^- N^+(CH_3)_3$) polar head group. For more information, see Crystals and the Polarizing Microscope by N. H. Hartshorne and A. Stuart, 4$^{th}$ Edition (Edward Arnold, 1970), incorporated herein by reference.

All references to compounds of formula (I) or any subgroups thereof include references to salts, solvates, multi-component complexes and liquid crystals thereof and to solvates, multi-component complexes and liquid crystals of salts thereof.

The compounds of the invention include compounds of formula (I) or any subgroups thereof as hereinbefore defined, including all polymorphs and crystal habits thereof, prodrugs and isomers thereof (including optical, geometric and tautomeric isomers) as hereinafter defined and isotopically-labeled compounds of formula (I).

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention.

The compounds of formula (I) or any subgroups thereof may be prepared as described in the experimental section below using methods and chemistries with which those skilled in the art shall be familiar.

The present invention also encompasses pharmaceutical composition comprising at least one compound of the present invention. The present invention also encompasses pharmaceutical composition comprising at least one compound of the invention and at least one carrier, excipient or diluent acceptable for pharmaceutical purposes.

In some embodiments the present invention relates to the use of at least one compound of formula (I), or any subgroups thereof, in (the preparation of a composition for) the prevention and/or treatment of an infection caused by pestivirus in an animal; preferably a mammal; more preferably a bovine, a pig, a sheep, or a goat. In particular embodiments the compounds of the invention are for use in the treatment of one or more symptoms and/or pathogenical manifestations of pestivirus infection as described herein and/or are for use in the prevention of such symptoms and/or pathogenical manifestations in animals suspected to have been in contact with an infected animal. In a particular embodiment pestivirus infection is an infection caused by bovine viral diarrhea virus, classical swine fever virus, border disease virus, atypical porcine pestivirus, or HoBi-like virus.

The international taxonomy of pestiviruses has changed to include 11 species (pestivirus A, B, C, D, E, F, G H, I, J and K) (Smith at al. 2017, J Gen Virol. 98(8):2106-2112). The species names are changed to Bovine viral diarrhea 1 (BVDV1)=pestivirus A, Bovine viral diarrhea 2 (BVDV2) =pestivirus B, Classical swine fever virus (CSFV)=pestivirus C, and Border disease virus (BDV)=pestivirus D. There are also 4 new species for which the example isolates are as follows: Pestvirus E (pronghorn pestivirus), Pestivirus F (Bungowannah virus), Pestvirus G (giraffe pestivirus), Pestvirus H (Hobi-like pestivirus), Pestivirus I (Aydin-like pestivirus), Pestvirus J (rat pestivirus) and Pestivirus K (atypical porcine pestivirus).

Accordingly, in a particular embodiment a pestivirus infection is an infection caused by one or more of a species from pestivirus A, pestivirus B, pestivirus C, pestivirus D, pestivirus H and/or pestivirus K.

In some embodiments the present invention relates to a method of prevention and/or of treatment of an infection caused by pestivirus, comprising administering to a subject in need thereof an effective amount of at least one compound of formula (I), or any subgroups thereof, or a pharmaceutical composition comprising said at least one compound of formula (I) or any subgroups thereof; wherein said subject is an animal; preferably a mammal; more preferably a bovine, a pig, a sheep, or a goat. In a particular embodiment pestivirus infection is an infection caused by bovine viral diarrhea virus, classical swine fever virus, border disease virus, atypical porcine pestivirus, or HoBi-like virus.

In some embodiments the present invention relates to the use of at least one compound of formula (I), or any subgroups thereof, in (the preparation of a composition for) the prevention and/or treatment of an infection caused by pestivirus in an animal; preferably a mammal; more preferably a bovine, a pig, a sheep, or a goat. In a particular embodiment pestivirus infection is an infection caused by bovine viral diarrhea virus, classical swine fever virus, border disease virus, atypical porcine pestivirus, or HoBi-like virus.

The term "subject" as used herein refers to an animal; more preferably a mammal. More preferably, the subject will be a domestic livestock, laboratory or pet animals. In some embodiments the domestic livestock is a bovine.

As used herein, the term "effective amount" means that amount of a drug or pharmaceutical agent that will elicit the biological or medical response of a tissue, system, animal, or human that is being sought, for instance, by a researcher or clinician.

The term therapeutically "effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The compounds of the present invention are of interest for use in the prevention and/or treatment of infection caused by pestivirus. In some embodiments pestivirus infection is an infection caused by bovine viral diarrhea virus (BVDV), classical swine fever virus, border disease virus, atypical porcine pestivirus, or HoBi-like virus. BVDV is a pathogen associated with gastrointestinal, respiratory, and reproductive diseases. The symptoms of infection are decreased fertility and milk production, slow fetal growth, diarrhea, respiratory symptoms, reproductive dysfunctions such as abortion, teratogenesis, embryonic resorption, fetal mummification and stillbirth, immuno-logical dysfunctions, concurrent infections, impaired herd performance. More particularly, one or more symptoms indicative of BVDV infection may include fever, leukopenia and viremia, lethargy, anorexia, mild oculonasal discharge, diarrhea, mild oral erosions and ulcers. Accordingly, the compounds of the invention are also envisaged for use in the prevention and/or treatment of one or more symptoms of infection by pestivirus. In some embodiments pestivirus infection is an infection caused by bovine viral diarrhea virus (BVDV), classical swine fever virus, border disease virus, atypical porcine pestivirus, or HoBi-like virus. In particular embodiments the compounds of the invention for use in the prevention of infection with pestivirus or the prevention of symptoms caused by pestivirus infection is administered to an animal which is known to have had, or is at risk of or suspected of having had contact with a persistently infected animal. In some embodiments pestivirus infection is an infection caused by bovine viral diarrhea virus (BVDV), classical swine fever virus, border disease virus, atypical porcine pestivirus, or HoBi-like virus. In particular embodiments the animal is an animal that has (potentially) been exposed to contaminated nasal or oral secretions, contaminated feces or urine, contaminated semen, a contaminated environment, contaminated fomite(s), contaminated modified live vaccines, or has been subjected to embryo transfer from a contaminated animal or is/was in contact with an infected mother in the womb.

For use in therapy, therapeutically effective amounts of a compound of formula (I), as well as tautomers, salts, hydrates or solvates thereof, may be administered as the raw chemical. Additionally, the active ingredient may be presented as a pharmaceutical composition.

Accordingly, the invention further provides pharmaceutical compositions that include effective amounts of compounds of formula (I), or stereoisomers, or tautomers, salts, hydrates, solvates, or prodrugs thereof, and one or more pharmaceutically acceptable carriers, diluents, or excipients. The compounds of formula (I) or stereoisomers, or tautomers, salts, hydrates or solvates thereof, are as herein described.

The compounds according to the invention may be administered as the sole active ingredient or together, i.e. in a fixed or free combination, with other therapeutic agents used in clinical practice for the treatment of those diseases listed hereinabove.

The compounds according to the invention and the other pharmaceutical active agent(s) may be administered together or separately and, when administered separately, administration may occur simultaneously or sequentially, in any order. The amounts of the compounds according to the invention and the other pharmaceutically active agent(s) and the relative timings of administration will be selected in order to achieve the desired combined therapeutic effect. The administration in combination of a compound of formula (I) or a stereoisomer, or a tautomer, salt, hydrate solvate or prodrugs thereof, with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a prodrug or predrug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. Nos. 8,372,778, 6,369,086, 6,369,087 and 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for parenteral administration (such as by intravenous, intramuscular, subcutaneous, intradermal or transdermal injection or intravenous infusion) or oral administration. Such suitable administration forms—which may be semi-solid or liquid, —as well as methods and carriers, diluents and excipients for use in the preparation thereof, will be clear to the skilled person; reference is again made to for instance U.S. Pat. Nos. 6,372,778, 6,369,086, 6,369,087 and 6,372,733, as well as to the standard handbooks, such as the latest edition of Remington's Pharmaceutical Sciences.

Some preferred, but non-limiting examples of such preparations include suspensions, emulsions, solutions, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as emulsifying and suspending agents, dispersing agents, preserving agents, release agents, etc. The compositions may also be formulated so as to provide rapid, controlled, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ α-, β- or γ-cyclodextrins or their derivatives. In addition, co-solvents such as alcohols may improve the solubility and/or the stability of the compounds. In the preparation of aqueous compositions, addition of salts of the compounds of the invention can be more suitable due to their increased water solubility.

Appropriate cyclodextrins are α-, β- or γ-cyclodextrins (CDs) or ethers and mixed ethers thereof wherein one or more of the hydroxyl groups of the anhydroglucose units of the cyclodextrin are substituted with alkyl, particularly methyl, ethyl or isopropyl, e.g. randomly methylated β-CD; hydroxyalkyl, particularly hydroxyethyl, hydroxypropyl or hydroxybutyl; carboxyalkyl, particularly carboxymethyl or carboxyethyl; alkylcarbonyl, particularly acetyl; alkoxycarbonylalkyl or carboxyalkoxyalkyl, particularly carboxymethoxypropyl or carboxyethoxypropyl; alkylcarbonyloxyalkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD). The term mixed ether denotes cyclodextrin derivatives wherein at least two cyclodextrin hydroxyl groups are etherified with different groups such as, for example, hydroxypropyl and hydroxyethyl. In particular, the present invention encompasses a pharmaceutical composition comprising an effective amount of a compound according to the invention with a pharmaceutically acceptable cyclodextrin. The present invention also encompasses cyclodextrin complexes consisting of a compound according to the invention and a cyclodextrin.

The preparations may be prepared in a manner known per se, which usually involves mixing the at least one compound according to the invention with the one or more pharmaceutically acceptable carriers, and, if desired, in combination with other pharmaceutical active compounds, when necessary under aseptic conditions. Reference is again made to U.S. Pat. Nos. 6,372,778, 6,369,086, 6,389,087 and 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, vial, bottle, sachet, ampoule or in any other suitable single-dose or multi-dose holder or container (which may be property labeled); optionally with one or more leaflets containing product information and/or instructions for use. Generally, such unit dosages will contain between 1 and 100000 mg, and usually between 5 and 50000 mg, of the at least one compound of the invention, e.g. about 1000, 2500, 5000, 10000, 20000, 30000 or 40000 mg per unit dosage The at least one compound of the invention will generally be administered in an "effective amount", by which is meant any amount of a compound of the formula (I) above that, upon suitable administration, is sufficient to achieve the desired therapeutic or prophylactic effect in the subject to which it is administered. Usually, depending on the condition to be prevented or treated and the route of administration, such an effective amount will usually be between 0.01 to 100 mg per kilogram, more often between 0.1 and 50 mg, such as between 1 and 25 mg, for example about 0.5, 1.0, 2.0, 5.0, 10.0, 15.0, 20.0, 25.0, 50.0 mg, per kilogram body weight day of the patient per day, which may be administered as a single daily dose, divided over one or more daily doses, or essentially continuously, e.g. using a drip infusion, or in a rapid, controlled, sustained or delayed release way. In particular embodiments the daily dosage is administered for 2, 3, 4, 5, 6, 7, 8, 9, 10, 11, 12, 13, 14 or more days, such as for seven days. In particular embodiments, the daily dosage is stopped if there are no longer any clinical symptoms. In particular embodiments, the treatment is stopped after 2, 3, 4, 5, 6, 7, 8, 9, 10, 11, 12, 13, 14 or more days, if there is no longer sign of any clinical symptoms. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. Nos. 8,372,778, 6,369,086, 6,369,087 and 8,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For administration, such as oral, subcutaneous, intravenous or parenteral administration, the compound according to the invention may be combined, if desired with the substances customary therefore such as solubilizers, emulsifiers or further auxiliaries and are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid The compositions are of particular value in the veterinary field, which for the purposes herein not only includes the prevention and/or treatment of diseases in animals, but also—for economically important animals such as livestock, and in particular bovines, pigs, sheep, or goats. —enhancing the growth and/or weight of the animal and/or the amount and/or the quality of the meat or other products obtained from the animal. Thus, in a further aspect, the invention relates to a (pharmaceutical) composition for veterinary use that contains at least one compound of the invention and at least one suitable carrier (i.e. a carrier suitable for veterinary use). The invention also relates to the use of a compound of the invention in the preparation of such a composition.

EXAMPLES

The following examples are provided for the purpose of illustrating the present invention and by no means should be interpreted to limit the scope of the present invention.

Example 1. Synthesis of Compounds I, IX and XI

Preparation of 2-(2-fluorophenyl)-1H-pyrrolo[2,3-c]pyridine 4, Common Intermediate

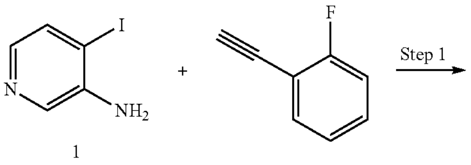

1

2

-continued

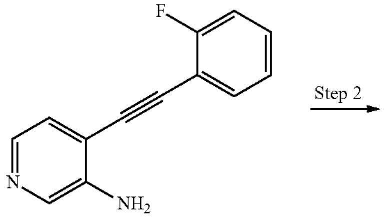

2

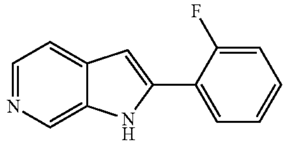

4

Step 1

To the stirred solution of 4-iodopyridin-3-amine (2.0 g, 1 eq.) in triethylamine (20 mL, 10 V) was added 1-ethynyl-2-fluorobenzene (1.67 g, 1.2 eq.). The resulting brown solution was purged with argon during 15 min. Then copper (I) iodide (0.022 g, 0.01 eq.) was added. After 10 min stirring, bis(triphenylphosphine)palladium(II) dichloride (0.082 g, 0.01 eq.) was added under inert atmosphere. The resulting black solution was stirred at 90° C. for 12 h. The reaction mixture was diluted with dichloromethane (DCM) (10 V) and filtered through a celite pad. Filtrate was concentrated and the obtained crude was purified by column chromatography using ethyl acetate and hexane as mobile phase to get 4-[(2-fluorophenyl)ethynyl]pyridin-3-amine 3 as a brown solid (2.0 g, 83%).

Step 2

To the stirred solution of 4-[(2-fluorophenyl)ethynyl] pyridin-3-amine 3 (22 g, 1.0 eq.) in 1,4-dioxane (225 mL, 10 V) was added potassium tert-butoxide (23.75 g, 2.0 eq.). The resulting black solution was stirred at 85° C. for 2 h. The reaction mixture was diluted with dichloromethane (10 V) and filtered through a celite pad. Celite plug was washed with DCM (5 V×2). Combined organic layer was washed with saturated ammonium chloride solution (10 V) followed by brine. Organic layer was dried over anhydrous $Na_2SO_4$ and concentrated to yield a brown gummy solid. Crude compound was purified by flash column chromatography using ethyl acetate and hexane as mobile phase to get 2-(2-fluorophenyl)-1H-pyrrolo[2,3-c]pyridine 4 as a brown solid (15 g, 68%).

$^1$H NMR (400 MHz, DMSO-d6) δ ppm: 12.0 (s, 1H), 8.82 (s, 1H), 8.12 (d, 1H), 7.98 (t, 1H), 7.60 (d, 1H), 7.50 (m, 1H), 7.35 (m, 2H), 6.95 (s, 1H).

ES+MS m/z: 213 (M+1).

Synthesis of 1-{[2-(2-fluorophenyl)-6H-pyrrolo[2,3-c]pyridin-6-yl]methyl}-1H-benzotriazole (Compound I)

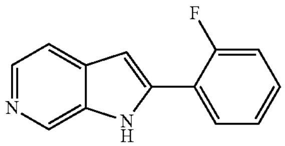

4

+

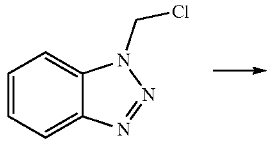

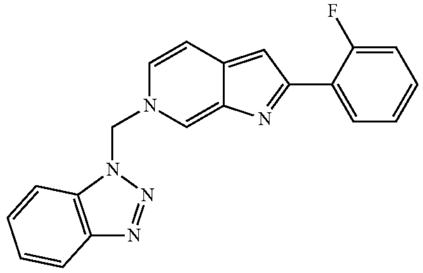

I

To the suspension of 2-(2-fluorophenyl)-1H-pyrrolo[2,3-c]pyridine 4 (0.250 g, 1.0 eq.) in DIPEA (1.25 mL, 5V) was added a solution of 1-(chloromethyl)-1H-benzotriazole (0.229 g, 1.2 eq.) in dimethylformamide (DMF) (1.25 mL, 5V) at ambient temperature over a period of 5 min. The reaction mixture was stirred during 1 h to yield a clear brown solution. After additional 5 h stirring at ambient temperature the clear brown solution turned to a pale yellow suspension. Reaction was monitored by TLC ($CH_2Cl_2$:MeOH, 9:1). Upon complete consumption of starting material, the obtained precipitate was collected by filtration and washed with dichloromethane (10 V). Subsequent drying under reduced pressure at 50° C. yielded 1-{[2-(2-fluorophenyl)-6H-pyrrolo[2,3-c]pyridin-6-yl]methyl}-1H-benzotriazole CI) as yellow solid (0.150 g, 35.8%).

$^1$H NMR (400 MHz, DMSO-d6) δ ppm: 9.10 (s, 1H), 8.38-8.33 (t, 1H), 8.31 (d, J=8.4 Hz, 1H), 8.12 (d, J=8.4 Hz, 1H), 7.98-7.94 (d, J=6.8 Hz, 1H), 7.71 (t, 1H), 7.63 (d, 6.8 Hz, 1H), 7.49 (t, 1H), 7.39 (m, 3H), 7.38-7.24 (m, 2H), 7.01 (d, J=4.8 Hz, 1H).

ES+MS m/z: 344.5 (M+1).

Preparation of 2-{[2-(2-fluorophenyl)-6H-pyrrolo[2,3-c]pyridin-6-yl]methyl}-5-methyl-1,3-benzoxazole (Compound IX)

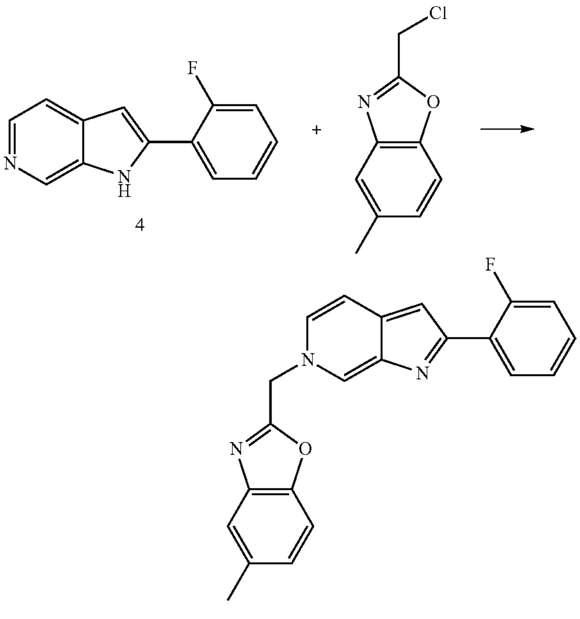

4

IX

To a solution of 2-(2-fluorophenyl)-1H-pyrrolo[2,3-c]pyridine 4 (0.250 g, 1.0 eq.) in DMF (5 mL, 20 V) was added NaOH (42 mg, 0.9 eq., 30% solution) and DIPEA (0.540 mL, 2.5 eq.) at 0° C. After 10 min stirring, 2-(chloromethyl)-5-methyl-1,3-benzoxazole (0.234 g, 1.1 eq.) was added. The resulting brown solution was gradually warmed to ambient temperature and stirred for another 12 h. The reaction mixture was diluted with ethyl acetate (15 V) and washed with water (2 V). The organic layer was separated, dried over $Na_2SO_4$ and concentrated under reduced pressure. The crude was purified by column chromatography using ethyl acetate and hexane as mobile phase to get 2-{[2-(2-fluorophenyl)-6H-pyrrolo[2,3-c]pyridin-6-yl]methyl}-5-methyl-1,3-benzoxazole (Compound IX) (200 mg, 47%) as an off white solid.

$^1$H NMR (400 MHz, DMSO-d6) δ ppm: 8.88 (s, 1H), 8.40 (t, 1H), 7.82 (d, J=6 Hz, 1H), 7.67-7.63 (m, 2H), 7.51 (s, 1H), 7.40 (m, 1H), 7.25-7.23 (m, 3H), 7.06 (d, J=4.8 Hz, 1H), 6.03 (s, 2H), 2.39 (s, 3H).

ES+MS m/z: 358.5 (M+1).

Preparation of 2-{[2-(2-fluorophenyl)-6H-pyrrolo[2,3-c]pyridin-6-yl]methyl}-6-methyl-1,3-benzothiazole (Compound XI)

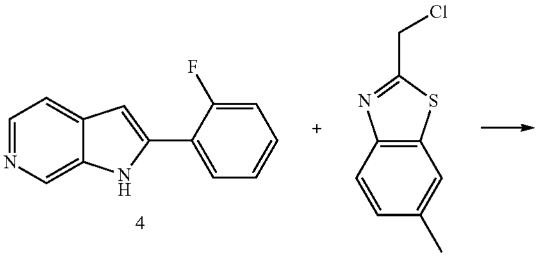

4

-continued

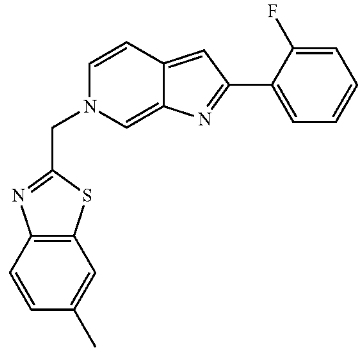

XI

To a stirred solution of 2-(2-fluorophenyl)-1H-pyrrolo[2,3-c]pyridine 4 (0.200 g, 1.0 eq.) in DMF (2.8 mL, 14 V) was added NaOH (33 mg, 0.9 eq., 30% solution) followed by DIPEA (0.409 mL, 2.5 eq.) at 0° C. After 10 min stirring, 2-(chloromethyl)-6-methyl-1,3-benzothiazole (0.204 g, 1.1 eq.) was added. The resulting brown solution was gradually warmed to ambient temperature and stirred for another 12 h. The reaction mixture was diluted with dichloromethane (10 V) and washed with water (2 V). The organic layer was separated, dried over $Na_2SO_4$ and concentrated under reduced pressure. The crude was purified by column chromatography using ethyl acetate and hexane as mobile phase to get 2-{[2-(2-fluorophenyl)-6H-pyrrolo[2,3-c]pyridin-6-yl]methyl}-6-methyl-1,3-benzothiazole (Compound XI) as a pale yellow solid (70 mg, 19%).

$^1$H NMR (400 MHz, DMSO-d6) δ ppm: 8.95 (s, 1H), 8.40 (t, 1H), 7.84-7.83 (m, 3H), 7.67 (d, J=6.8 Hz, 1H), 7.45-7.20 (m, 4H), 7.05 (d, J=4.4 Hz, 1H), 6.10 (s, 2H), 2.42 (S, 3H).

ES+MS m/z: 374.7 (M+1).

Example 2. Synthesis of Compound II

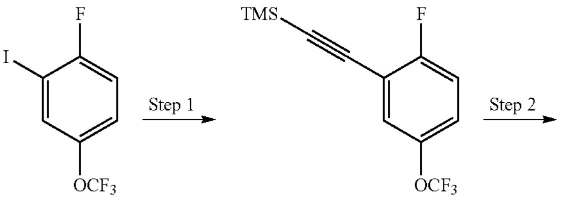

1

2

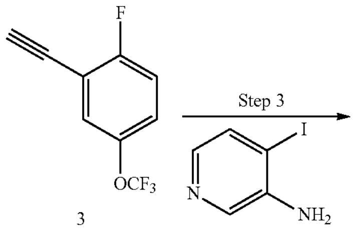

3

-continued

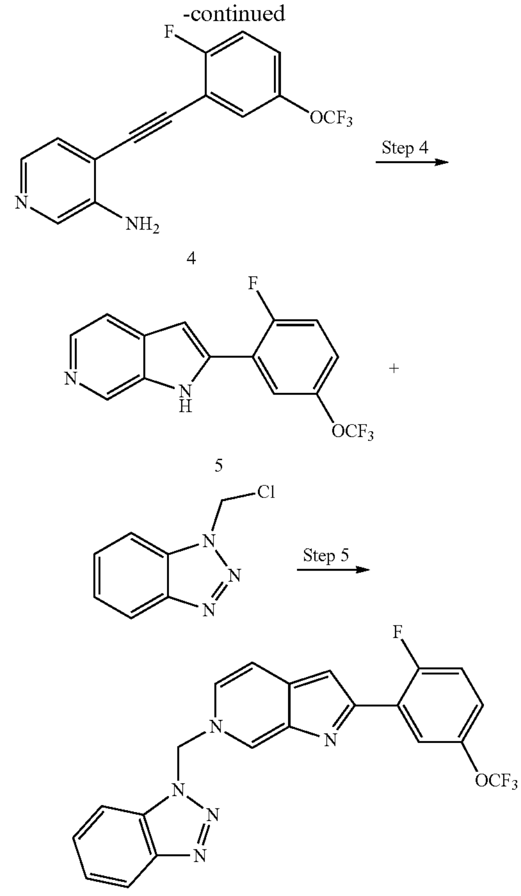

4

5

II

Step 1

The stirred solution of 1-fluoro-2-iodo-4-(trifluoromethoxy)benzene (1.0 g, 1.0 eq.) and TMS-Acetylene (0.698 mL, 1.5 eq.) in triethylamine (10 mL, 10 V) was purged with argon during 10 min. Copper(I) iodide (55 mg, 0.09 eq.) followed by bis(triphenylphosphine)palladium(II) dichloride (45 mg, 0.02 eq.) were added under inert atmosphere. The resulting solution was stirred at 100° C. for 2 h. Then the volatiles were evaporated, the remaining mass was diluted with ethyl acetate (100 mL) and filtered through celite pad. The filtrate was washed with water (50 mL×2), dried over $Na_2SO_4$ and evaporated under reduced pressure. The crude product was purified by silica gel column chromatography using ethyl acetate and hexane as mobile phase to get intermediate 2 (0.723 g with 80%).

Step 2

Intermediate 2 (0.720 g) was dissolved in methanol (7.2 ml, 10 V) under inert atmosphere. Then $K_2CO_3$ (0.719 g, 2.0 eq.) was added and the resulting mixture was stirred for 12 h.

Reaction was monitored by TLC. Once the starting disappeared, methanol was evaporated under reduced pressure. The crude was diluted with water and extracted with ethyl acetate. Organic layer was separated, washed with brine, died over $Na_2SO_4$ and concentrated to get the 2-ethynyl-1-fluoro-4-(trifluoromethoxy)benzene 3 (452 mg, 85%). The product was used for the next step without any further purification.

Step 3

The stirred solution of 2-ethynyl-1-fluoro-4-(trifluoromethoxy)benzene 3 (0.450 g, 1.0 eq.), 4-iodopyridin-3-amine (0.483 g, 1.0 eq.) and triethylamine (0.612 mL, 2 eq.) in THF (9.6 ml, 20 V) was purged with argon during 10 min. To the above solution, copper(I) iodide (20 mg, 0.05 eq.) and bis(triphenylphosphine)palladium(II) dichloride (154 mg, 0.1 eq.) were added subsequently. The resulting solution was stirred at ambient temperature for 12 h. Then, the volatiles were evaporated, the remaining mass was diluted with ethyl acetate (100 mL) and filtered through celite pad. The filtrate was washed with water (50 mL×2), dried over $Na_2SO_4$ and concentrated under reduced pressure. The crude product obtained was purified by silica gel column chromatography using methanol and dichloromethane as mobile phase to get the 4-{[2-fluoro-5-(trifluoromethoxy)phenyl]ethynyl}pyridin-3-amine 4 (456 mg, 70% yield).

Step 4

To the stirred solution 4-{[2-fluoro-5-(trifluoromethoxy)phenyl]ethynyl}pyridin-3-amine 4 (0.450 g, 1.0 eq.) in 1,4-dioxane (4.5 mL, 10 V) was added potassium tert-butoxide (0.340 g, 2.0 eq.). The resulting solution was stirred at 85° C. for 2 h. The reaction mass was then diluted with ethyl acetate (10 V) and filtered through celite pad. Celite plug was washed with ethyl acetate (5 V×2). The combined organic layer was washed with saturated ammonium chloride solution (10 V) followed by brine (10 V). The separated organic layer was dried over $Na_2SO_4$ and concentrated under reduced pressure. Crude compound was purified by flash column chromatography to get 2-[2-fluoro-5-(trifluoromethoxy)phenyl]-1H-pyrrolo[2,3-c]pyridine 5 (150 mg, 34%).

Step 5

To the solution of 2-[2-fluoro-5-(trifluoromethoxy)phenyl]-1H-pyrrolo[2,3-c]pyridine 5 (0.150 g, 1.0 eq.) in DMF (2.1 mL, 14 V), NaOH (0.018 g, 0.9 eq., 30% solution) and DIPEA (0.220 mL, 2.5 eq.) were added at 0° C. After 10 min stirring, 1-(chloromethyl)-1H-benzotriazole (0.109 g, 1.3 eq.) was added. The resulting solution was gradually warmed to ambient temperature and stirred for another 20 h. The progress of the reaction was monitored by TLC. After completion of the reaction, water (100 V) was slowly added. The reaction mixture was extracted with DCM (10% MeOH), the separated organic phase was washed with brine and concentrated under reduced pressure. The crude product was purified by column chromatography to get 1-({2-[2-fluoro-5-(trifluoromethoxy)phenyl]-6H-pyrrolo[2,3-c]pyridin-6-yl}methyl)-1H-benzotriazole (Compound II) as a solid (0.056 g, 26%).

$^1$H NMR (400 MHz, DMSO-d6) δ ppm: 9.20 (s, 1H), 8.31 (d, J=8.4 Hz, 2H), 8.12 (d, J=8.4 Hz, 1H), 7.99 (dd, 6.8 Hz, 1H), 7.76-7.71 (m, 2H), 7.49-7.45 (m, 3H), 7.42-7.39 (m, 2H), 7.06 (d, J=4.8 Hz, 1H).

ES+MS m/z: 427.9 (M+1).

Example 3. Synthesis of Compounds III and XII

Preparation of 2-(5-(2-(benzyloxy)ethoxy)-2-fluorophenyl)-1H-pyrrolo[2,3-c]pyridine 5, Common Intermediate

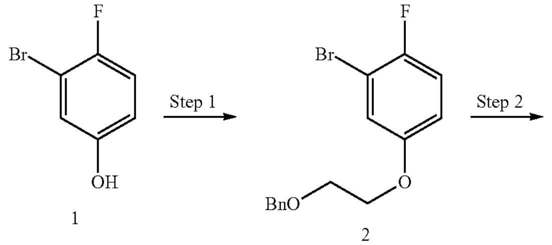

1

2

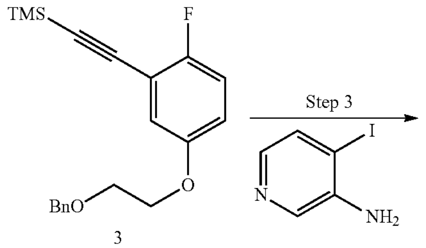

3

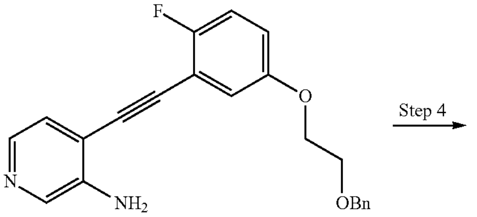

4

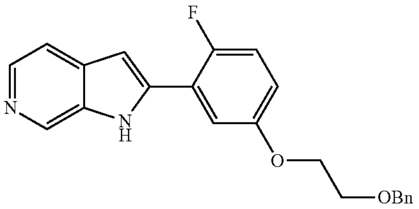

5

Step 1

To a solution of 3-bromo-4-fluorophenol (3.8 g, 1.0 eq.) in DMF (38 mL, 10 V) $K_2CO_3$ (6.9 g, 2.5 eq.) and ((2-bromoethoxy)methyl)benzene (4.73 g, 1.1 eq.) were added at 0° C. The reaction mixture was stirred at ambient temperature for 12 h. The reaction was quenched with water and the mixture was extracted with ethyl acetate. The separated organic layer was washed with brine, dried over $Na_2SO_4$ and concentrated under reduced pressure. The crude product was purified by column chromatography to get 4-[2-(benzyloxy)ethoxy]-2-bromo-1-fluorobenzene 2 (6.0 g, 93%).

Step 2

The stirred solution of 4-[2-(benzyloxy)ethoxy]-2-bromo-1-fluorobenzene 2 (6.0 g, 1.0 eq.) and TMS-Acetylene (0.315 mL, 1.2 eq.) in $Et_3N$:THF 1:1 (60 mL, 10 V) was purged with argon during 10 min. Copper(I) iodide (35 mg, 0.01 eq.) and bis(triphenylphosphine)palladium(II) dichloride (1.29 mg, 0.1 eq.) were added under inert atmosphere. The resulting black solution was stirred 90° C. for 6 h. The reaction was quenched with water and the mixture was extracted with ethyl acetate. The organic layer was separated, washed with brine, dried over $Na_2SO_4$ and concentrated under reduced pressure. The crude product was purified by column chromatography to get 3 (5.1 g, 81%).

Step 3

To the stirred solution of 3 (0.600 g, 1.0 eq.) and 4-iodopyridin-3-amine (0.385 g, 1.0 eq.) in THF (3 mL, 5 V) triethylamine (3 mL, 5 V) was added. The resulting brown solution was purged with argon for 15 min. Copper(I) iodide (0.0033 g, 0.01 eq.) and bis(triphenylphosphine)palladium (II) dichloride (0.123 g, 0.1 eq.) were added subsequently, followed by TBAF (1.0 M in THF, 2.5 mL, 1.5 eq.). The resulting black solution was stirred at 90° C. for 6 h. The reaction mixture was diluted with dichloromethane (10 V) and filtered through celite pad. Filtrate was concentrated and purified by column chromatography using ethyl acetate and hexane as mobile phase to get 4-({5-[2-(benzyloxy)ethoxy]-2-fluorophenyl}ethynyl)pyridin-3-amine 4 (520 mg, 81%).

Step 4

To the stirred solution of 4-{(5-[2-(benzyloxy)ethoxy]-2-fluorophenyl}ethynyl) pyridin-3-amine 4 (0.520 g, 1.0 eq.) in 1,4-dioxane (5.2 mL, 10 V) potassium tert-butoxide (0.322 g, 2.0 eq.) was added. The resulting solution was stirred at 85° C. for 12 h. The reaction mixture was diluted with dichloromethane (10 V) and filtered through celite pad. Celite plug was washed with DCM (5 V×2). Combined organic layer was washed with saturated ammonium chloride solution (10 V) followed by brine (10 V). The organic layer was dried over $Na_2SO_4$ and concentrated under reduced pressure. Crude compound was purified by flash column chromatography using ethyl acetate and hexane as mobile phase to get 2-{5-[2-(benzyloxy)ethoxy]-2-fluorophenyl}-1H-pyrrolo[2,3-c]pyridine 5 (480 mg, 74%).

Synthesis of 2-(3-{6-[(1H-benzotriazol-1-yl)methyl]-6H-pyrrolo[2,3-c]pyridin-2-yl}-4-fluorophenoxy)ethan-1-ol (Compound III)

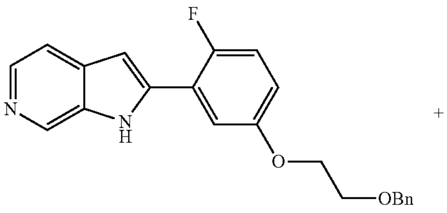

5

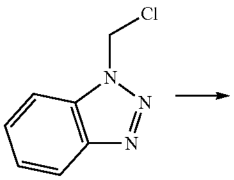

-continued

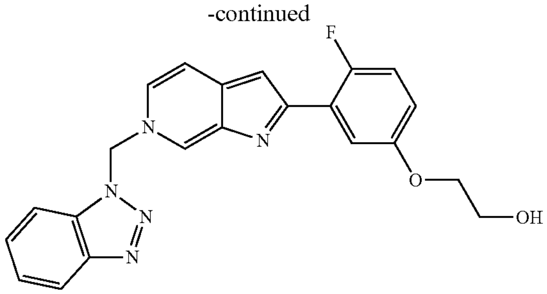

III

To a solution of 2-{5-[2-(benzyloxy)ethoxy]-2-fluorophenyl}-1H-pyrrolo[2,3-c]pyridine 5 (0.480 g, 1.0 eq.) in DMF (6.72 mL, 14 V) was added NaOH (47 mg, 0.9 eq. 30% Solution) and DIPEA (0.573 mL, 2.5 eq.) at 0° C. After 10 min stirring, 1-(chloromethyl)-1H-benzotriazole (0.242 g, 1.1 eq.) was added. The resulting brown solution was gradually warmed to ambient temperature and stirred for another 20 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get benzylated III (0.490 g, 74%).

To a solution of this intermediate (0.390 g, 1.0 eq.) in DCM (5.8 mL, 20 V) was added $BCl_3$ (1.0 M in DCM, 0.349 mL, 3.0 eq.) dropwise at 0° C. The resulting suspension was stirred at room temperature for 30 min. The reaction was quenched with methanol. The crude product obtained after solvent evaporation was purified by preparative HPLC to get 2-(3-{6-[(1H-benzotriazol-1-yl)methyl]-6H-pyrrolo[2,3-c]pyridin-2-yl}-4-fluorophenoxy)ethan-1-ol (Compound III) as off white solid (110 mg, 27%).

$^1$H NMR (400 MHz, DMSO-d6) δ ppm: 9.12 (s, 1H), 8.31 (d, J=8.4 Hz, 1H), 8.12 (d, J=8.4 Hz, 1H), 8.00 (d, J=6.4 Hz, 1H), 7.87-7.85 (dd, J=6 HZ, 1H), 7.71 (t, 1H), 7.66 (d, J=6.8 Hz, 1H), 7.49 (t, 2H), 7.39 (s, 1H), 7.22 (t, 1H), 7.17 (d, 1H), 6.96 (m, 1H), 4.91 (t, 1H), 4.04 (t, 2H), 3.75 (q, 2H).

ES+MS m/z: 404.3 (M+1).

Synthesis of 2-(4-fluoro-3-(6-((6-methyl-1,3-benzothiazol-2-yl)methyl)-6H-pyrrolo[2,3-c]pyridin-2-yl)phenoxy)ethan-1-ol (Compound XII)

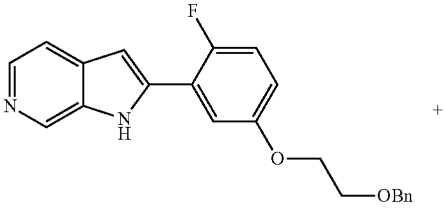

5

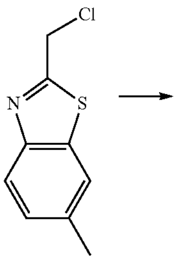

-continued

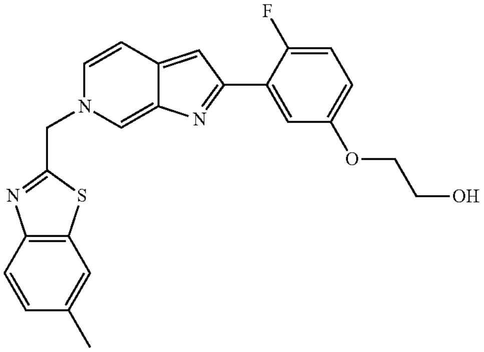

XII

To a solution of 2-{5-[2-(benzyloxy)ethoxy]-2-fluorophenyl}-1H-pyrrolo[2,3-c]pyridine 5 (0.370 g, 1.0 eq.) in DMF (5.18 mL, 14V) was added NaOH (36 mg, 0.9 eq., 30% solution) and DIPEA (0.444 mL, 2.5 eq.) at 0° C. After 10 min stirring, 2-(chloromethyl)-6-methyl-1,3-benzothiazole (0.221 g, 1.1 eq.) was added. The resulting brown solution was gradually warmed to ambient temperature and stirred for another 16 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get benzylated XII (0.300 g, 56%).

To the solution of this intermediate (0.300 g, 1.0 eq.) in DCM (6 mL, 20 V) was added $BCl_3$ (1.0 M in DCM, 0.201 mL) dropwise at 0° C. The resulting suspension was stirred at room temperature for 30 min. The reaction was quenched with methanol. The crude product obtained after solvent evaporation was purified by preparative HPLC to get 2-(4-fluoro-3-(6-((6-methyl-1,3-benzothiazol-2-yl)methyl)-6H-pyrrolo[2,3-c]pyridin-2-yl)phenoxy)ethan-1-ol (Compound XII) (30 mg, 12%).

$^1$H NMR (400 MHz, DMSO-d6) δ ppm: 8.98 (s, 1H), 7.91-7.83 (m, 4H), 7.67 (d, J=6.4 Hz, 1H), 7.35 (dd, J=8.4 Hz, 1H), 7.22 (t, 1H), 7.05 (d, J=4.8 Hz, 1H), 6.95-6.91 (m, 1H), 6.10 (s, 2H), 4.90 (t, 1H), 4.05 (t, 2H), 3.75 (q, 2H), 2.42 (s, 3H).

ES+MS m/z: 434.7 (M+1).

Example 4. Synthesis of Compound IV

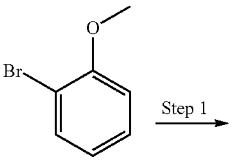

1

-continued

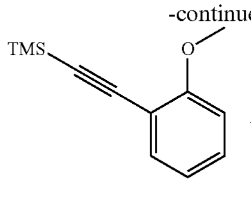

2

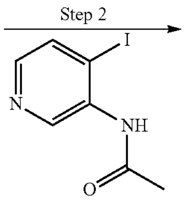

3

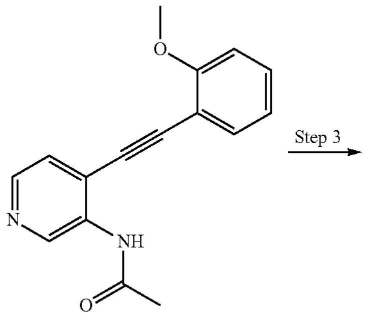

4

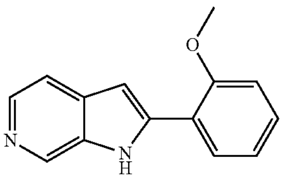

5

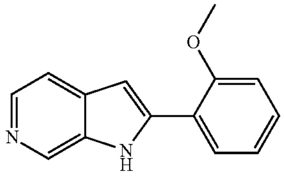

5

+

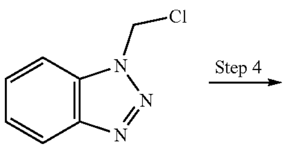

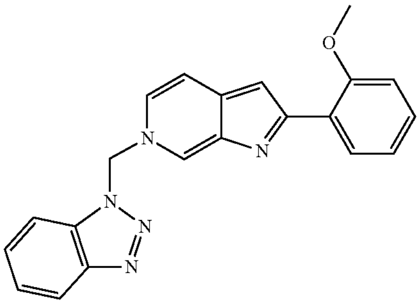

IV

Step 1

The stirred solution of 1-bromo-2-methoxybenzene (2.0 g, 1.0 eq.) and TMS-acetylene (2.2 mL, 1.5 eq.) in $Et_3N$: THF 1:1 (20 mL, 20 V) was purged with argon during 10 min. Copper(I) iodide (0.101 g, 0.05 eq.) and bis(triphenylphosphine)palladium(II) dichloride (0.750 g, 0.1 eq.) were added subsequently under inert atmosphere. The resulting black solution was stirred at 100° C. for 2 h. The reaction was quenched with water and the mixture was extracted with ethyl acetate. Organic layer was separated, washed with brine, dried over $Na_2SO_4$ and concentrated under reduced pressure. The crude product was purified by column chromatography to obtain intermediate 2 (0.753 g, 86%).

Step 2

To the stirred solution of intermediate 2 (0.500 g, 1.0 eq.) and N-(4-iodopyridin-3-yl)acetamide (0.641 g, 1.0 eq.) in THF (2.5 mL, 5 V) was added triethylamine (2.5 mL, 5 V). The resulting brown solution was purged with argon during 15 min. Copper(I) iodide (0.046 g, 0.01 eq.) and bis(triphenylphosphine)palladium(II) dichloride (0.172 g, 0.1 eq.) were added subsequently under inert atmosphere followed by TBAF (1.0 M in THF, 2.1 mL, 1.5 eq.). The resulting black solution was stirred at 50° C. for 12 h. The reaction mixture was diluted with dichloromethane (10 V) and filtered through celite pad. Filtrate was concentrated and purified by flash column chromatography using ethyl acetate and hexane as mobile phase to get N-{4-[(2-methoxyphenyl)ethynyl]pyridin-3-yl}acetamide 4 (450 mg, 88%).

Step 3

To the stirred solution of N-{4-[(2-methoxyphenyl)ethynyl]pyridin-3-yl}acetamide 4 (0.450 g, 1.0 eq.) in 1,4-dioxane (4.5.0 mL, 10 V) was added potassium tert-butoxide (0.486 g, 2.0 eq.). The resulting solution was stirred at 85° C. for 12 h. The reaction mixture was diluted with dichloromethane (10 V) and filtered through celite pad. Celite plug was washed with DCM (5 V×2). Combined organic layer was washed with saturated ammonium chloride solution (10 V) followed by brine (10 V). The separated organic layer was dried over $Na_2SO_4$ and concentrated under reduced pressure. Crude product was purified by flash column chromatography using ethyl acetate and hexane as mobile phase to get 2-(2-methoxyphenyl)-1H-pyrrolo[2,3-c]pyridine 5 (310 mg, 82%).

Step 4

To a solution of 2-(2-methoxyphenyl)-1H-pyrrolo[2,3-c]pyridine 5 (0.300 g, 1.0 eq.) in DMF (5.6. mL, 14 V) was added NaOH (48 mg, 0.9 eq. 30% solution) and DIPEA (0.770 mL, 2.5 eq.) at 0° C. After 10 min stirring, 1-(chloromethyl)-1H-benzotriazole (0.223 g, 1.1 eq.) was added. The resulting brown solution was gradually warmed to ambient temperature and stirred for another 20 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get 1-{[2-(2-methoxyphenyl)-6H-pyrrolo[2,3-c]pyridin-6-yl]methyl}-1H-benzotriazole (Compound IV) (85 mg, 18%.)

$^1H$ NMR (400 MHz, DMSO-d6) δ ppm: 8.97 (s, 1H), 8.32 (t, 2H), 8.12 (d, J=8.4 Hz, 1H), 7.91 (d, J=6.4 Hz, 1H), 7.71 (t, 1H), 7.55 (d, J=6.4 Hz, 1H), 7.49 (t, 1H), 7.35 (m, 3H), 7.20 (s, 1H), 7.10 (m, 1H), 7.00 (t, 1H), 3.88 (s, 3H).

ES+MS m/z: 356.3 (M+1).

Example 5. Synthesis of Compounds V, XIII and XVI

Preparation of (2-(1H-pyrrolo[2,3-c]pyridin-2-yl)phenyl)methanol 6, Common Intermediate

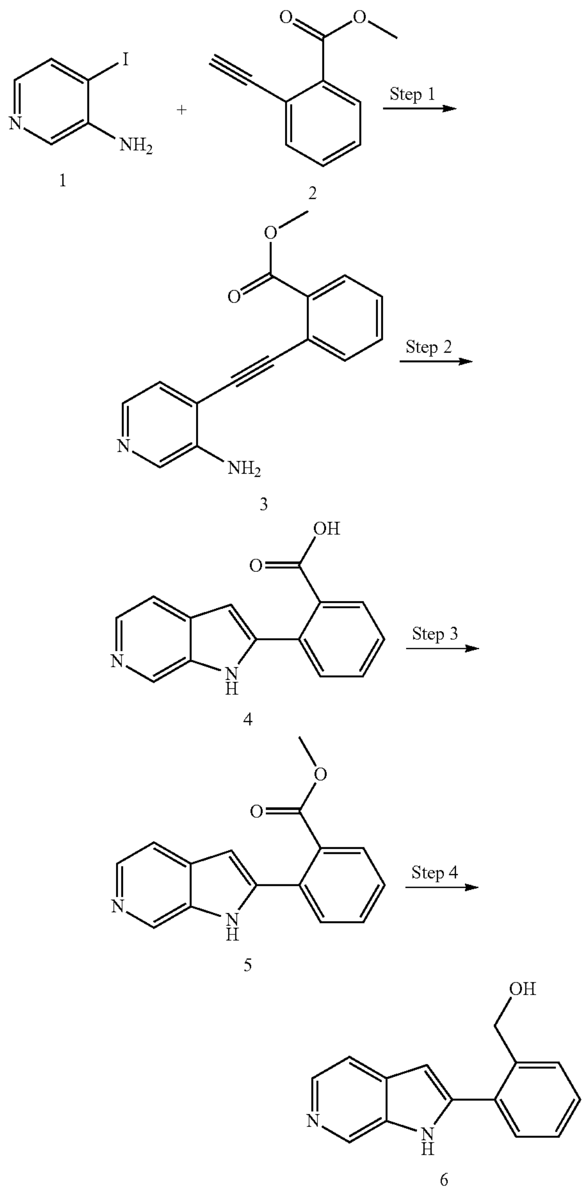

Step 1

The stirred solution of 4-iodopyridin-3-amine (0.5 g, 1.0 eq.) and methyl 2-ethynylbenzoate (0.36 g, 1.0 eq.) in THF:TEA 1:1 (10 mL, 20 V) was purged with argon during 15 min. Copper(I) iodide (0.021 g, 0.05 eq.) and bis(triphenylphosphine)palladium(II) dichloride (0.16 g, 0.1 eq.) were added subsequently under inert atmosphere. The resulting black solution was stirred at 90° C. for 6 h. The reaction mixture was then diluted with dichloromethane (10 V) and filtered through celite pad. Filtrate was concentrated and purified by column chromatography using ethyl acetate and hexane as mobile phase to get methyl 2-[(3-aminopyridin-4-yl)ethynyl]benzoate 3 (0.61 g, 76%).

Step 2

To the stirred solution of methyl 2-[(3-aminopyridin-4-yl)ethynyl]benzoate 3 (0.60 g, 1.0 eq.) in 1,4-dioxane (6 mL, 10 V) was added potassium tert-butoxide (0.53 g, 2.0 eq.). The resulting solution was stirred at 85° C. for 2 h. The reaction mixture was then diluted with dichloromethane (50 V) and filtered through celite pad. Celite plug was washed with DCM (5 V×2). Combined organic layers were concentrated under reduced pressure and the crude compound 4 was taken to next step without further purification (650 mg crude).

Step 3

2-(1H-pyrrolo[2,3-c]pyridin-2-yl)benzoic acid 4 (0.65 g, 1.0 eq.) was dissolved in methanol (6.5 mL, 10 V). The resulting brown turbid solution was cooled to 0° C. and $SO_2CO_2$ (0.61 mL, 3.0 eq.) was added slowly. The reaction was allowed to warm to ambient temperature and stirred for 12 h. The volatiles were removed under reduced pressure. The remaining mass was diluted with dichloromethane, washed with saturated bicarbonate solution and concentrated under reduced pressure. The crude product obtained was purified by column chromatography to get methyl 2-(1H-pyrrolo[2,3-c]pyridin-2-yl)benzoate 5 as brown solid (210 mg, 31%).

Step 4

The stirred solution of methyl 2-(1H-pyrrolo[2,3-c]pyridin-2-yl)benzoate 5 (0.21 g, 1.0 eq.) in THF (10 mL, 50 V) was cooled to −5° C. and LAH (0.10 g, 3.0 eq.) was added portion wise. The reaction was stirred at ambient temperature for 2 h. The reaction was quenched with eq. ammonium chloride solution and the mixture was extracted with DCM (10% MeOH). The separated organic layer was filtered through celite pad. The filtrate was concentrated under reduced pressure. Crude product was purified by column chromatography to get [2-(1H-pyrrolo[2,3-c]pyridin-2-yl)phenyl]methanol 6 as light yellow solid (150 mg, 80%).

Synthesis of [2-(6-((1H-Benzotriazol)-1-yl)methyl-6H-pyrrolo[2,3-c]pyridin-2-yl)-phenyl]-methanol (Compound V)

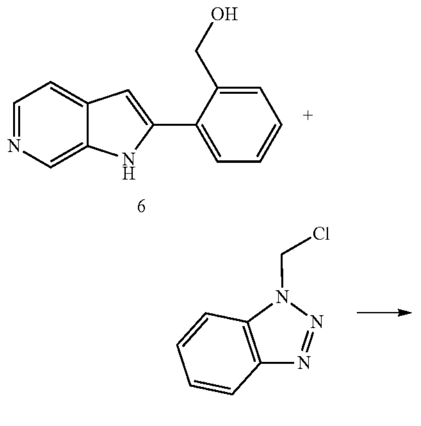

-continued

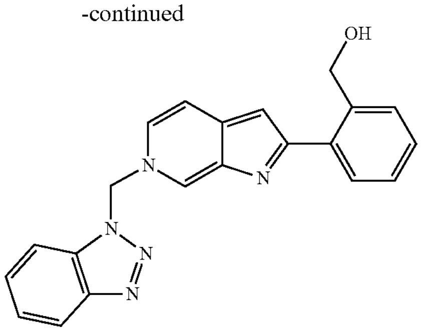

V

To a solution of [2-(1H-pyrrolo[2,3-c]pyridin-2-yl)phenyl]methanol 6 (0.15 g, 1.0 eq.) in DMF (2.0 mL, 14 V) was added NaOH (24 mg, 0.9 eq. 30% solution) and DIPEA (0.3 mL, 2.5 eq.) at 0° C. After 10 min stirring, 1-chloromethyl-1H-benzotriazole (0.123 g, 1.1 eq.) was added. The resulting brown solution was gradually warmed to ambient temperature and stirred for another 16 h. The reaction mixture was diluted with ice cold water (10 mL). The precipitated product was collected by filtration. The product was further washed with diethyl ether and cold methanol to get [2-(6-((1H-Benzotriazol)-1-yl)methyl-6H-pyrrolo[2,3-c]pyridin-2-yl)-phenyl]-methanol (Compound V) as an off-white solid (30 mg, 10%).

$^{1}$H NMR (400 MHz, DMSO-d6) δ ppm: 9.17 (s, 1H), 8.32 (d, 1H), 8.13 (d, 1H), 8.04 (d, 1H), 7.83 (d, 1H), 7.72-7.65 (m, 3H), 7.50-7.44 (m, 2H), 7.43-7.33 (m, 4H), 6.97 (s, 1H), 4.49 (s, 2H).

ES+MS m/z: 356.3 (M+1).

Preparation of (2-{6-[(6-methyl-1,3-benzothiazol-2-yl)methyl]-6H-pyrrolo[2,3-c]pyridin-2-yl}phenyl)methanol (Compound XIII)

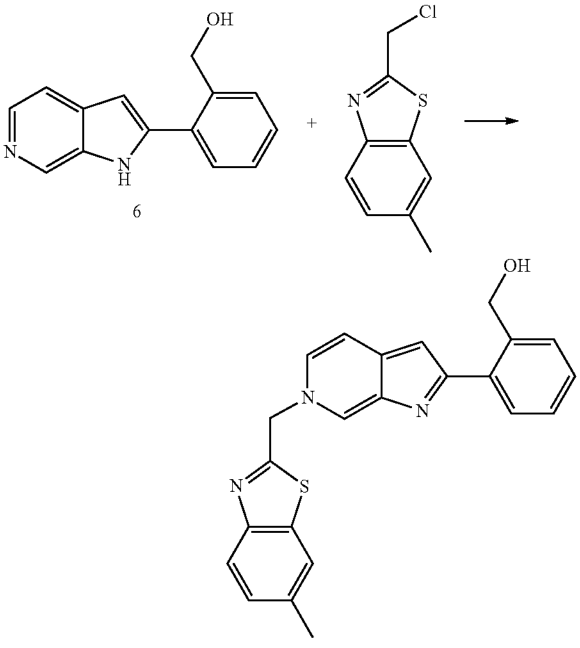

6

XIII

To a solution of [2-(1H-pyrrolo[2,3-c]pyridin-2-yl)phenyl]methanol 6 (0.130 g, 1.0 eq.) in DMF (1.82 mL, 14 V) was added NaOH (20 mg, 0.9 eq. 30% solution) and DIPEA (0.252 mL, 2.5 eq.) at 0° C. After 10 min stirring, 2-(chloromethyl)-6-methyl-1,3-benzothiazole (0.125 g, 1.1 eq.) was added. The resulting brown solution was gradually warmed to ambient temperature and stirred for another 12 h. The reaction mixture was diluted with ethyl acetate (10 V) and water (2 V). The organic layer was separated, dried over $Na_2SO_4$ and concentrated under reduced pressure. The crude was purified by column chromatography using ethyl acetate and hexane as mobile phase to get (2-{6-[(6-methyl-1,3-benzothiazol-2-yl)methyl]-6H-pyrrolo[2,3-c]pyridin-2-yl}phenyl)methanol (Compound XIII) as a pale yellow solid (40 mg, 18%). $^{1}$H NMR (400 MHz, DMSO-d6) δ ppm: 9.01 (s, 1H), 8.05 (br, s, 1H), 7.95-7.85 (m, 4H), 7.7 (d, 1H), 7.45-7.25 (m, 4H), 7.0 (s, 1H), 6.10 (s, 2H), 4.50 (s, 2H), 2.42 (s, 3H). ES+MS m/z: 388.8 (M+1).

Preparation of (2-(6-((6-methyl-1H-benzoimidazol-2-yl)methyl)-6H-pyrrolo[2,3-c]pyridin-2-yl)phenyl)methanol (Compound XVI)

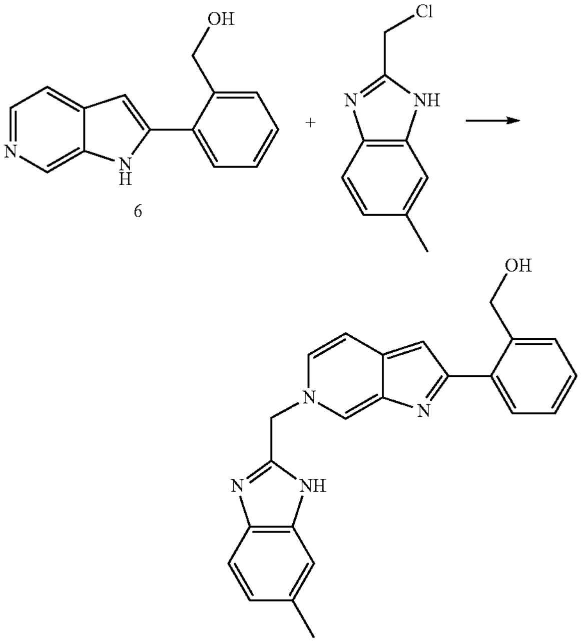

6

XVI

To a solution of [2-(1H-pyrrolo[2,3-c]pyridin-2-yl)phenyl]methanol 6 (0.300 g, 1.0 eq.) in DMF (4.2 mL, 14 V) was added NaOH (46 mg, 0.9 eq. 30% solution) and DIPEA (0.582 mL, 2.5 eq.) at 0° C. After 10 min stirring, 2-(chloromethyl)-6-methyl-1H-benzoimidazole (0.266 g, 1.1 eq.) was added. The resulting brown solution was gradually warmed to ambient temperature and stirred for another 12 h. The reaction mixture was diluted with ethyl acetate (10 V) and water (2 V). The organic layer was separated, dried over $Na_2SO_4$ and concentrated under reduced pressure. The crude was purified by column chromatography using ethyl acetate and hexane as mobile phase to get (2-(6-((6-methyl-1H-benzoimidazol-2-yl)methyl)-6H-pyrrolo[2,3-c]pyridin-2-yl)phenyl)methanol (Compound XVI) as a pale yellow solid (110 mg, 22%).

$^{1}$H NMR (400 MHz, DMSO-d6) δ ppm: 12.58 (s, 1H), 8.93 (s, 1H), 8.19 (br, s, 1H), 7.90-7.75 (m, 2H), 7.66 (d, 1H), 7.50-7.25 (m, 5H), 7.1-6.9 (m, 2H), 5.84 (s, 2H), 4.49 (s, 2H), 2.38 (s, 3H).

ES+MS m/z: 369.4 (M+1).

Example 6. Synthesis of Compound VI

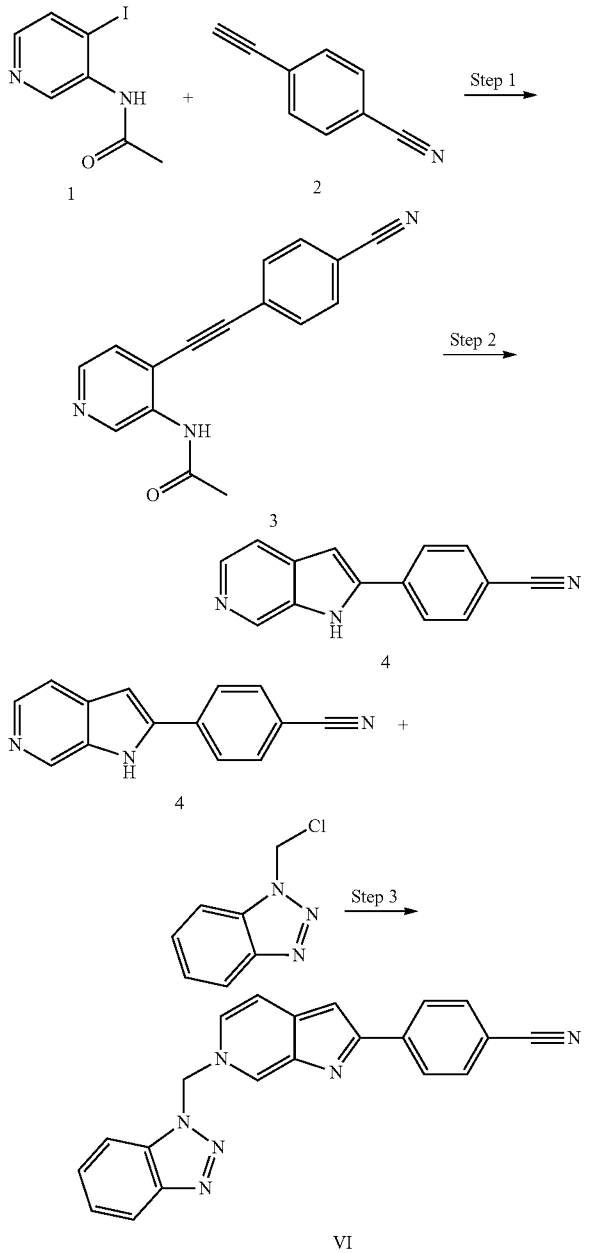

1 2 3 4 4 VI

Step 1

To a solution of N-(4-iodopyridin-3-yl)acetamide (0.500 g, 1.0 eq.) and 4-ethynylbenzonitrile (0.242 g, 1.0 eq.) in trimethylamine (5V) and tetrahydrofuran (5 V) was added copper(I) iodide (0.018 g, 0.05 eq.) and bis(triphenylphosphine)palladium(II) dichloride (0.133 g, 0.1 eq.) subsequently. The resulting brown solution was stirred at 90° C. for 6 h. The reaction mixture was then diluted with water and extracted with ethyl acetate. The separated organic layer was filtered through celite pad. The filtrate was concentrated and the crude was purified by column chromatography using ethyl acetate and hexane as mobile phase to get N-{4-[(4-cyanophenyl)ethynyl]pyridin-3-yl}acetamide 3 (0.420 g, 84%.)

Step 2

To the stirred solution of N-{4-[(4-cyanophenyl)ethynyl]pyridin-3-yl}acetamide 3 (0.420 g, 1.0 eq.) in DMF (4.2 mL, 10 V) was added $K_2CO_3$ (0.443 g, 2.0 eq.). The resulting solution was stirred at 85° C. for 4 h. The reaction mixture was then diluted with DCM (10 V) and filtered through celite pad. Celite plug was washed with DCM (5 V×2). Combined organic layer was washed with saturated ammonium chloride solution (10 V) followed by brine (10 V). The organic layer was dried over anhydrous $Na_2SO_4$ and concentrated. Crude product was purified by flash column chromatography by using ethyl acetate and hexane as mobile phase to get 4-(1H-pyrrolo[2,3-c]pyridin-2-yl)benzonitrile 4 (0.250 g, 71%).

Step 3

To the solution of 4-(1H-pyrrolo[2,3-c]pyridin-2-yl)benzonitrile 4 (0.250 g, 1.0 eq.) in DMF (2.5 mL, 5 V) was added DIPEA (2.5 mL, 5V) under inert atmosphere. After 5 min stirring, 1-(chloromethyl)-1H-benzotriazole (0.209 g, 1.1 eq.) was added. The resulting reaction was stirred at ambient temperature for 20 h. The reaction mixture was then diluted with water and extracted with dichloromethane. The organic layer was separated and concentrated. Crude was purified by preparative HPLC to get 4-{6-[(1H-benzotriazol-1-yl)methyl]-6H-pyrrolo[2,3-c]pyridin-2-yl}benzonitrile VI as a yellow solid (40 mg, 10%).

$^{1}$H NMR (400 MHz, DMSO-d6) δ ppm: 9.18 (s, 1H), 8.31-8.27 (m, 3H), 8.12 (d, J=8.4 Hz, 1H), 8.01 (d, 1H), 7.90 (d, J=8.4 Hz, 2H), 7.72-7.67 (m, 2H), 7.49 (t, 1H), 7.40 (s, 2H), 7.21 (s, 1H).

ES+MS m/z: 351.4 (M+1).

Example 7. Synthesis of Compounds VII, X and XIV

Preparation of 2-(2-methoxypyridin-3-yl)-1H-pyrrolo[2,3-c]pyridine 4, Common Intermediate

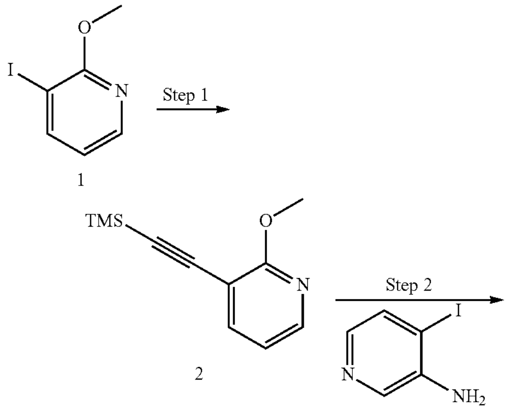

1 2

-continued

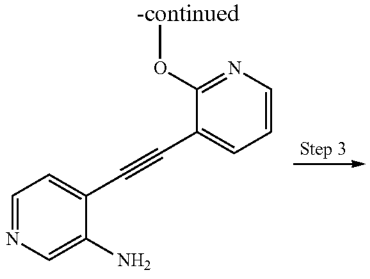

3

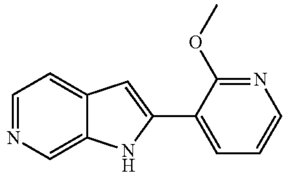

4

Step 1

The stirred solution of 3-iodo-2-methoxypyridine (1.0 g, 1.0 eq.) and TMS-acetylene (0.895 mL, 1.5 eq.) in TEA:THF 1:1 (20 mL, 20 V) was purged with argon during 10 min. Copper(I) iodide (0.040 mg, 0.05 eq.) and bis(triphenylphosphine)palladium(II) dichloride (0.298 g, 0.1 eq.) were added subsequently under inert atmosphere. The resulting black solution was stirred at 100° C. for 2 h. Then water was added and the mixture was extracted with ethyl acetate. The separated organic layer was washed with brine, dried over anhydrous $Na_2SO_4$ and concentrated under reduced pressure. The crude product was purified by column chromatography to get intermediate 2 (0.753 g, 86%).

Step 2

To the stirred solution of intermediate 2 (0.320 g, 1.0 eq.) in TEA:THF 1:1 (3.2 mL, 10 V) was added 4-iodopyridin-3-amine (0.358 g, 1.1 eq.). The resulting mixture was purged with argon during 15 min. Copper(I) iodide (0.0138 g, 0.05 eq.) and bis(triphenylphosphine)palladium(II) dichloride (0.101 g, 0.1 eq.) were added subsequently. The resulting brown solution was stirred at 90° C. for 6 h. The reaction mixture was diluted with ethyl acetate and filtered through celite pad. The filtrate was washed with water, dried over anhydrous $Na_2SO_4$ and concentrated under reduced pressure. Crude was purified by column chromatography using ethyl acetate and hexane as mobile phase to get 4-[(2-methoxypyridin-3-yl)ethynyl]pyridin-3-amine 3 (0.261 g, 80%).

Step 3

To the stirred solution of 4-[(2-methoxypyridin-3-yl)ethynyl]pyridin-3-amine 3 (0.260 g, 1.0 eq.) in 1,4-dioxane (2.6 mL, 10 V) was added potassium tert-butoxide (0.259 g, 2.0 eq.). The resulting solution was stirred at 85° C. for 4 h. The reaction mixture was then diluted with dichloromethane (10 V) and filtered through celite pad. Celite plug was washed with DCM (5 V×2). Combined organic layer was washed with saturated ammonium chloride solution (10 V) followed by brine (10 V). The organic layer was dried over anhydrous $Na_2SO_4$ and concentrated under reduced pressure. Crude compound was purified by flash column chromatography using ethyl acetate and hexane as mobile phase to get 2-(2-methoxypyridin-3-yl)-1H-pyrrolo[2,3-c]pyridine 4 (162 mg, 62%).

$^1H$ NMR (400 MHz, DMSO-d6) δ ppm: 12.1 (s, 1H), 8.85 (s, 1H), 8.35 (d, 1H), 8.25 (d, 1H), 8.15 (d, 1H), 7.65 (d, 1H), 7.20 (m, 2H), 4.1 (s, 3H).

ES+MS m/z: 226.4 (M+1).

Synthesis of 1-{[2-(2-methoxypyridin-3-yl)-6H-pyrrolo[2,3-c]pyridin-6-yl]methyl}-1H-benzotriazole (Compound VII)

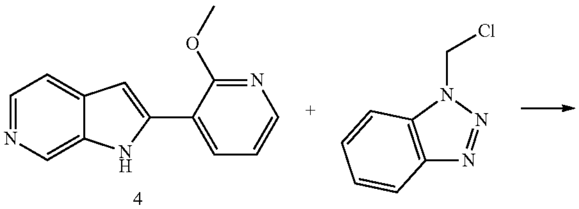

4

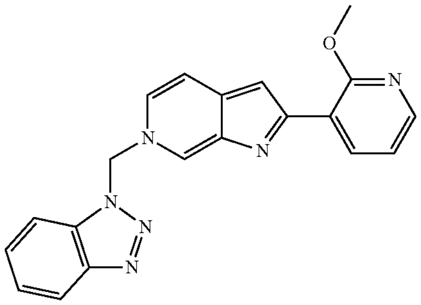

VII

To the solution of 2-(2-methoxypyridin-3-yl)-1H-pyrrolo[2,3-c]pyridine 4 (0.160 g, 1.0 eq.) in DMF (0.8 mL, 5 V) was added DIPEA (0.8 mL, 5V) under inert atmosphere. After 5 min stirring, 1-(chloromethyl)-1H-benzotriazole (0.130 g, 1.1 eq.) was added. The resulting reaction was stirred at ambient temperature for 20 h. The reaction mixture was diluted with water and extracted with dichloromethane. The separated organic layer was concentrated under reduced pressure. Crude was purified by preparative HPLC to get 1-{[2-(2-methoxypyridin-3-yl)-6H-pyrrolo[2,3-c]pyridin-6-yl]methyl}-1H-benzotriazole (Compound VII) as a green solid (30 mg, 12%).

$^1H$ NMR (400 MHz, DMSO-d6) δ ppm: 9.08 (s, 1H), 8.66 (d, J=6.4 Hz, 1H), 8.31 (d, 1H), 8.19 (d, 1H), 8.12 (d, 1H), 8.02 (d, J=6.4 Hz, 1H), 7.71-7.65 (m, 2H), 7.49 (t, 1H), 7.40 (s, 2H), 7.25 (s, 1H), 7.13 (t, 1H), 4.0 (s, 3H).

ES+MS m/z: 357.2 (M+1).

Synthesis of 2-((2-(2-methoxypyridin-3-vi)-6H-pyrrolo[2,3-c]pyridin-6-yl)methyl)-5-methyl-1,3-benzoxazole (Compound X)

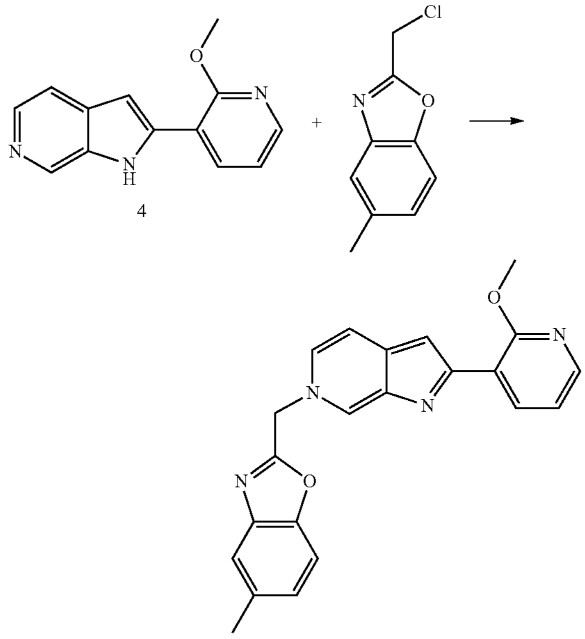

4

X

To the solution of 2-(2-methoxypyridin-3-yl)-1H-pyrrolo[2,3-c]pyridine 4 (0.075 g, 1.0 eq.) in DMF (0.4 mL, 5 V) was added DIPEA (0.4 mL, 5V) under inert atmosphere. After 5 min stirring, 2-(chloromethyl)-5-methyl-1,3-benzoxazole (0.067 g, 1.1 eq.) was added. The resulting reaction was stirred at ambient temperature for 20 h. The reaction mixture was diluted with water and extracted with dichloromethane. The separated organic layer was concentrated under reduced pressure. Crude was purified by preparative HPLC to get 2-((2-(2-methoxypyridin-3-yl)-6H-pyrrolo[2,3-c]pyridin-6-yl)methyl)-5-methyl-1,3-benzoxazole X as a yellow solid (50 mg, 41%).

$^1$H NMR (400 MHz, DMSO-d8) δ ppm: 8.85 (s, 1H), 8.70 (br s, 1H), 8.20-8.14 (m, 1H), 7.85-7.75 (m, 1H), 7.70-7.60 (m, 2H), 7.51 (s, 1H), 7.27 (s, 1H), 7.25-7.20 (m, 1H), 7.12-7.05 (m, 1H), 6.02 (s, 2H), 4.03 (s, 3H), 2.39 (s, 3H).

ES+MS m/z: 371.4 (M+1).

Preparation of 2-{[2-(2-methoxypyridin-3-yl)-6H-pyrrolo[2,3-c]pyridin-6-yl]methyl}-6-methyl-1,3-benzothiazole (Compound XIV)

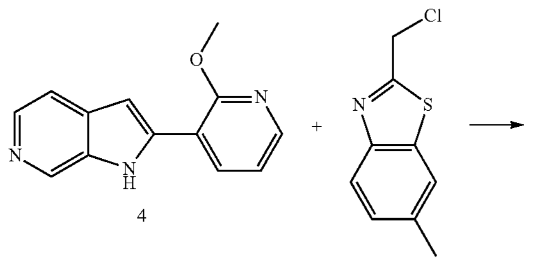

4

-continued

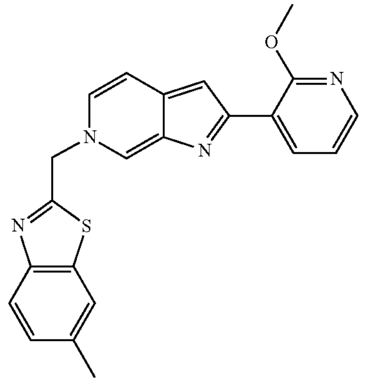

XIV

To a solution of 2-(2-methoxypyridin-3-yl)-1H-pyrrolo[2,3-c]pyridine 4 (0.200 g, 1.0 eq.) in DMF (2.8 mL, 14 V) was added NaOH (31 mg, 0.9 eq. 30% solution) and DIPEA (0.386 mL, 2.5 eq.) at 0° C. After 10 min stirring, 2-(chloromethyl)-6-methyl-1,3-benzothiazole (0.192 g, 1.1 eq.) was added. The resulting brown solution was gradually warmed to ambient temperature and stirred for another 16 h. The reaction mixture was diluted with ethyl acetate (10 V) and washed with water (2 V). The separated organic layer was dried over anhydrous $Na_2SO_4$ and concentrated under reduced pressure. The crude was purified by column chromatography using ethyl acetate and hexane as mobile phase to get 2-{[2-(2-methoxypyridin-3-yl)-6H-pyrrolo[2,3-c]pyridin-6-yl]methy}-6-methyl-1,3-benzothiazole XIV as a pale yellow solid (40 mg, 12%). $^1$H NMR (400 MHz, DMSO-d6) δ ppm: 8.87 (s, 1H), 8.71 (dd, J=7.6 Hz, 1H), 8.17 (dd, 1H), 7.88 (dd, 2H), 7.82 (d, J=6.8 Hz, 1H), 7.65 (d, J=6.8 Hz, 1H), 7.34 (d, 1H), 7.26 (s, 1H), 7.12 (dd, J=7.6 Hz, 1H), 6.09 (s, 2H), 4.1 (s, 3H), 2.42 (s, 3H). ES+MS m/z: 387.7 (M+1).

Example 8. Synthesis of Compounds VIII and XV

Preparation of 2-(1,5-dimethyl-1H-pyrazol-4-yl)-1H-pyrrolo[2,3-c]pyridine 5, Common Intermediate

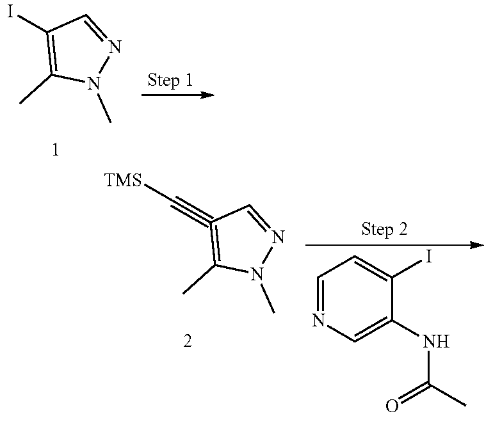

1

2

3

-continued

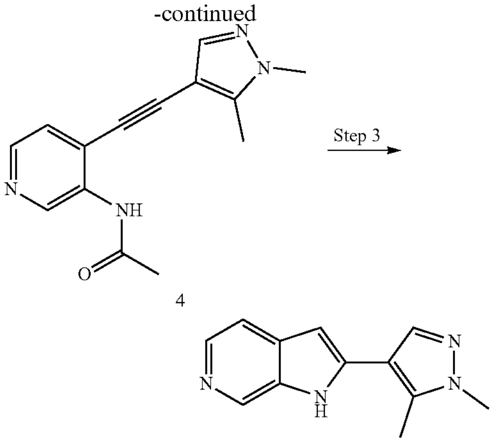

4

5

Preparation of N-(4-iodopyridin-3-yl)acetamide 3

To the stirred solution of 4-iodopyridin-3-amine (1.0 g, 1.0 eq.) in pyridine (5 mL, 5 V) was added acetic anhydride (0.42 mL, 1.0 eq.) dropwise at 0° C. The resulting reaction mass was stirred at ambient temperature for 12 h and then at 90° C. for 4 h. The volatiles were evaporated, the remaining mass was diluted with ethyl acetate (100 mL) and washed with water (50 mL×2). The separated organic phase was concentrated under reduced pressure. The crude product was purified by column chromatography using ethyl acetate and hexane as mobile phase to get N-(4-iodopyridin-3-yl)acetamide 3 as a light brown solid (0.54 g, 48%).

Step 1

The stirred solution of 4-iodo-1,5-dimethyl-1H-pyrazole (1.0 g, 1.0 eq.) and TMS-Acetylene (1.0 mL, 1.5 eq.) in diisopropylamine (10 mL, 10 V) was purged with argon during 10 min. Copper(I) iodide (90 mg, 0.09 eq.) and bis(triphenylphosphine)palladium(II) dichloride (70 mg, 0.02 eq.) were added subsequently under inert atmosphere. The resulting solution was stirred at 100° C. for 2 h. Then the volatiles were evaporated, the remaining mass was diluted with ethyl acetate (100 mL) and filtered through celite pad. The filtrate was washed with water (50 mL×2) and concentrated under reduced pressure. The crude product was purified by column chromatography using ethyl acetate and hexane as mobile phase to get 1,5-dimethyl-4-(trimethylsilyl)ethynyl-1H-pyrazole 2 as a light yellow solid (0.81 g, yield: 93%).

Step 2

The stirred solution of N-(4-iodopyridin-3-yl)acetamide 3 (0.4 g, 1.0 eq.) and 1,5-dimethyl-4-(trimethylsilyl)ethynyl-1H-pyrazole 2 (0.35 g, 1.0 eq.) in TEA:THF 1:1 (8.0 mL, 20 V) was purged with argon during 10 min. Copper(I) iodide (20 mg, 0.05 eq.) and bis(triphenylphosphine)palladium(II) dichloride (128 mg, 0.1 eq.) were added followed by tetrabutylammonium fluoride (1.0M, 2.4 mL, 1.2 eq.) under inert atmosphere. The resulting solution was stirred at room temperature for 12 h. Then the volatiles were evaporated, the remaining mass was diluted with ethyl acetate (100 mL) and filtered through celite pad. The filtrate was washed with water (50 mL×2) and concentrated under reduced pressure. The crude product was purified by column chromatography using methanol and dichloromethane as mobile phase to get N-[4-((1,5-dimethyl-1H-pyrazol-4-yl)ethynyl)pyridin-3-yl]acetamide 4 as a brown solid (0.38 g, 73%).

Step 3

To the stirred solution of N-[4-((1,5-dimethyl-1H-pyrazol-4-yl)ethynyl)pyridin-3-yl]acetamide 4 (0.780 g, 1.0 eq.) in DMF (7.6 mL, 10 V) was added $K_2CO_3$ (0.82 g, 2.0 eq.). The resulting solution was stirred at 85° C. for 2 h. The reaction mass was diluted with ethyl acetate (10 V) and filtered through celite pad. Celite plug was washed with ethyl acetate (5 V×2). Combined organic layer was washed with saturated ammonium chloride solution (10 V) followed by brine (10 V). The organic layer was dried over anhydrous $Na_2SO_4$ and concentrated under reduced pressure. Crude compound was purified by flash column chromatography to get 2-(1,5-dimethyl-1H-pyrazol-4-yl)-1H-pyrrolo[2,3-c]pyridine as an off-white solid (0.380 g, 57%). $^1$H NMR (400 MHz, DMSO-d6) δ ppm: 13.08 (br s, 1H), 8.89 (s, 1H), 8.20 (d, 1H), 8.18 (d, 1H), 7.90 (d, 1H), 6.95 (s, 1H), 3.85 (s, 3H), 2.56 (s, 3H).

Synthesis of 1-[(2-(1,5-dimethyl-1H-pyrazol-4-yl)-6H-pyrrolo[2,3-c]pyridin-6-yl)methyl]-1H-benzotriazole (Compound VIII)

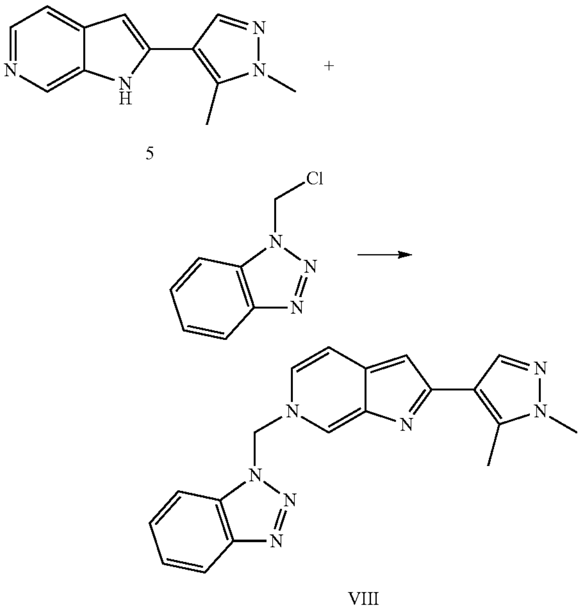

5

VIII

To a solution of 2-(1,5-dimethyl-1H-pyrazol-4-yl)-1H-pyrrolo[2,3-c]pyridine 5 (0.31 g, 1.0 eq.) in DMF (4.3 mL, 14 V) was added 30% NaOH solution (52 mg, 0.9 eq.) and DIPEA (0.67 mL, 2.5 eq.) at 0° C. After 10 min stirring, 1-chloromethyl-1H-benzotriazole (0.27 g. 1.1 eq.) was added. The resulting brown solution was gradually warmed to ambient temperature and stirred for another 16 h. The reaction mixture was diluted with ethyl acetate (150 mL) and washed with water (50 mL). The organic layer was separated, dried over $Na_2SO_4$ and concentrated under reduced pressure. The crude was purified by column chromatography using methanol and dichloromethane as mobile phase to get 1-[(2-(1,5-dimethyl-1H-pyrazol-4-yl)-6H-pyrrolo[2,3-c]pyridin-6-yl)methy]-1H-benzotriazole (Compound VIII) as an off-white solid (24 mg, 5%).

$^1$H NMR (400 MHz, DMSO-d6) δ ppm: 8.81 (s, 1H), 8.29 (d, J=8.4 Hz, 1H) 8.11 (d, J=8.4 Hz, 1H), 7.88 (d, 1H), 7.81 (s, 1H), 7.7 (t, 1H), 7.48-7.41 (m, 2H), 7.29 (s, 2H), 6.71 (s, 1H), 3.76 (s, 3H), 2.65 (s, 3H).

ES+MS m/z: 344.3 (M+1).

Preparation of 2-{[2-(1,5-dimethyl-1H-pyrazol-4-yl)-6H-pyrrolo[2,3-c]pyridin-6-yl]methyl}-6-methyl-1,3-benzothiazole (Compound XV)

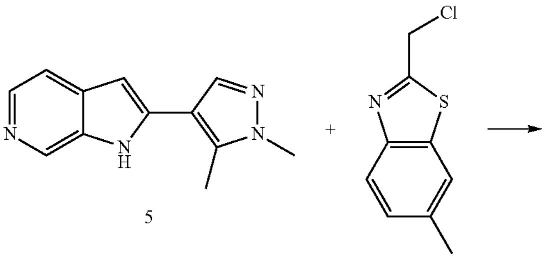

5

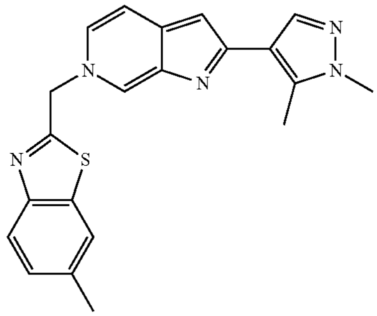

XV

To a solution of 2-(1,5-dimethyl-1H-pyrazol-4-yl)-1H-pyrrolo[2,3-c]pyridine 5 (0.240 g, 1.0 eq.) in DMF (3.3 mL, 14 V) was added NaOH (40 mg, 0.9 eq. 30% solution) and DIPEA (0.491 mL, 2.5 eq.) at 0° C. After 10 min stirring, 2-(chloromethyl)-6-methyl-1,3-benzothiazole (0.244 g, 1.1 eq.) was added. The resulting brown solution was gradually warmed to ambient temperature and stirred for another 16 h. The reaction mixture was diluted with ethyl acetate (15 V) and washed with water (2 V). The organic layer was separated, dried over $Na_2SO_4$ and concentrated under reduced pressure. The crude was purified by column chromatography using ethyl acetate and hexane as mobile phase to get 2-{[2-(1,5-dimethyl-1H-pyrazol-4-yl)-6H-pyrrolo[2,3-c]pyridin-6-yl]methyl}-6-methyl-1,3-benzothiazole (Compound XV) as a pale yellow solid (0.52 g, 12%).

$^1$H NMR (400 MHz, DMSO-d6) δ ppm: 8.66 (s, 1H), 7.88-7.83 (m, 3H), 7.76 (d, J=6.4 Hz, 1H), 7.48 (d, J=6.4 Hz, 1H), 7.34 (d, J=8.4 Hz, 1H), 6.74 (s, 1H), 6.02 (s, 2H), 3.77 (s, 3H), 2.67 (s, 3H), 2.42 (s, 3H).

ES+MS m/z: 374.20 (M+1).

Example 9. Synthesis of Compounds XVII, XXV and XXVIII

Preparation of 2-(2-fluorophenyl)-1H-pyrrolo[3,2-c]pyridine 4, Common Intermediate

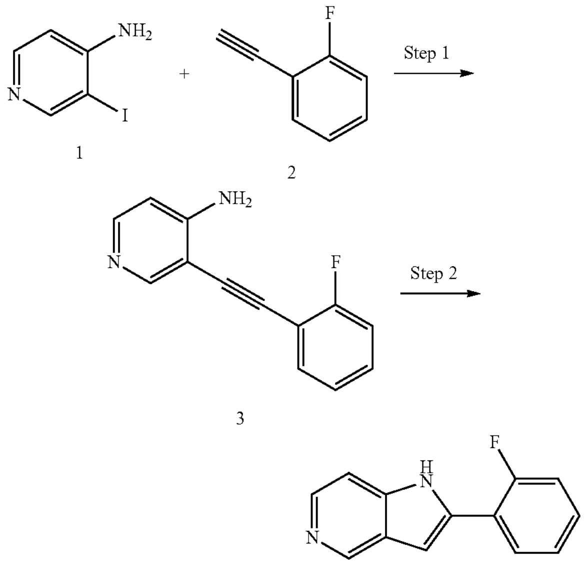

1 2 3 4

Step 1

The stirred solution of 3-iodopyridin-4-amine (1.0 g, 1.0 eq.) and 1-ethynyl-2-fluorobenzene (1 g, 1.0 eq.) in triethylamine (5 mL, 5 V) was purged with argon during 15 min. Then copper(I) iodide (42 mg, 0.05 eq.) and bis(triphenylphosphine)palladium(II) dichloride (0.315 g, 0.1 eq.) were subsequently added under inert atmosphere. The resulting black solution was stirred at 50° C. for 12 h. The reaction mixture was diluted with dichloromethane (10 V) and filtered through celite pad. The filtrate was concentrated and the crude was purified by column chromatography using ethyl acetate and hexane as mobile phase to get 3-[(2-fluorophenyl)ethynyl]pyridin-4-amine 3 (0.726 g, 75%).

Step 2

To the stirred solution of 3-[(2-fluorophenyl)ethynyl]pyridin-4-amine 3 (0.700 g, 1.0 eq.) in NMP (7 mL, 10 V) was added potassium tert-butoxide (0.739 g, 2.0 eq.). The resulting solution was stirred at 90° C. for 2 h. The reaction mixture was diluted with dichloromethane (10 V) and filtered through celite pad. The celite plug was washed with DCM (5 V×2). The combined organic layer was washed with saturated ammonium chloride solution (10 V) followed by brine (10 V). The organic layer was dried over anhydrous $Na_2SO_4$ and concentrated under reduced pressure. The crude was purified by column chromatography using ethyl acetate and hexane as mobile phase to get 2-(2-fluorophenyl)-1H-pyrrolo[3,2-c]pyridine 4 (0.421 g, 61%).

$^1$H NMR (400 MHz, DMSO-d8) δ ppm: 12.15 (br s, 1H), 8.90 (s, 1H), 8.22 (d, 1H), 7.90 (t, 1H), 7.40 (m, 4H), 7.05 (d, 1H).

ES+MS m/z: 213.1 (M+1).

Preparation of 1-{[2-(2-fluorophenyl)-5H-pyrrolo[3,2-c]pyridin-5-yl]methyl}-1H-benzotriazole (Compound XVI)

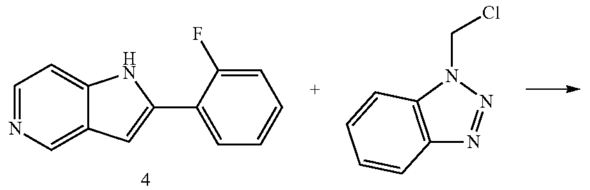

4

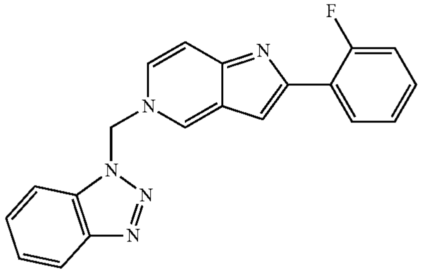

XVII

To a solution of 2-(2-fluorophenyl)-1H-pyrrolo[3,2-c]pyridine 4 (0.400 g, 1.0 eq.) in DMF (2.8 mL, 14 V) was added NaOH (7 mg, 0.9 eq., 30% solution) and DIPEA (0.721 mL, 2.5 eq.) at 0° C. After 10 min stirring, 1-(chloromethyl)-1H-benzotriazole (0.346 g, 1.1 eq.) was added. The resulting brown solution was gradually warmed to ambient temperature and stirred for another 12 h. The reaction mixture was then diluted with ethyl acetate (10 V) and washed with water (2 V). The organic layer was dried over $Na_2SO_4$ and concentrated under reduced pressure. The crude was purified by column chromatography using ethyl acetate and hexane as mobile phase to get 1-{[2-(2-fluorophenyl)-5H-pyrrolo[3,2-c]pyridin-5-yl]methyl}-1H-benzotriazole (Compound XVII) as a solid (142 mg, 22%).

$^1$H NMR (400 MHz, DMSO-d6) δ ppm: 9.18 (s, 1H), 8.35 (t, 1H), 8.25 (t, 1H), 8.17 (dd, J=7.2, 1H), 8.12 (d, 1H), 7.7 (t, 1H), 7.58 (1H, J=7.2 Hz, 1H), 7.50 (t, 1H), 7.38 (s, 2H), 7.30 (t, 1H), 7.15-7.28 (m, 3H).

ES+MS m/z: 344.3 (M+1).

Synthesis of 2-{[2-(2-fluorophenyl)-5H-pyrrolo[3,2-c]pyridin-5-yl]methyl}-5-methyl-1,3-benzoxazole (Compound XXV)

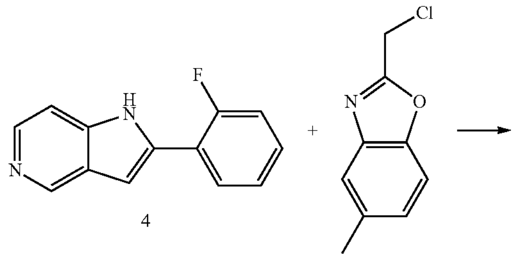

-continued

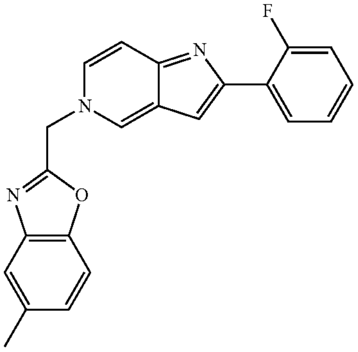

XXV

To a solution of 2-(2-fluorophenyl)-1H-pyrrolo[3,2-c]pyridine 4 (0.300 g, 1.0 eq.) in DMF (4.2 mL, 14 V) was added NaOH (50 mg, 0.9 eq., 30% solution) and DIPEA (0.614 mL, 2.5 eq.) at 0° C. After 10 min stirring, 2-(chloromethyl)-5-methyl-1,3-benzoxazole (0.281 g, 1.1 eq.) was added. The resulting brown solution was gradually warmed to ambient temperature and stirred for another 12 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get 2-{[2-(2-fluorophenyl)-5H-pyrrolo[3,2-c]pyridin-5-yl]methyl}-5-methyl-1,3-benzoxazole (Compound XXV) as an off white solid (120 mg, 23%).

$^1$H NMR (400 MHz, DMSO-d6) δ ppm: 8.91 (s, 1H), 8.41 (t, 1H), 7.95-7.93 (m, 1H), 7.62 (d, 1H), 7.58 (d, J=7.2 Hz, 1H), 7.51 (s, 1H), 7.32-7.18 (m, 5H), 6.01 (s, 2H), 2.39 (s, 3H).

ES+MS m/z: 358.5 (M+1).

Preparation of 2-{[2-(2-fluorophenyl)-5H-pyrrolo[3,2-c]pyridin-5-yl]methyl}-6-methyl-1,3-benzothiazole (Compound XXVIII)

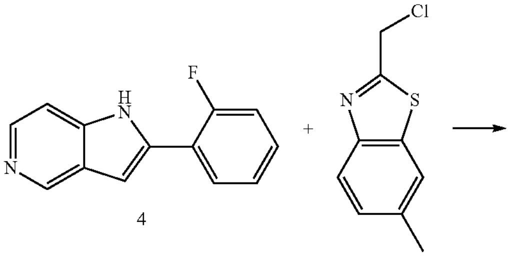

-continued

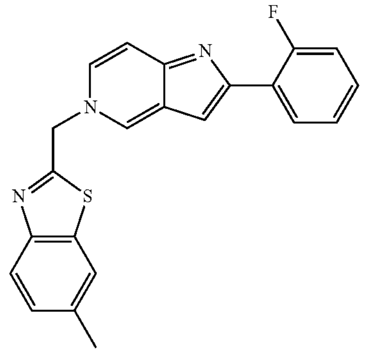

XXVIII

To a solution of 2-(2-fluorophenyl)-1H-pyrrolo[3,2-c]pyridine 4 (0.200 g, 1.0 eq.) in DMF (2.8 mL, 14 V) was added NaOH (33 mg, 0.9 eq., 30% solution) and DIPEA (0.410 mL, 2.5 eq.) at 0° C. After 10 min stirring, 2-(chloromethyl)-6-methyl-1,3-benzothiazole (0.203 g, 1.1 eq.) was added. The resulting brown solution was gradually warmed to ambient temperature and stirred for another 12 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get 2-{[2-(2-fluorophenyl)-5H-pyrrolo[3,2-c]pyridin-5-yl]methyl}-6-methyl-1,3-benzothiazole (Compound XXVIII) as a pale yellow solid (75 mg, 20%). $^1$H NMR (400 MHz, DMSO-d6) δ ppm: 8.96 (s, 1H), 8-45-8.35 (m, 1H), 8.00-7.95 (m, 1H), 7.92-7.83 (m, 2H), 7.60-7.55 (m, 1H), 7.40-7.22 (m, 4H), 7.20-7.17 (m, 1H), 8.09 (s, 2H), 2.42 (s, 3H). ES+MS m/z: 374.6 (M+1).

Example 10. Synthesis of Compound XVIII

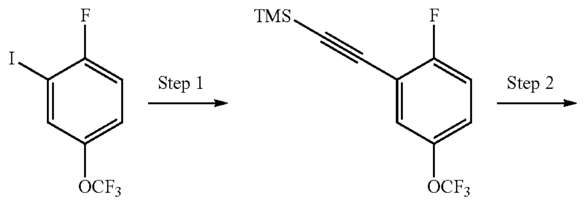

1 2

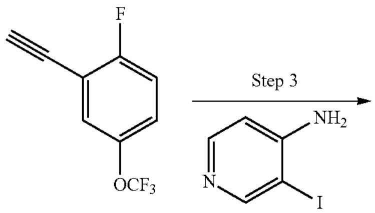

3

-continued

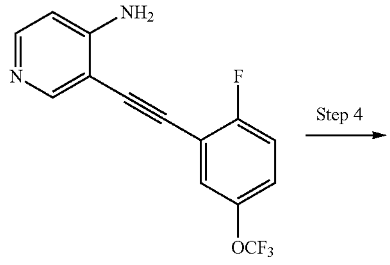

4

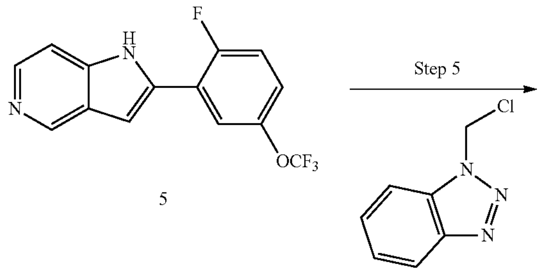

5

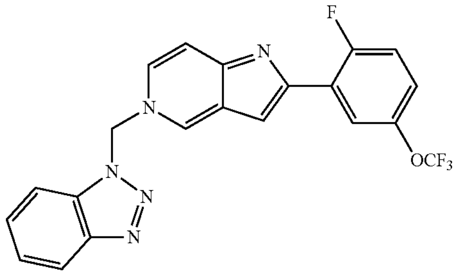

XVIII

The stirred solution of 1-fluoro-2-iodo-4-(trifluoromethoxy)benzene (1.5 g, 1.0 eq.) and TMS-Acetylene (1.05 mL, 1.5 eq.) in triethylamine (15 mL, 10 V) was purged with argon during 10 min. Copper(I) iodide (84 mg, 0.09 eq.) and bis(triphenylphosphine)palladium(II) dichloride (68 mg, 0.02 eq.) were added subsequently under inert atmosphere. The resulting solution was stirred at 100° C. for 2 h. Then the volatiles were evaporated, the remaining mass was diluted with ethyl acetate (100 mL) and filtered through celite pad. The filtrate was washed with water (50 mL×2) and concentrated under reduced pressure. The crude product obtained was purified by column chromatography using ethyl acetate and hexane as mobile phase to get 2 (0.882 g, 65%).

Step 2

Intermediate 2 (0.880 g) was dissolved in methanol (8.8 ml, 10 V) under inert atmosphere. Then $K_2CO_3$ (0.880 g, 2.0 eq.) was added and the resulting reaction mixture was stirred for 12 h. Reaction was monitored by TLC. Once the starting material disappeared, methanol was evaporated under reduced pressure. The crude was diluted with ethyl acetate and washed subsequently with water and brine. The organic layer was dried over $Na_2SO_4$ and concentrated to get 2-ethynyl-1-fluoro-4-(trifluoromethoxy)benzene 3 (487 mg, 75%). The product was used in next step without further purification.

Step 3

The stirred solution of 2-ethynyl-1-fluoro-4-(trifluoromethoxy)benzene 3 (0.450 g, 1.0 eq.), 3-iodopyridin-4-amine (0.483 g, 1.0 eq.) and triethyl amine (0.612 mL, 2 eq.) in THF (9.6 ml, 20 V) was purged with argon during 10 min. Then copper(I) iodide (20 mg, 0.05 eq.) and bis(triphenylphosphine) palladium(II) dichloride (154 mg, 0.1 eq.) were added subsequently under inert atmosphere. The reaction mixture was stirred at room temperature for 12 h. Then, the volatiles were evaporated, the remaining mass was diluted with ethyl acetate (100 mL) and filtered through celite pad. The filtrate was washed with water (50 mL×2) and concentrated under reduced pressure. The crude product obtained was purified by column chromatography using methanol and dichloromethane as mobile phase to get 3-{[2-fluoro-5-(trifluoromethoxy)phenyl]ethynyl}pyridin-4-amine 4 (465 mg, 71%).

Step 4

To the stirred solution of 3-{[2-fluoro-5-(trifluoromethoxy)phenyl]ethynyl}pyridin-4-amine 4 (0.450 g, 1.0 eq.) in DMF (4.5 mL, 10 V) was added potassium tert-butoxide (0.340 g, 2.0 eq.). The resulting solution was stirred at 85° C. for 2 h. The reaction mass was diluted with ethyl acetate (10 V) and filtered through celite pad. Celite plug was washed with ethyl acetate (5 V×2). Combined organic layer was washed with saturated ammonium chloride solution (10 V) followed by brine (10 V). Organic layer dried over anhydrous $Na_2SO_4$ and concentrated under reduced pressure. Crude compound was purified by flash column chromatography to get 2-[2-fluoro-5-(trifluoromethoxy)phenyl]-1H-pyrrolo[3,2-c]pyridine 5 (150 mg, 34%).

Step 5

To the solution of 2-[2-fluoro-5-(trifluoromethoxy)phenyl]-1H-pyrrolo[3,2-c]pyridine 5 (0.150 g, 1.0 eq.) in DMF (2.1 mL, 14 V) was added NaOH (0.018 g, 0.9 eq., 30% solution) and DIPEA (0.220 mL, 2.5 eq.) at 0° C. After 10 min stirring, 1-(chloromethyl)-1H-benzotriazole (0.109 g, 1.3 eq.) was added. The resulting solution was gradually warmed to ambient temperature and stirred for another 20 h. The reaction mass was slowly added to water (100 V) and extracted with DCM (10% MeOH). The organic layer was washed with brine and concentrated under reduced pressure. The crude was purified by column chromatography to get 1-({2-[2-fluoro-5-(trifluoromethoxy)phenyl]-5H-pyrrolo[3,2-c]pyridin-5-yl}methyl)-1H-benzotriazole (Compound XVIII) as solid (0.030 g, 13%).

$^1$H NMR (400 MHz, DMSO-d6) δ ppm: 9.21 (s, 1H), 8.31-8.21 (m, 2H), 8.20-8.08 (m, 2H), 7.69 (t, J=7.6 Hz, 1H), 7.60 (d, J=7.2 Hz, 1H), 7.52-7.28 (m, 5H), 7.29 (d, J=4.4 Hz, 1H).

ES+MS m/z: (M+1): 428.1.

Example 11. Synthesis of Compounds XIX and XXIX

Preparation of 2-{5-[2-(benzyloxy)ethoxy]-2-fluorophenyl}-1H-pyrrolo[3,2-c]pyridine 5, Common Intermediate

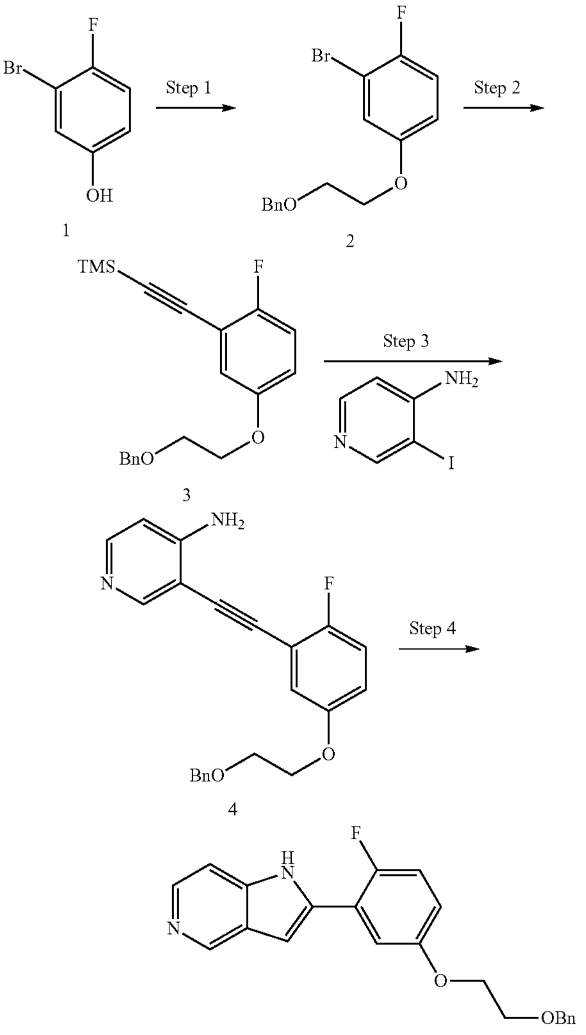

1 2 3 4 5

Step 1 and 2 are described above.

Step 3

To the stirred solution of 3 (0.600 g, 1.0 eq.) and 3-iodopyridin-4-amine (0.385 g, 1.0 eq.) in THF (3 mL, 5 V) was added triethylamine (3 mL, 5 V). The resulting brown solution was purged with argon during 15 min. Copper(I) iodide (0.0033 g, 0.01 eq.) and bis(triphenylphosphine) palladium(II) dichloride (0.122 g, 0.1 eq.) were subsequently added under inert atmosphere. Then TBAF was added (1M in THF, 2.6 mL, 1.5 eq.). The resulting black solution was stirred at 90° C. for 6 h. Then the reaction mixture was diluted with dichloromethane (10 V) and filtered through celite pad. The filtrate was concentrated under reduced pressure. The crude was purified by column chromatography using ethyl acetate and hexane as mobile phase to get 3-({5-[2-(benzyloxy)ethoxy]-2-fluorophenyl}ethynyl)pyridin-4-amine 4 (500 mg, 78%).

Step 4

To the stirred solution of 3-({5-[2-(benzyloxy)ethoxy]-2-fluorophenyl}ethynyl) pyridin-4-amine 4 (0.500 g, 1.0 eq.) in 1,4-dioxane (5.0 mL, 10 V) was added potassium tert-butoxide (0.309 g, 2.0 eq.). The resulting solution was stirred at 85° C. for 12 h. The reaction mixture was diluted with dichloromethane (10 V) and filtered through celite pad. Celite plug was washed with DCM (5 V×2). The combined organic layer was washed with saturated ammonium chloride solution (10 V) followed by brine (10 V). The organic layer was dried over anhydrous $Na_2SO_4$ and concentrated under reduced pressure. Crude was purified by flash column chromatography to get 2-{5-[2-(benzyloxy)ethoxy]-2-fluorophenyl}-1H-pyrrolo[3,2-c]pyridine 5 (0.450 g, 90%).

Preparation of 2-(3-{5-[(1H-benzotriazol-1-yl)methyl]-5H-pyrrolo[3,2-c]pyridin-2-yl}-4-fluorophenoxy)ethan-1-ol (Compound XIX)

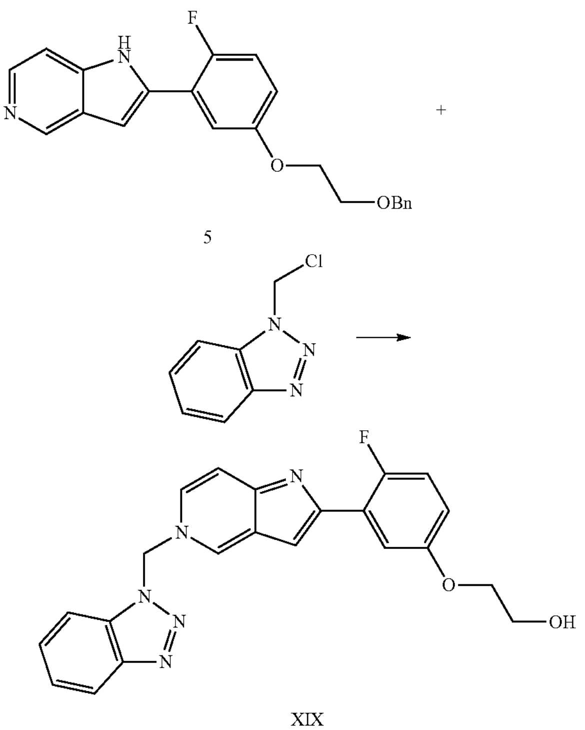

XIX

To a solution of 2-{5-[2-(benzyloxy)ethoxy]-2-fluorophenyl}-1H-pyrrolo[3,2-c]pyridine 5 (0.400 g, 1.0 eq.) in DMF (5.6. mL, 14 V) was added NaOH (39 mg, 0.9 eq. 30% solution) and DIPEA (0.478 mL, 2.5 eq.) at 0° C. After 10 min stirring, 1-(chloromethyl)-1H-benzotriazole (0.202 g, 1.1 eq.) was added. The resulting brown solution was gradually warmed to ambient temperature and stirred for another 20 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get benzylated XIX (470 mg, 81%).

To the solution of this intermediate (0.470 g, 1.0 eq.) in DCM (9.4 mL, 20 V) was added $BCl_3$ (1.0 M in DCM, 0.335 mL, 3.0 eq.) dropwise at ° 0 C. The resulting suspension was stirred at room temperature for 30 min. The reaction was quenched with methanol at ° 0 C. The crude product obtained after solvent evaporation was purified by preparative HPLC to get 2-(3-{5-[(1H-benzotriazol-1-yl)methyl]-5H-pyrrolo[3,2-c]pyridin-2-yl}-4-fluorophenoxy)ethan-1-ol (Compound XIX) as an off white solid (80 mg, 20%).

$^1H$ NMR (400 MHz, DMSO-d6) δ ppm: 9.19 (s, 1H), 8.27 (J=8.4 Hz, 1H), 8.20-8.15 (m, 1H), 8.13 (d, J=8.4 Hz, 1H), 7.87 (dd, J=6.4 Hz, 1H), 7.72-7.63 (m, 1H), 7.60 (d, J=6.8 Hz, 1H), 7.50-7.42 (m, 1H), 7.40 (s, 2H), 7.26-7.12 (m, 2H), 6.92-8.84 (m, 1H), 4.95-4.83 (m, 1H), 4.03-3.97 (m, 2H), 3.75-3.68 (m, 2H).

ES+MS m/z: 404.3 (M+1).

Synthesis of 2-(4-fluoro-3-(5-((6-methyl-1,3-benzothiazol-2-yl)methyl)-5H-pyrrolo[3,2-c]pyridin-2-yl)phenoxy)ethan-1-ol (Compound XXIX)

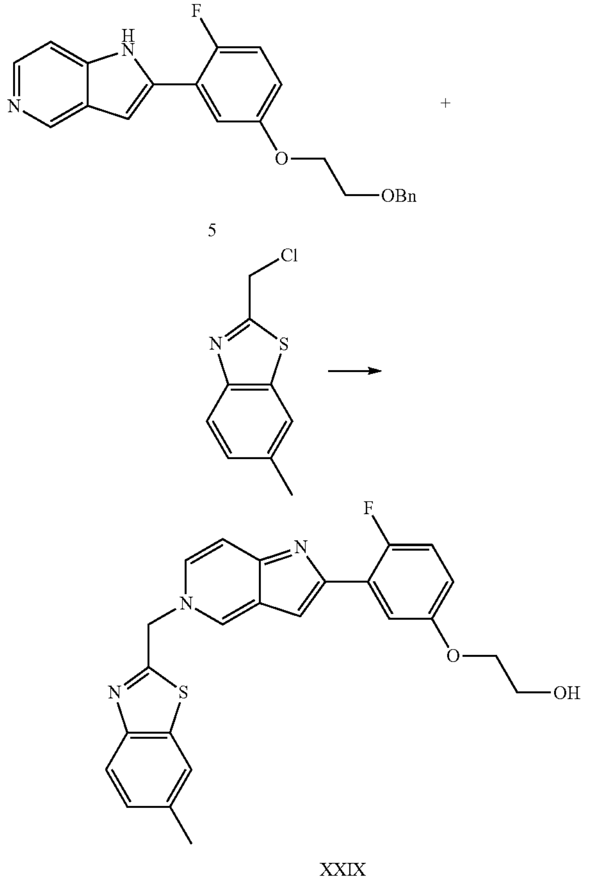

XXIX

To a solution of 2-{5-[2-(benzyloxy)ethoxy]-2-fluorophenyl}-1H-pyrrolo[3,2-c]pyridine 5 (0.300 g, 1.0 eq.) in DMF (4.2 mL, 14 V) was added NaOH (29 mg, 0.9 eq. 30% Solution) and DIPEA (0.360 mL, 2.5 eq.) at 0° C. After 10 min stirring, 2-(chloromethyl)-6-methyl-1,3-benzothiazole (0.179 g, 1.1 eq.) was added. The resulting brown solution was gradually warmed to ambient temperature and stirred for another 16 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get benzylated XXIX (0.180 g, 42%).

To a solution of this intermediate (0.180 g) in DCM (6 mL, 20 V) was added $BCl_3$ (1.0 M in DCM, 0.120 mL) dropwise at 0° C. The resulting suspension was stirred at room temperature for 30 min. The reaction was quenched with methanol at 0° C. The crude product obtained after solvent evaporation was purified by preparative HPLC to get 2-(4-fluoro-3-(5-((6-methyl-1,3-benzothiazol-2-yl)methyl)-5H-pyrrolo[3,2-c]pyridin-2-yl)phenoxy)ethan-1-ol (Compound XXIX) as an off white solid (40 mg, 27%).

$^1H$ NMR (400 MHz, DMSO-d6) 5 ppm: 8.98 (s, 1H), 8.01-7.89 (m, 4H), 7.61 (s, 1H), 7.34 (s, 1H), 7.20 (m, 2H), 6.88 (m, 1H), 6.10 (s, 2H), 4.89 (t, 1H), 4.03 (t, 2H), 3.74 (t, 2H), 2.42 (s, 3H).

ES+MS m/z: 434.7 (M+1).

Example 12. Synthesis Compound XX

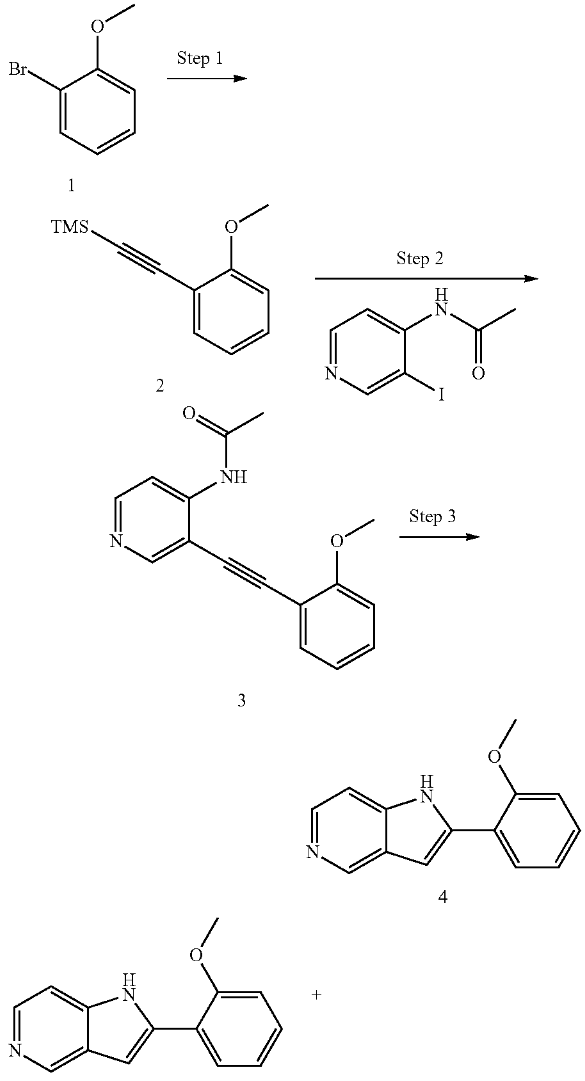

1

2

3

4

4

-continued

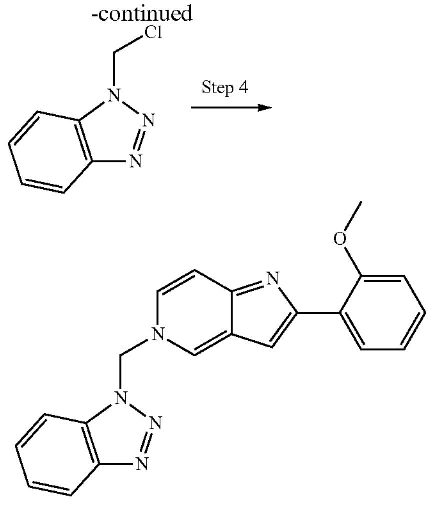

XX

Step 1

The stirred solution of 1-bromo-2-methoxybenzene (2.0 g, 1.0 eq.) and TMS-Acetylene (2.2 mL, 1.5 eq.) in TEA: THF 1:1 (20 V) was purged with argon during 10 min. Copper(I) iodide (0.101 g, 0.05 eq.) and bis(triphenylphosphine)palladium(II) dichloride (0.750 g, 0.1 eq.) were added subsequently under inert atmosphere. The resulting black solution was stirred at 100° C. for 2 h. The reaction was quenched with water. The mixture was extracted with ethyl acetate. The separated organic layer was washed with brine, dried over $Na_2SO_4$ and concentrated under reduced pressure. The crude product was purified by column chromatography to get intermediate 2 (0.753 g, 86%).

Step 2

To the stirred solution of 2 (0.500 g, 1.0 eq.) and N-(3-iodopyridin-4-yl)acetamide (0.641 g, 1.0 eq.) in THF (2.5 mL, 5 V) was added triethylamine (2.5 mL, 5 V). The resulting brown solution was purged with argon during 15 min. Copper(I) iodide (0.046 g, 0.01 eq.) and bis(triphenylphosphine)palladium(II) dichloride (0.172 g, 0.1 eq.) were subsequently added under inert atmosphere. Then TBAF (1.0 M in THF, 2.1 mL, 1.5 eq.) was added. The resulting black solution was stirred at 50° C. for 12 h. The reaction mixture was diluted with dichloromethane (10 V) and filtered through celite pad. The filtrate was concentrated and purified by column chromatography using ethyl acetate and hexane as mobile phase to get N-{3-[(2-methoxyphenyl) ethynyl] pyridin-4-yl}acetamide 3 (0.410 g, 80%).

Step 3

To the stirred solution of N-{3-[(2-methoxyphenyl)ethynyl]pyridin-4-yl} acetamide 3 (0.212 g, 1.0 eq.), in DMF (3.6 mL, 30 V) was added $K_2CO_3$ (0.220 g, 2.0 eq.). The resulting solution was stirred at 85° C. for 12 h. The reaction mixture was diluted with dichloromethane (10 V) and filtered through celite pad. Celite plug was washed with DCM (5 V×2). Combined organic layer was washed with saturated ammonium chloride solution (10 V) followed by brine (10 V). The organic layer was dried over anhydrous $Na_2SO_4$ and concentrated under reduced pressure. The crude product was purified by flash column chromatography using ethyl acetate and hexane as mobile phase to get 2-(2-methoxyphenyl)-1H-pyrrolo[3,2-c]pyridine 4 (125 mg). $^1$H NMR (400 MHz, DMSO-d6) δ ppm: 12.4 (br s, 1H), 7.90 (d, 1H), 7.65 (t, 1H), 7.35 (m, 2H), 7.15 (t, 1H), 4.02 (s, 3H); ES+MS m/z: 225.2 (M+1).

Step 4

To a solution of 2-(2-methoxyphenyl)-1H-pyrrolo[3,2-c]pyridine 4 (0.400 g, 1.0 eq.) in DMF (5.6. mL, 14 V) was added NaOH (61 mg, 0.9 eq. 30% solution) and DIPEA (0.773 mL, 2.5 eq.) at 0° C. After 10 min stirring, 1-(chloromethyl)-1H-benzotriazole (0.327 g, 1.1 eq.) was added. The resulting brown solution was gradually warmed to ambient temperature and stirred for another 20 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get 1-{[2-(2-methoxyphenyl)-5H-pyrrolo[3,2-c]pyridin-5-yl]methyl}-1H-benzotriazole XX (16 mg, 3%). $^1$H NMR (400 MHz, DMSO-d6) δ ppm: 9.03 (s, 1H), 8.39 (d, J=6.8 Hz, 1H), 8.26 (d, J=8 Hz, 1H), 8.12 (d, J=8 Hz, 1H), 8.06 (d, J=6 Hz, 1H), 7.70 (t, 1H), 7.46 (d, 2H), 7.36 (m, 3H), 7.26 (m, 1H), 7.09 (d, 1H), 7.00 (t, 1H), 3.92 (s, 3H). ES+MS m/z: 356.3 (M+1).

Example 13. Synthesis of Compounds XXI, XXVI and XXX

Preparation of (2-(1H-pyrrolo[3,2-c]pyridin-2-yl)phenyl)methanol 6, Common Intermediate

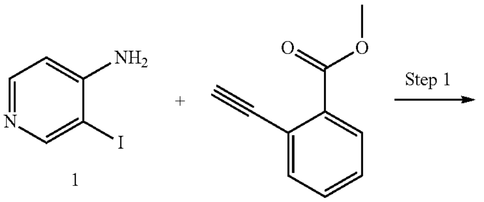

1

2

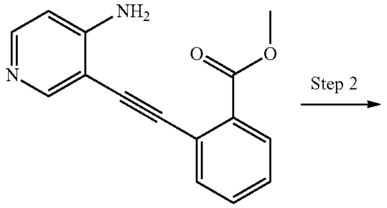

3

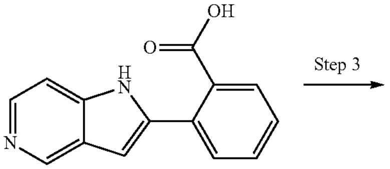

4

-continued

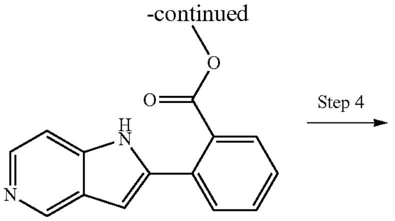

5

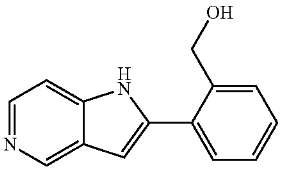

6

Step 1

The stirred solution of 3-iodopyridin-4-amine (0.5 g, 1.0 eq.) and methyl 2-ethynylbenzoate (0.36 g, 1.0 eq.) in THF:TEA 1:1 (10 mL, 20 V) was purged with argon during 15 min. Copper(I) iodide (0.021 g, 0.05 eq.) and bis(triphenylphosphine)palladium(II) dichloride (0.16 g, 0.1 eq.) were added subsequently under inert atmosphere. The resulting black solution was stirred at 90° C. for 6 h. The reaction mixture was diluted with dichloromethane (100 mL) and filtered through celite pad. Filtrate was washed with water (50 mL) and concentrated. The crude product was purified by column chromatography using ethyl acetate and hexane as mobile phase to get methyl 2-((4-aminopyridin-3-yl)ethynyl)benzoate 3 as a thick brown liquid (0.64 g, 81%).

Step 2

To the stirred solution of methyl 2-((4-aminopyridin-3-yl)ethynyl)benzoate 3 (0.64 g, 1.0 eq.) in 1,4-dioxane (6.4 mL, 10 V) was added potassium tert-butoxide (0.55 g, 2.0 eq.). The resulting solution was stirred at 85° C. for 2 h. The reaction mixture was diluted with dichloromethane (50 V) and filtered through celite pad. Celite plug was washed with DCM (5 V×2). Combined organic layers were concentrated under reduced pressure to get crude 4 (700 mg crude). The compound was taken to next step without further purification.

Step 3

The suspension of 2-(1H-pyrrolo[3,2-c]pyridin-2-yl)-benzoic acid 4 (0.7 g, 1.0 eq.) in methanol (7.0 mL, 10 V) was cooled to 0° C. and $SO_2Cl_2$ (0.65 mL, 3.0 eq.) was added slowly. The reaction was allowed to warm to room temperature and stirred for 12 h. TLC showed the disappearance of starting material. Reaction mass was concentrated under reduced pressure. The remaining mass was diluted with dichloromethane, washed with saturated bicarbonate solution and concentrated under reduced pressure. The crude product was purified by column chromatography to get methyl 2-(1H-pyrrolo[3,2-c]pyridin-2-yl)benzoate 5 as a brown solid (0.332 g, 44%).

Step 4

The stirred solution of methyl 2-(1H-pyrrolo[3,2-c]pyridin-2-yl)benzoate 5 (0.33 g, 1.0 eq.) in THF (15 mL, 50 V)

was cooled to −5° C. and LAH (0.15 g, 3.0 eq.) was added portion wise. The resulting reaction mass was stirred at room temperature for 2 h. TLC showed the disappearance of starting material. Reaction mass was quenched with eq. ammonium chloride solution and extracted with dichloromethane (10% MeOH). The organic layer was filtered through celite pad and the filtrate was concentrated under reduced pressure. Crude product was purified by column chromatography to get of (2-(1H-pyrrolo[3,2-c]pyridin-2-yl)phenyl)methanol 6 as light yellow solid (250 mg, 83%).

Preparation of (2-(5-((1H-Benzotriazol-1-yl)methyl)-5H-pyrrolo[3,2-c]pyridin-2-yl)phenyl)methanol (Compound XXI)

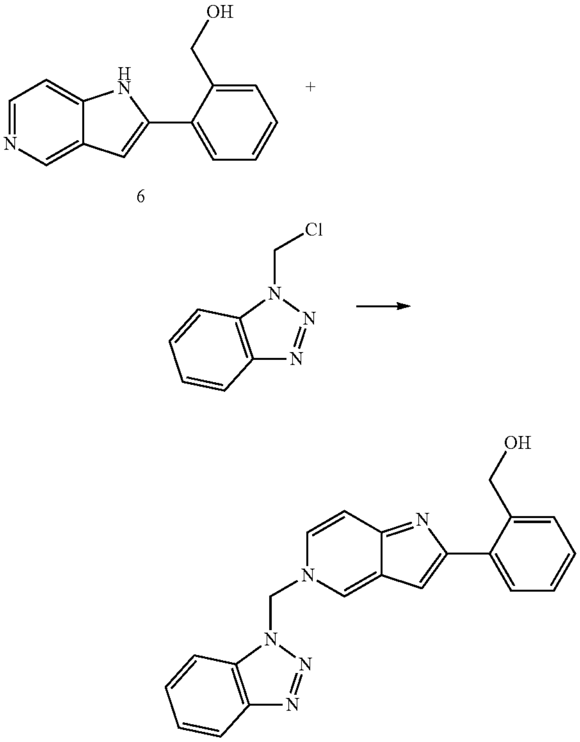

6

XXI

To a solution of (2-(1H-pyrrolo[3,2-c]pyridin-2-yl)phenyl)methanol 6 (0.25 g, 1.0 eq.) in DMF (3.5 mL, 14 V) was added NaOH (40 mg, 0.9 eq. 30% solution) and DIPEA (0.52 mL, 2.5 eq.) at 0° C. After 10 min stirring, 1-chloromethyl-1H-benzotriazole (0.205 g, 1.1 eq.) was added. The resulting brown solution was gradually warmed to ambient temperature and stirred for another 16 h. The reaction mixture was diluted with ice cold water (10 mL). The precipitated product was collected by filtration, washed with diethyl ether and cold methanol and dried to get (2-(5-((1H-Benzotriazol-1-yl)methyl)-5H-pyrrolo[3,2-c]pyridin-2-yl)phenyl)methanol (Compound XXI) as off-white solid (68 mg, 14%). $^1$H NMR (400 MHz, DMSO-d6) δ ppm: 9.22 (s, 1H), 8.29 (d, J=8.4, 1H), 8.20 (d, 1H), 8.13 (d, J=8.4, 1H), 7.79 (d, 1H), 7.06-7.77 (m, 2H), 7.60 (d, 1H), 7.5 (t, 1H), 7.41 (s, 1H), 7.39 (m, 2H), 7.26-7.8 (m, 2H), 7.1 (s, 1H), 4.42 (s, 2H). ES+MS m/z: 356.3 (M+1).

Preparation of (2-(5-((5-methyl-1,3-benzoxazol-2-yl)methyl)-5H-pyrrolo[3,2-c]pyridin-2-yl)phenyl)methanol (Compound XXVI)

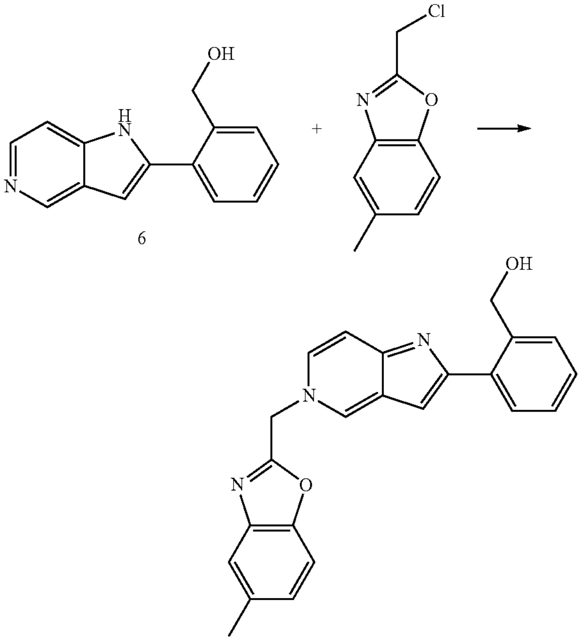

6

XXVI

To a solution of (2-(1H-pyrrolo[3,2-c]pyridin-2-yl)phenyl)methanol 6 (0.20 g, 1.0 eq.) in DMF (2.8 mL, 14 V) was added NaOH (32 mg, 0.9 eq. 30% solution) and DIPEA (0.42 mL, 2.5 eq.) at 0° C. After 10 min stirring, 2-(chloromethyl)-5-methyl-1,3-benzoxazole (0.178 g, 1.1 eq.) was added. The resulting brown solution was gradually warmed to ambient temperature and stirred for another 16 h. The reaction mixture was diluted with ice cold water (10 mL). The precipitated product was collected by filtration, washed with diethyl ether and cold methanol and dried to get (2-(5-((5-methyl-1,3-benzoxazol-2-yl)methyl)-5H-pyrrolo[3,2-c]pyridin-2-yl)phenyl)methanol (Compound XXVI) as pale brown solid (23 mg, 7%).

$^1$H NMR (400 MHz, DMSO-d6) 5 ppm: 9.01 (s, 1H), 8.00-8.15 (m, 2H), 8.82 (d, J=6.8, 1H), 7.60-7.70 (m, 2H), 7.52 (s, 1H), 7.20-7.45 (m, 4H), 7.09 (s, 1H), 6.07 (s, 2H), 4.47 (s, 2H), 2.39 (s, 3H).

ES+MS m/z: 370.3 (M+1).

Preparation of (2-{5-[(6-methyl-1,3-benzothiazol-2-yl)methyl]-5H-pyrrolo[3,2-c]pyridin-2-yl}phenyl)methanol (Compound XXX)

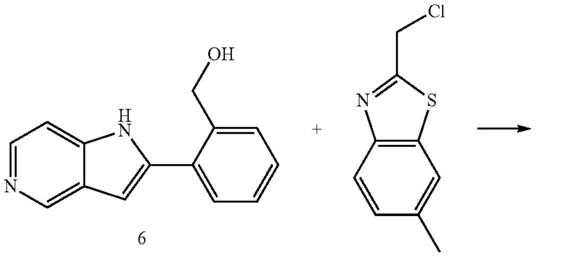

6

-continued

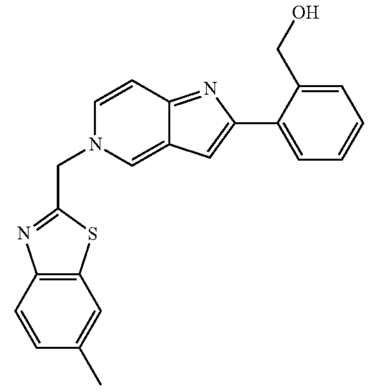

XXX

To a solution of (2-(1H-pyrrolo[3,2-c]pyridin-2-yl)phenyl)methanol 6 (0.170 g, 1.0 eq.) in DMF (2.38 mL, 14 V) was added NaOH (27 mg, 0.9 eq. 30% solution) and DIPEA (0.329 mL, 2.5 eq.) at 0° C. After 10 min stirring, 2-(chloromethyl)-6-methyl-1,3-benzothiazole (0.164 g, 1.1 eq.) was added. The resulting brown solution was gradually warmed to ambient temperature and stirred for another 16 h. The reaction was diluted with ethyl acetate (15 V) and washed with water (2 V). The organic layer was separated, dried over $Na_2SO_4$ and concentrated under reduced pressure. The crude was purified by column chromatography using ethyl acetate and hexane as mobile phase to get (2-{5-[(6-methyl-1,3-benzothiazol-2-yl)methyl]-5H-pyrrolo[3,2-c]pyridin-2-yl}phenyl)methanol (Compound XXX) as a pale yellow solid (82 mg, 28%). $^1$H NMR (400 MHz, DMSO-d6) δ ppm: 9.05 (s, 1H), 8.07 (d, 1H), 8.03 (br s, 1H), 7.90-7.81 (m, 3H), 7.64 (d, 1H), 7.41-7.28 (m, 4H), 7.08 (s, 1H), 6.14 (s, 2H), 4.46 (s, 2H), 2.42 (s, 3H). ES+MS m/z: 386.6 (M+1).

Example 14. Synthesis of Compound XXII

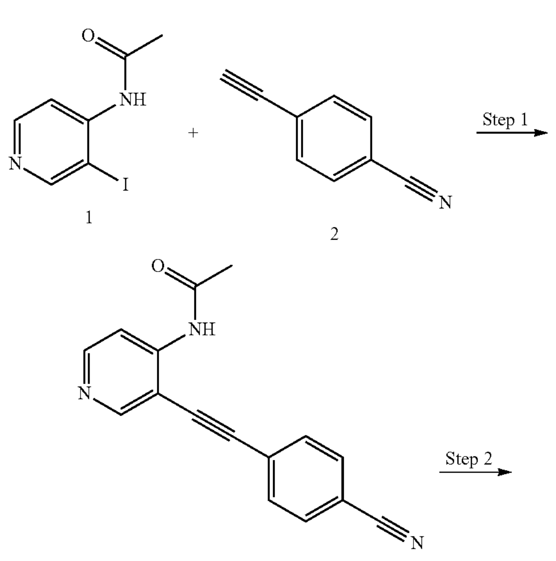

1 + 2

3

-continued

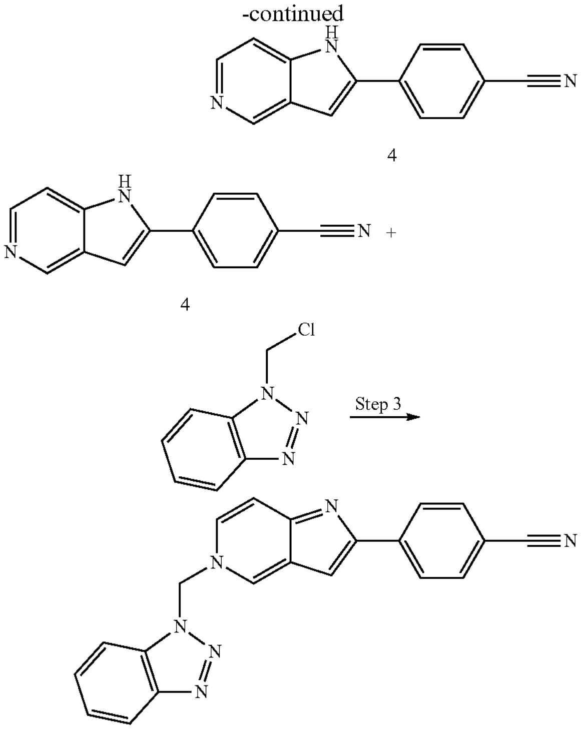

4

4 +

XXII

Step 1

To a solution of N-(3-iodopyridin-4-yl)acetamide (1.0 g, 1.0 eq.) and 4-ethynylbenzonitrile (0.484 g, 1.0 eq.) in TEA:THF 1:1 (10 mL, 10V) was added copper(I) iodide (0.036 g, 0.05 eq.) and bis(triphenylphosphine)palladium(II) dichloride (0.266 g, 0.1 eq.) subsequently. The resulting brown solution was stirred at 90° C. for 8 h. The reaction mixture was diluted with ethyl acetate and filtered through celite pad. The filtrate was concentrated under reduced pressure. Crude was purified by column chromatography using ethyl acetate and hexane as mobile phase to get N-{3-[(4-cyanophenyl)ethynyl]pyridin-4-yl}acetamide 3 (0.840 g, 84%).

Step 2

To the stirred solution of N-{3-[(4-cyanophenyl)ethynyl]pyridin-4-yl}acetamide 3 (0.440 g, 1.0 eq.) in DMF (4.2 mL, 10 V) was added $K_2CO_3$ (0.465 g, 2.0 eq.). The resulting solution was stirred at 100° C. for 4 h. The reaction mixture was diluted with dichloromethane (10 V) and filtered through celite pad. Celite plug was washed with DCM (5 V×2). Combined organic layer was washed with saturated ammonium chloride solution (10 V) followed by brine (10 V). The organic layer was dried over anhydrous $Na_2SO_4$ and concentrated under reduced pressure. Crude was purified by flash column chromatography using ethyl acetate and hexane as a mobile phase to get 4-(1H-pyrrolo[3,2-c]pyridin-2-yl)benzonitrile 4 (300 mg, 81%).

$^1$H NMR (400 MHz, DMSO-d6) δ ppm: 12.51 (brs, 1H), 9.05 (s, 1H), 8.30 (s, 1H), 8.20 (s, 2H), 8.10 (s, 2H), 8.75 (s, 1H), 8.38 (s, 1H).

ES+MS m/z: 220.2 (M+1).

Step 3

To the solution of 4-(1H-pyrrolo[3,2-c]pyridin-2-yl)benzonitrile 4 (0.300 g, 1.0 eq.) in DMF (1.5 mL, 5 V) was added DIPEA (1.5 mL, 5V) under inert atmosphere. After 5 min stirring, 1-(chloromethyl)-1H-benzotriazole (0.251 g, 1.1 eq.) was added. The reaction was stirred at ambient temperature for 20 h. The reaction mixture was diluted with water and extracted with dichloromethane. The separated organic layer was concentrated under reduced pressure. The crude was purified by preparative HPLC to get 4-{5-[(1H-benzotriazol-1-yl)methyl]-5H-pyrrolo[3,2-c]pyridin-2-yl}benzonitrile (Compound XXII) as an off white solid (103 mg, 21%).

$^1$H NMR (400 MHz, DMSO-d6) δ ppm: 9.64 (s, 1H), 8.60 (d, J=6.8 Hz, 1H), 8.31 (d, J=8.4 Hz, 1H), 8.23 (d, J=8 Hz, 2H), 8.14 (d, J=8.4 Hz, 1H), 7.99 (d, J=8 Hz, 2H), 7.91 (d, J=6.8 Hz, 1H), 7.73 (t, 1H), 7.66 (s, 1H), 7.55 (s, 2H), 7.51 (t, 1H).

ES+MS m/z: 351.5 (M+1).

Example 15. Synthesis of Compounds XXIII, XXVII, XXXI and XXXIV

Preparation of 2-(2-methoxypyridin-3-yl)-1H-pyrrolo[3,2-c]pyridine 4, Common Intermediate

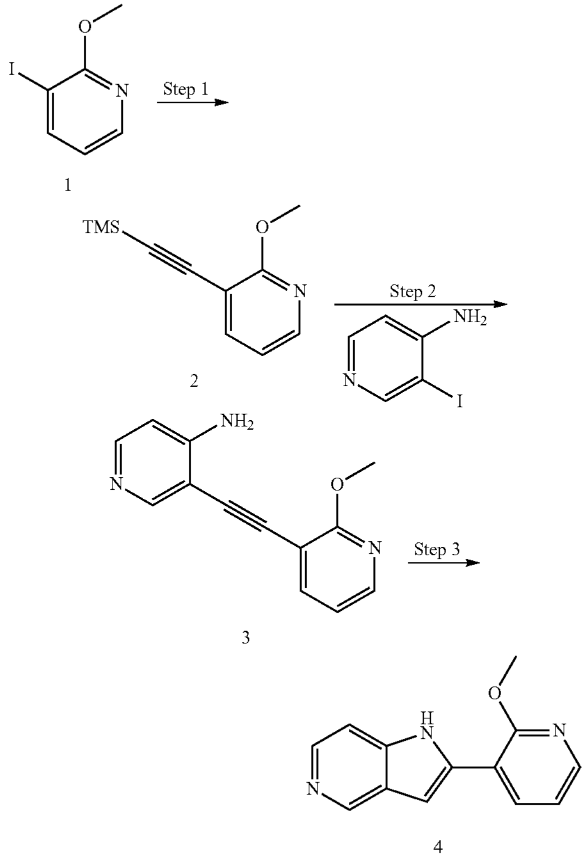

1

2

3

4

Step 1

The stirred solution of 3-iodo-2-methoxypyridine (1.0 g, 1.0 eq.) and TMS-acetylene (0.895 mL, 1.5 eq.) in TEA:THF 1:1 (20 mL, 20 V) was purged with argon during 10 min. Copper(I) iodide (0.040 mg, 0.05 eq.) and bis(triphenylphosphine)palladium(II) dichloride (0.298 g, 0.1 eq.) were added subsequently under inert atmosphere. The resulting black solution was stirred at 100° C. for 2 h. The reaction was quenched with water and the mixture was extracted with ethyl acetate. The separated organic layer washed with brine, dried over $Na_2SO_4$ and concentrated under reduced pressure. The crude product was purified by column chromatography to get intermediate 2 (0.753 g, 88%).

Step 2

The stirred solution of intermediate 2 (0.320 g, 1.0 eq.) and 3-iodopyridin-4-amine (0.358 g, 1.2 eq.) in TEA:THF 1:1 (3 mL, 10 V) was purged with argon during 15 min. Copper(I) iodide (0.038 g, 0.05 eq.) and bis(triphenylphosphine)palladium(II) dichloride (0.102 g, 0.1 eq.) were added subsequently, followed by TBAF (1.0 M in THF, 2.175 mL, 1.5 eq.). The resulting brown solution was stirred at 50° C. for 4 h. The reaction was diluted with DCM and filtered through celite pad. The filtrate was concentrated under reduced pressure. The crude product was purified by column chromatography using ethyl acetate and hexane as mobile phase to get 3-[(2-methoxypyridin-3-yl)ethynyl]pyridin-4-amine 3 (280 mg, 85%).

Step 3

To the stirred solution of 3-[(2-methoxypyridin-3-yl)ethynyl]pyridin-4-amine 3 (0.280 g, 1.0 eq.) in 1,4-dioxane (2.6 mL, 10 V) was added potassium tert-butoxide (0.278 g, 2.0 eq.). The resulting solution was stirred at 85° C. for 4 h. The reaction mixture was diluted with dichloromethane (10 V) and filtered through celite pad. Celite plug was washed with DCM (5 V×2). Combined organic layer was washed with saturated ammonium chloride solution (10 V) followed by brine (10 V). The separated organic layer was dried over anhydrous $Na_2SO_4$ and concentrated under reduced pressure. Crude product was purified by flash column chromatography using ethyl acetate and hexane as mobile phase to get 2-(2-methoxypyridin-3-yl)-1H-pyrrolo[3,2-c]pyridine 4 (210 mg, 75%).

Preparation of 1-((2-(2-methoxypyridin-3-yl)-5H-pyrrolo[3,2-c]pyridin-5-yl)methyl)-1H-benzotriazole (Compound XXIII)

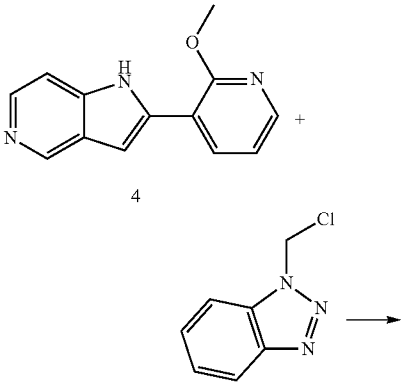

4

-continued

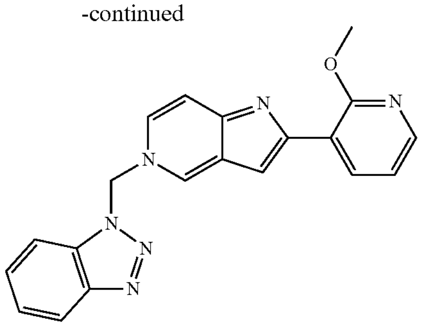

XXIII

To the solution of 2-(2-methoxypyridin-3-yl)-1H-pyrrolo[3,2-c]pyridine 4 (0.200 g, 1.0 eq.) in DMF (1 mL, 5 V) was added DIPEA (1 mL, 5V) under inert atmosphere. After 5 min stirring, 1-(chloromethyl)-1H-benzotriazole (0.163 g, 1.1 eq.) was added. The resulting reaction was stirred at room temperature for 20 h. The reaction mixture was diluted with water and extracted with dichloromethane. The separated organic layer was concentrated.

The crude was purified by preparative HPLC to get 1-((2-(2-methoxypyridin-3-yl)-5H-pyrrolo[3,2-c]pyridin-5-yl)methyl)-1H-benzotriazole (Compound XXII) (85 mg, 19%). $^1$H NMR (400 MHz, DMSO-d6) δ ppm: 9.16 (s, 1H), 8.66 (dd, J=8.8 Hz, 1H), 8.72 (d, J=8.4 Hz, 1H), 8.15-8.10 (m, 3H), 7.71 (t, 1H), 7.54 (d, J=7.2 Hz, 1H), 7.49-7.43 (m, 2H), 7.38 (s, 2H), 7.09 (dd, J=7.2 Hz, 1H), 4.03 (s, 3H). ES+MS m/z: 357.4 (M+1).

Preparation of 2-((2-(2-methoxypyridin-3-yl)-5H-pyrrolo[3,2-c]pyridin-5-yl)methyl)-5-methyl-1,3-benzoxazole (Compound XXVII)

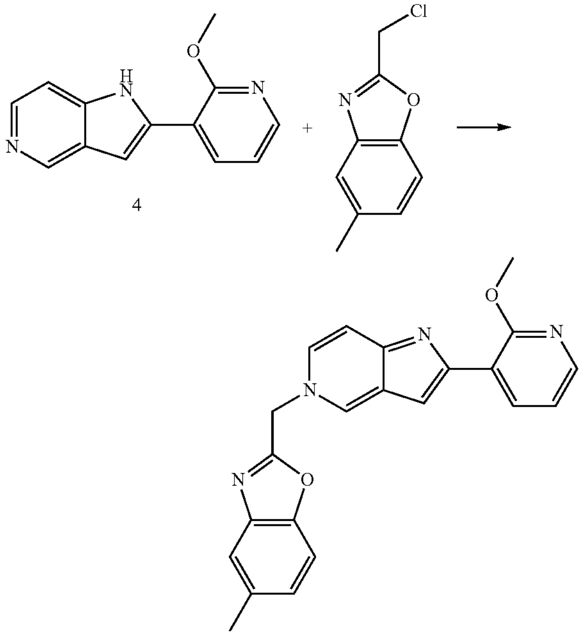

4

XXVII

To a solution 2-(2-methoxypyridin-3-yl)-1H-pyrrolo[3,2-c]pyridine 4 (0.200 g, 1.0 eq.) in DMF (1 mL, 5 V) was added DIPEA (1 mL, 5V) under inert atmosphere. After 10 min stirring, 2-(chloromethyl)-5-methyl-1,3-benzoxazole (0.177 g, 1.1 eq.) was added. The resulting brown solution was gradually warmed to ambient temperature and stirred for another 16 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get 2-((2-(2-methoxypyridin-3-yl)-5H-pyrrolo[3,2-c]pyridin-5-yl)methyl)-5-methyl-1,3-benzoxazole (Compound XXVII) as a pale yellow solid (70 mg, 21%).

$^1$H NMR (400 MHz, DMSO-d6) δ ppm: 8.88 (s, 1H), 8.80-8.68 (m, 1H), 8.11 (s, 1H), 8.00-7.90 (m, 1H), 7.70-7.30 (m, 4H), 7.28-7.20 (m, 1H), 7.15-7.05 (m, 1H), 6.01 (s, 2H), 4.04 (s, 3H), 2.39 (s, 3H).

ES+MS m/z: 371.4 (M+1).

Preparation of 2-{[2-(2-methoxypyridin-3-yl)-5H-pyrrolo[3,2-c]pyridin-5-yl]methyl}-6-methyl-1,3-benzothiazole (Compound XXXI)

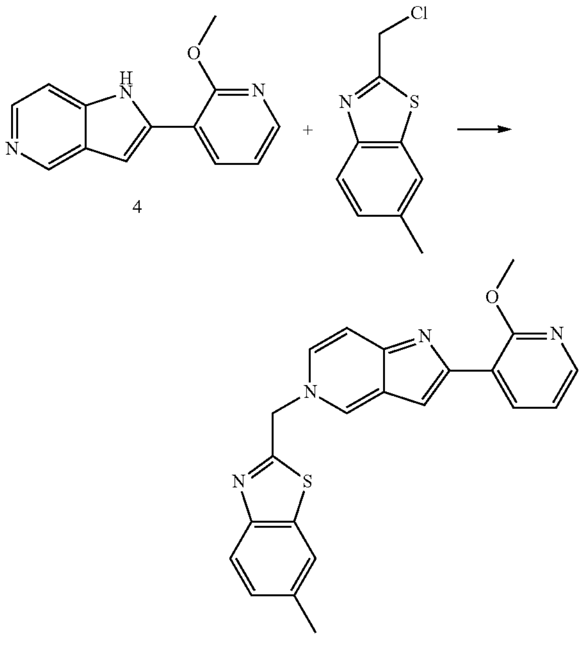

4

XXXI

To a solution 2-(2-methoxypyridin-3-yl)-1H-pyrrolo[3,2-c]pyridine 4 (0.200 g, 1.0 eq.) in DMF (2.8 mL, 14 V) was added NaOH (31 mg, 0.9 eq. 30% solution) and DIPEA (0.386 mL, 2.5 eq.) at 0° C. After 10 min stirring, 2-(chloromethyl)-6-methyl-1,3-benzothiazole (0.192 g, 1.1 eq.) was added. The resulting brown solution was gradually warmed to ambient temperature and stirred for another 16 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get 2-{[2-(2-methoxypyridin-3-yl)-5H-pyrrolo[3,2-c]pyridin-5-yl]methyl}-6-methyl-1,3-benzothiazole (Compound XXXI) as a pale yellow solid (80 mg, 23%).

$^1$H NMR (400 MHz, DMSO-d6) δ ppm: 8.91 (s, 1H), 8.74 (dd, J=7.2 Hz, 1H), 8.11 (dd, 1H), 7.96 (dd. J=7.2 Hz, 1H), 7.88 (t, 2H), 7.53 (d, 1H), 7.40 (s, 1H), 7.34 (d, 1H), 7.10 (dd, J=7.2 Hz, 1H), 6.07 (s, 2H), 4.04 (s, 3H), 2.42 (s, 3H).

ES+MS m/z: 388.13 (M+1).

Preparation of 2-((2-(2-methoxypyridin-3-yl)-5H-pyrrolo[3,2-c]pyridin-5-yl)methyl)-6-methyl-1H-benzoimidazole (Compound XXXIV)

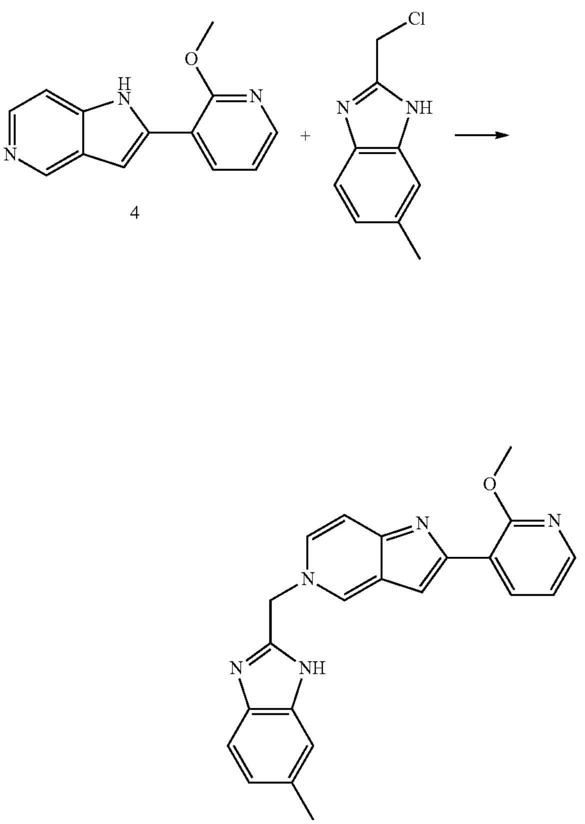

4

XXXIV

To the solution of 2-(2-methoxypyridin-3-yl)-1H-pyrrolo[3,2-c]pyridine 4 (0.200 g, 1.0 eq.) in DMF (1 mL, 5 V) was added DIPEA (1 mL, 5V) under inert atmosphere. After 5 min stirring, 2-(chloromethyl)-6-methyl-1H-benzoimidazole (0.176 g, 1.1 eq.) was added. The reaction was stirred at ambient temperature for 20 h. The reaction mixture was diluted with water and extracted with dichloromethane. The separated organic layer was concentrated under reduced pressure. The crude was purified by preparative HPLC to get 2-((2-(2-methoxypyridin-3-yl)-5H-pyrrolo[3,2-c]pyridin-5-yl)methyl)-6-methyl-1H-benzoimidazole (Compound XXXIV) as a pale yellow solid (79 mg, 24%).

$^1$H NMR (400 MHz, DMSO-d8) δ ppm: 12.62 (s, 1H), 9.05 (s, 1H), 8.62-8.58 (m, 1H), 8.20-8.15 (m, 1H), 8.15-8.05 (m, 1H), 7.70-7.60 (m, 1H), 7.50-7.20 (m, 3H), 7.18-7.10 (m, 1H), 7.05-6.95 (m, 1H), 5.89 (s, 2H), 4.05 (s, 3H), 2.38 (s, 3H).

ES+MS m/z: 370.5 (M+1).

Example 16. Synthesis of Compounds XXIV and XXXII

Preparation of 2-(1,5-dimethyl-1H-pyrazol-4-yl)-1H-pyrrolo[3,2-c]pyridine 4, Common Intermediate

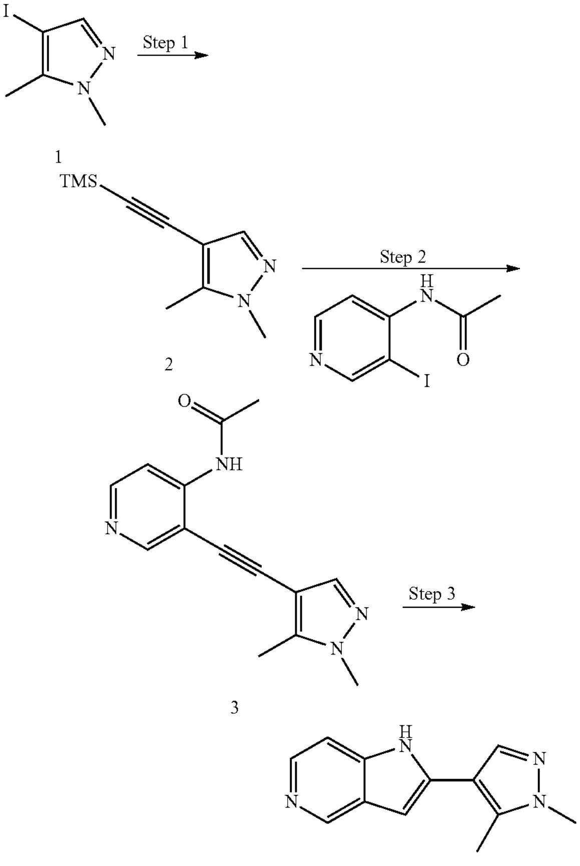

Step 1

The stirred solution of 4-iodo-1,5-dimethyl-1H-pyrazole (1.0 g, 1.0 eq.) and TMS-Acetylene (1.0 mL, 1.5 eq.) in diisopropylamine (10 mL, 10 V) was purged with argon during 10 min. Copper(I) iodide (90 mg, 0.09 eq.) and bis(triphenylphosphine)palladium(II) dichloride (70 mg, 0.02 eq.) were added subsequently under inert atmosphere. The resulting solution was stirred at 100° C. for 2 h. Then the volatiles were evaporated, the remaining mass was diluted with ethyl acetate (100 mL) and filtered through celite pad. The filtrate was washed with water (50 mL×2), dried over $Na_2SO_4$ and concentrated under reduced pressure. The crude product was purified by column chromatography using ethyl acetate and hexane as mobile phase to get 1,5-dimethyl-4-((trimethylsilyl)ethynyl)-1H-pyrazole 2 as a light yellow solid (0.81 g, 93%).

Step 2

The stirred solution of N-(3-iodopyridin-4-yl)acetamide (0.4 g, 1.0 eq.) and 1,5-dimethyl-4-((trimethylsilyl)ethynyl)-1H-pyrazole 2 (0.35 g, 1.0 eq.) in TEA:THF 1:1 (8.0 mL, 20

V) was purged with argon during 10 min. Copper(I) iodide (20 mg, 0.05 eq.) and bis(triphenylphosphine)palladium(II) dichloride (128 mg, 0.1 eq.) were added subsequently followed by tetrabutylammonium fluoride (1.0 M in THF, 2.4 mL, 1.2 eq.) under inert atmosphere. The resulting solution was stirred at ambient temperature for 12 h. Then the volatiles were evaporated, the remaining mass was diluted with ethyl acetate (100 mL) and filtered through celite pad. The filtrate was washed with water (50 mL×2), dried over $Na_2SO_4$ and concentrated under reduced pressure. The crude product was purified by column chromatography using methanol and dichloromethane as mobile phase to get N-(3-((1,5-dimethyl-1H-pyrazol-4-yl)ethynyl)pyridin-4-yl)acetamide 3 as a brown solid (0.26 g, 47%).

Step 3

To the stirred solution of N-(3-((1,5-dimethyl-1H-pyrazol-4-yl)ethynyl)pyridin-4-yl)acetamide 3 (0.26 g, 1.0 eq.) in DMF (2.6 mL, 10 V) was added $K_2CO_3$ (0.28 g, 2.0 eq.). The resulting solution was stirred at 85° C. for 2 h. The reaction mixture was diluted with ethyl acetate (10 V) and filtered through celite pad. Celite plug was washed with ethyl acetate (5 V×2). Combined organic layer was washed with saturated ammonium chloride solution (10 V) followed by brine (10 V). The separated organic layer was dried over anhydrous $Na_2SO_4$ and concentrated under reduced pressure. Crude product was purified by flash column chromatography to get 2-(1,5-dimethyl-1H-pyrazol-4-yl)-1H-pyrrolo[3,2-c]pyridine 4 as off-white solid (0.14 g, 64%).

$^1$H NMR (400 MHz, DMSO-d6) δ ppm: 13.30 (br. s, 1H), 9.09 (s, 1H), 8.30 (d, 1H), 8.01 (d, 1H), 7.95 (d, 1H), 6.93 (s, 1H), 3.90 (s, 3H), 2.52 (s, 3H).

ES+MS m/z: 213.4 (M+1).

Preparation of 1-((2-(1,5-dimethyl-1H-pyrazol-4-yl)-5H-pyrrolo[3,2-c]pyridin-5-yl)methyl)-1H-benzotriazole (Compound XXIV)

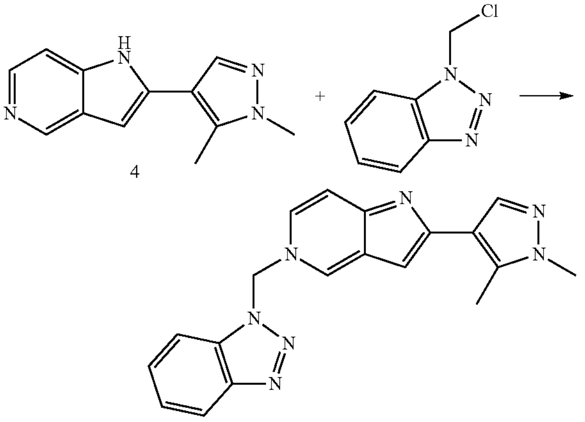

4

XXIV

To a solution of 2-(1,5-dimethyl-1H-pyrazol-4-yl)-1H-pyrrolo[3,2-c]pyridine 4 (0.31 g, 1.0 eq.) in DMF (4.3 mL, 14 V) was added 30% NaOH solution (52 mg, 0.9 eq.) and DIPEA (0.67 mL, 2.5 eq.) at 0° C. After 10 min stirring, 1-chloromethyl-1H-benzotriazole (0.27 g, 1.1 eq.) was added. The resulting brown solution was gradually warmed to ambient temperature and stirred for another 16 h. The reaction mixture was diluted with ethyl acetate (150 mL) and washed with water (50 mL). The organic layer was separated, dried over $Na_2SO_4$ and concentrated under reduced pressure. The crude was purified by column chromatography using methanol and dichloromethane as mobile phase to get 1-((2-(1,5-dimethyl-1H-pyrazol-4-yl)-5H-pyrrolo[3,2-c]pyridin-5-yl)methyl)-1H-benzotriazole (Compound XXIV) as an off-white solid (20 mg, 7%). $^1$H NMR (400 MHz, DMSO-d6) δ ppm: 8.91 (s, 1H) 8.26 (d, J=8.4, 1H), 8.11 (d, J=8.4, 1H), 8.05 (d, 1H), 7.76 (s, 1H), 7.70 (t, 1H), 7.49-7.41 (m, 2H), 7.33 (s, 2H), 6.76 (s, 1H), 3.75 (s, 3H), 2.59 (s, 3H). ES+MS m/z: 344.3 (M+1).

Preparation of 2-{[2-(1,5-dimethyl-1H-pyrazol-4-yl)-5H-pyrrolo[3,2-c]pyridin-5-yl]methyl}-6-methyl-1,3-benzothiazole (Compound XXXII)

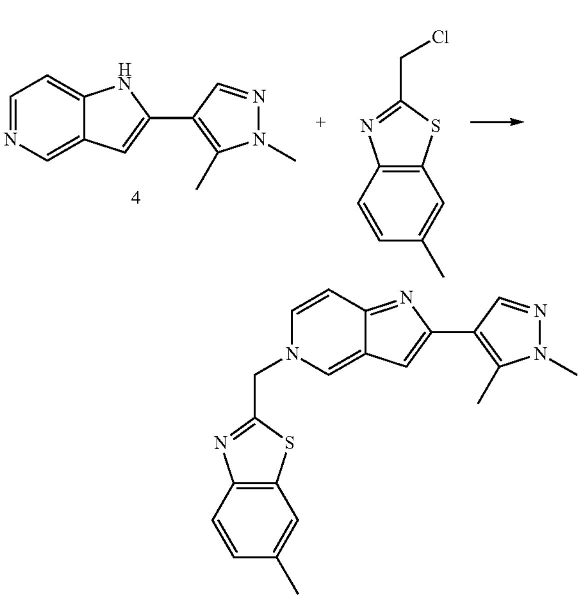

4

XXXII

To a solution of 2-(1,5-dimethyl-1H-pyrazol-4-yl)-1H-pyrrolo[3,2-c]pyridine 4 (0.200 g, 1.0 eq.) in DMF (2.8 mL, 14 V) was added NaOH (33 mg, 0.9 eq. 30% solution) and DIPEA (0.409 mL, 2.5 eq.) at 0° C. After 10 min stirring, 2-(chloromethyl)-6-methyl-1,3-benzothiazole (0.204 g, 1.1 eq.) was added. The resulting brown solution was gradually warmed to ambient temperature and stirred for another 16 h. The reaction mixture was diluted with ethyl acetate (10 V) and washed with water (2 V). The organic layer was separated, dried over $Na_2SO_4$ and concentrated under reduced pressure. The crude was purified by column chromatography using ethyl acetate and hexane as mobile phase to get 2-{[2-(1,5-dimethyl-1H-pyrazol-4-yl)-5H-pyrrolo[3,2-c]pyridin-5-yl]methyl}-6-methyl-1,3-benzothiazole (Compound XXXII) as a pale yellow solid (85 mg, 25%).

$^1$H NMR (400 MHz, DMSO-d6) δ ppm: 8.74 (s, 1H), 7.90-7.85 (m, 3H), 7.78 (s, 1H), 7.46 (d, J=6.8 Hz, 1H), 7.34 (dd, J=8.4 Hz, 1H), 6.05 (s, 1H), 5.75 (s, 2H), 3.76 (s, 3H), 2.63 (s, 3H), 2.42 (s, 3H).

ES+MS m/z: 374.3 (M+1).

Example 17. Synthesis of CPD-1 to CPD-49 (Table 3)

Synthesis of 2-aryl-3H-imidazo[4,5-c]pyridine Intermediates

General Procedure 1:

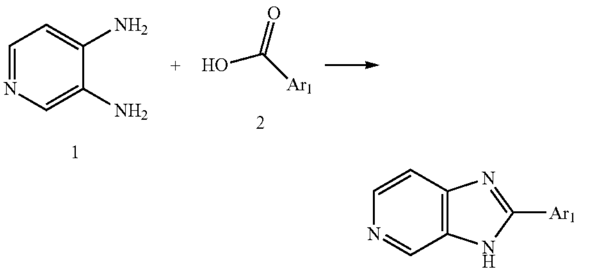

1 2 3

Polyphosphoric acid (4.0 eq.) was heated up to 100° C. and the mixture of aryl-carboxylic acid (1.0 eq.) and pyridine-3,4-diamine (1.0 eq.) was added to it. The mixture was heated to 160° C. and stirred for 12 h. Then the reaction mixture was cooled to room temperature and was slowly added to ice cold aq. ammonia solution (40 V. pH=12). The precipitated solid was filtered and dried under vacuum to obtain 2-aryl-3H-imidazo[4,5-c]pyridine.

Synthesis of 2-(1,5-dimethyl-1H-pyrazol-4-yl)-3H-imidazo[4,5-c]pyridine 3a

3a

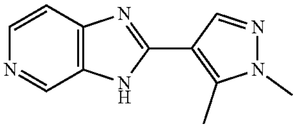

Following general procedure 1, 2-(1,5-dimethyl-1H-pyrazol-4-yl)-3H-imidazo[4,5-c]pyridine 3a was obtained as off-white solid (63 g, 75%). $^1$H NMR (400 MHz, DMSO-d6) δ ppm: 12.88 (bra, 1H), 8.85 (m, 1H), 8.25 (d, 1H), 8.03 (s, 1H), 7.56 (m, 1H), 3.82 (s, 3H), 2.71 (s, 3H). ES+MS m/z: 214.3 (M+1).

Synthesis of 2-(1,3-dimethyl-1H-pyrazol-4-yl)-3H-imidazo[4,5-c]pyridine 3b

3b

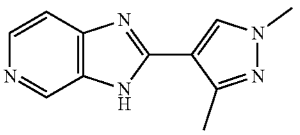

Following general procedure 1, 2-(1,3-dimethyl-1H-pyrazol-4-yl)-3H-imidazo[4,5-c]pyridine 3b was obtained as off-white solid (0.130 g, 33%). $^1$H NMR (400 MHz, DMSO-d6) δ ppm: 12.78 (brs, 1H), 8.84 (brs, 1H), 8.24 (d, 2H), 7.49 (brs, 1H), 3.87 (s, 3H), 2.54 (s, 3H). ES+MS m/z: 214.2 (M+1).

Synthesis of 2-(1,3,5-trimethyl-1H-pyrazol-4-yl)-3H-imidazo[4,5-c]pyridine 3c

3c

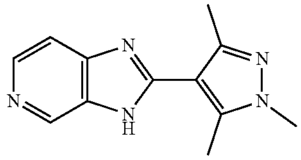

Following general procedure 1, 2-(1,3,5-trimethyl-1H-pyrazol-4-yl)-3H-imidazo[4,5-c]pyridine 3c was obtained as off-white solid (0.140 g, 14%). ES+MS m/z: 228.4 (M+1).

Synthesis of 2-(2-methoxypyridin-3-yl)-3H-imidazo[4,5-c]pyridine 3d

3d

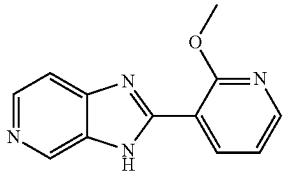

Following general procedure 1, 2-(2-methoxypyridin-3-yl)-3H-imidazo[4,5-c]pyridine 3d was obtained as off-white solid (2.0 g, 49%). $^1$H NMR (300 MHz, DMSO-d6) δ ppm: 12.62 (brs, 1H), 8.98 (s, 1H), 8.69 (dd, $J_1$=7.5 Hz, $J_2$=1.5 Hz, 1H), 8.38 (dd, $J_1$=4.8 Hz, $J_2$=1.8 Hz, 1H), 8.33 (d, J=5.4 Hz, 1H), 7.63 (d, J=5.4 Hz, 1H), 7.24 (dd. $J_1$=7.8 Hz, $J_2$=4.8 Hz, 1H), 4.13 (s, 3H). ES+MS m/z: 227.4 (M+1).

Synthesis of 2-(2-methoxyphenyl-3H-imidazo[4,5-c]pyridine 3e

3e

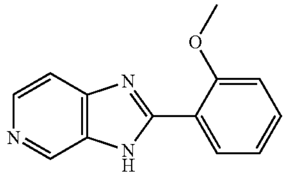

Following general procedure 1, 2-(2-methoxyphenyl)-3H-imidazo[4,5-c]pyridine 3e was obtained as white solid (0.5 g, 67%). $^1$H NMR (400 MHz, DMSO-d6) δ ppm: 12.48 (brs, 1H), 8.95 (s, 1H), 8.42-8.23 (m, 2H), 7.70-7.46 (m, 2H), 7.28 (d, J=8.4 Hz, 1H), 7.15 (t, J=7.6 Hz, 1H), 4.04 (s, 3H). ES+MS m/z: 226.3 (M+1).

Synthesis of 2-(2-(difluoromethoxy)phenyl-3H-imidazo[4,5-c]pyridine 3f

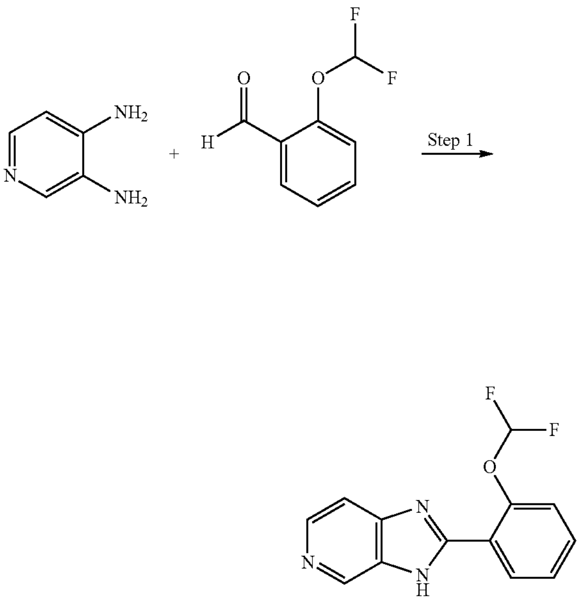

3f

To a stirred solution of 2-(difluoromethoxy)benzaldehyde (1.0 g, 1.0 eq.) in dimethylformamide (8 mL, 8 V) was added sodium bisulfite (0.906 g, 1.5 eq.). After 5 min, pyridine-3,4-diamine (0.633 g, 1.0 eq.) was added slowly. The resulting reaction mass was stirred at 150° C. for 3 h. The reaction mixture was then diluted with water and extracted with ethyl acetate. The separated organic layer was dried over anhydrous sodium sulfate and concentrated. The crude product was purified by column chromatography to obtain 2-(2-(difluoromethoxy)phenyl)-3H-imidazo[4,5-c]pyridine 3f, (0.957 g, 40%). $^1$H NMR (400 MHz, DMSO-d6) δ ppm: 12.82 (brs, 1H), 8.99 (s, 1H), 8.33 (d, J=5.6 Hz, 1H), 8.25-8.12 (m, 1H), 7.73-7.55 (m, 2H), 7.50-7.40 (m, 2H), 7.33 (t, J=73 Hz, 1H). ES+MS m/z: 262.2 (M+1).

Synthesis of 2-(2-fluorophenyl)-3H-imidazo[4,5-c]pyridine 3a

3g

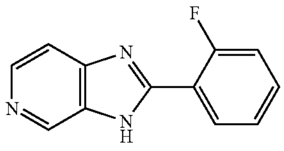

Following general procedure 1, 2-(2-fluorophenyl)-3H-imidazo[4,5-c]pyridine 3g was obtained as off-white solid (15.2 g, 76%). $^1$H NMR (400 MHz, DMSO-d6) δ ppm: 12.98 (s, 1H), 8.99 (s, 1H), 8.34 (d, J=5.2 Hz, 1H), 8.25 (dd, $J_1$=7.6 Hz, $J_2$=6.4 Hz, 1H), 7.72-7.55 (m, 2H), 7.53-7.37 (m, 2H). ES+MS m/z: 214.3 (M+1).

Synthesis of 2-(3-fluorophenyl)-3H-imidazo[4,5-c]pyridine 3 h

3h

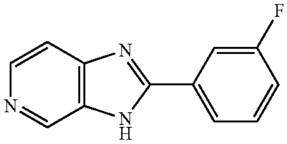

Following general procedure 1, 2-(3-fluorophenyl)-3H-imidazo[4,5-c]pyridine 3 h was obtained as off-white solid (0.83 g, 84%). $^1$H NMR (400 MHz, DMSO-d6) 5 ppm: 8.97 (s, 1H), 8.33 (d, J=5.2 Hz, 1H), 8.08 (d, J=8.0 Hz, 1H), 8.04-7.95 (m, 1H), 7.70-7.58 (m, 2H), 7.45-7.35 (m, 1H). ES+MS m/z: 214.4 (M+1).

Synthesis of 2-(2-fluoro-5-(trifluoromethoxy)phenyl-3H-imidazo[4,5-c]pyridine 3i 3i

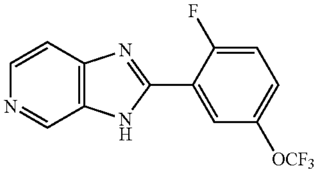

Following general procedure 1, 2-(2-fluoro-5-(trifluoromethoxy)phenyl)-3H-imidazo[4,5-c]pyridine 31 was obtained as off-white solid (3.1 g, 57%).

Synthesis of 2-(5-(2-(benzyloxy)ethoxy)-2-fluorophenyl)-3H-imidazo[4,5-c]pyridine 3j

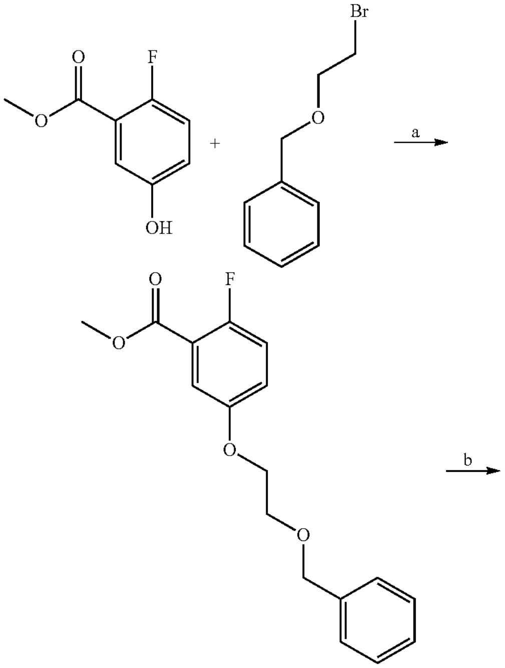

-continued

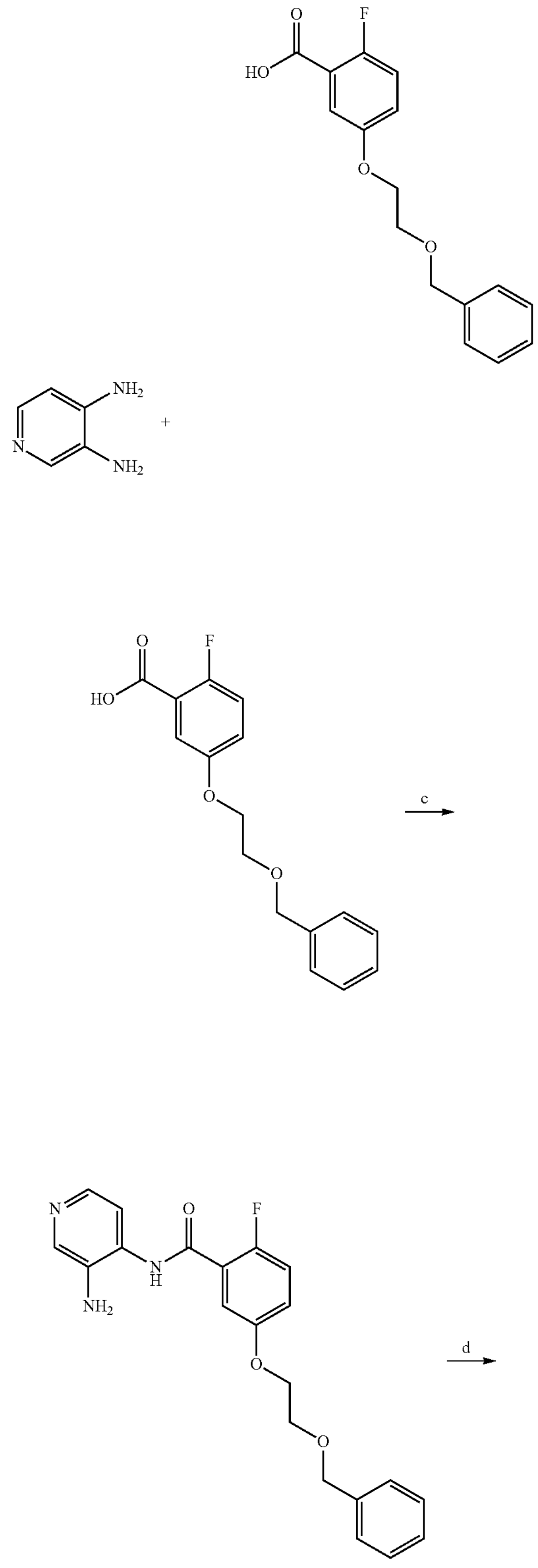

-continued

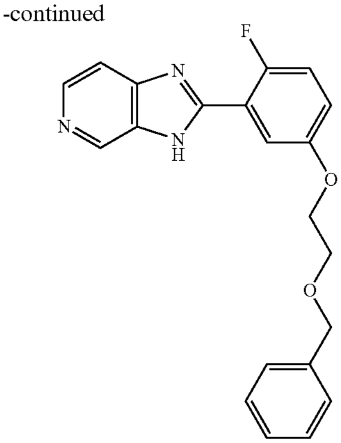

3j a.

To the stirred solution of methyl 2-fluoro-5-hydroxybenzoate (3.0 g, 1.0 eq.) in dimethylformamide (18 mL, 6 V) was added potassium carbonate (7.2 g, 3.0 eq.) under inert atmosphere. To the above solution ((2-bromoethoxy)methyl) benzene (4.5 g, 1.2 eq.) was added. The resulting mixture was stirred at room temperature for 12 h. Then water (10 V) was added and the mixture was extracted with ethyl acetate. The separated organic layer was washed with brine, dried over anhydrous sodium sulfate and concentrated under reduced pressure. The crude was purified by column chromatography to obtain methyl 5-(2-(benzyloxy)ethoxy)-2-fluorobenzoate (4 g, 74%).

b.

Methyl 5-(2-(benzyloxy)ethoxy)-2-fluorobenzoate (2.2 g, 1.0 eq.) was dissolved in methanol (11 mL, 5 V) and sodium hydroxide (1.1 mL 30% aq., 1.5 eq.) was added at 0° C. The reaction was stirred at room temperature for 12 h. Upon consumption of the starting material, solvent was evaporated under reduced pressure. Crude mass was acidified with 1.5N hydrogen chloride and stirred for 10 min. The obtained precipitation was filtered and washed with water to get pure 5-(2-(benzyloxy)ethoxy)-2-fluorobenzoic acid (2.0 g, 95%).

c.

To the stirred solution of 5-(2-(benzyloxy)ethoxy)-2-fluorobenzoic acid (1.9 g, 1.0 eq.) in dimethylformamide (19 ml, 10 V), diisopropylethylamine (3.4 mL, 3.0 eq.) was added at 0° C. After 5 min stirring, 1-ethyl-3-(3-dimethylaminopropyl)carbodiimide hydrochloride (1.88 g, 1.5 eq.) was added followed by pyridine-3,4-diamine (0.71 g, 1.0 eq.). The resulting reaction mixture was stirred at room temperature for 12 h. The reaction was quenched with water and extracted with ethyl acetate. The separated organic layer was washed with brine and concentrated under reduced pressure.

d.

Acetic acid (5 V) was added to the crude product of step c. The mixture was heated to 80° C. and stirred for 2 h. Then the reaction mixture was cooled to room temperature, diluted with water and extracted with ethyl acetate. The separated organic layer was washed with sodium bicarbonate and concentrated under reduced pressure. The crude product was purified by column chromatography to get 2-(5-(2-(benzyloxy)ethoxy)-2-fluorophenyl)-3H-L imidazo [4,5-c]pyridine 3j (1.2 g, 50% over 2 steps). $^1$H NMR (400 MHz, DMSO-d6) δ ppm: 12.96 (s, 1H), 9.01 (s, 1H), 8.34 (d, J=5.6 Hz, 1H), 7.76 (d, J=2.8 Hz, 1H), 7.58 (d, J=5.6 Hz, 1H), 7.48-7.23 (m, 6H), 7.22-7.12 (m, 1H), 4.58 (s, 2H), 4.30-4.20 (m, 2H), 3.85-3.75 (m, 2H). ES+MS m/z: 364.4 (M+1).

Synthesis of 4-(3H-imidazo[4,5-c]pyridin-2-yl)benzonitrile 3k

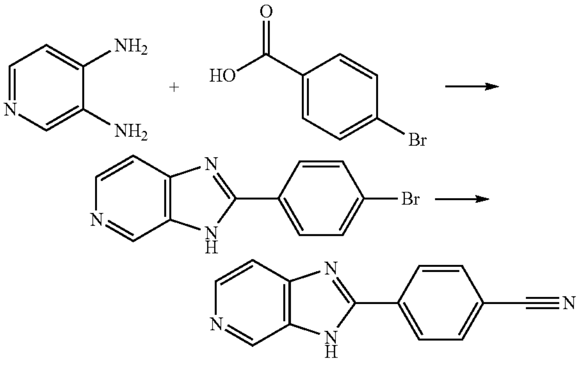

3k

Following general procedure 1, 2-(4-bromophenyl)-3H-imidazo[4,5-c]pyridine was obtained as off-white solid (0.89 g, 72%).

Subsequently, to the mixture of 2-(4-bromophenyl)-3H-imidazo[4,5-c]pyridine (0.500 g, 1.0 eq.), palladium(II) acetate (5 mol %) and xantphos (10 mol %) in dimethylformamide (5 mL, 10 V) was added phosphoryl chloride (0.342 mL, 2.0 eq.) at room temperature under inert atmosphere. The reaction mixture was heated to 140° C. and stirred for 48 h. Then it was cooled to room temperature and was poured into saturated solution of sodium bicarbonate. The product was extracted with diethyl ether (4×20 mL). The combined organic layers were dried over anhydrous sodium sulfate and concentrated under reduced pressure. The crude product was purified by column chromatography to obtain 4-(3H-imidazo[4,5-c]pyridin-2-yl)benzonitrile 3k as solid (180 mg, 45%). $^1$H NMR (400 MHz, DMSO-d6) δ ppm: 13.69 (brs, 1H), 9.02 (s, 1H), 8.40 (dd. $J_1$=6.8 Hz, $J_2$=2 Hz, 2H), 8.34 (d, J=5.6 Hz, 1H), 8.07 (dd, $J_1$=6.8 Hz, $J_2$=2 Hz, 2H), 7.67 (d. J=5.6 Hz, 1H). ES+MS m/z: 221.19 (M+1).

Synthesis of 3-(3H-imidazo[4,5-c]pyridin-2-yl)-N,N-dimethylaniline 31

31

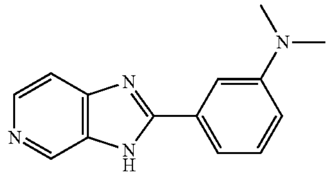

Following general procedure 1, 3-(3H-imidazo[4,5-c]pyridin-2-yl)-N,N-dimethylaniline 31, was obtained as off-white solid (97 mg, 59%). ES+MS m/z: 239.1 (M+1).

Synthesis of (2-(3H-imidazo[4,5-c]pyridin-2-yl)phenyl)methanol 3m

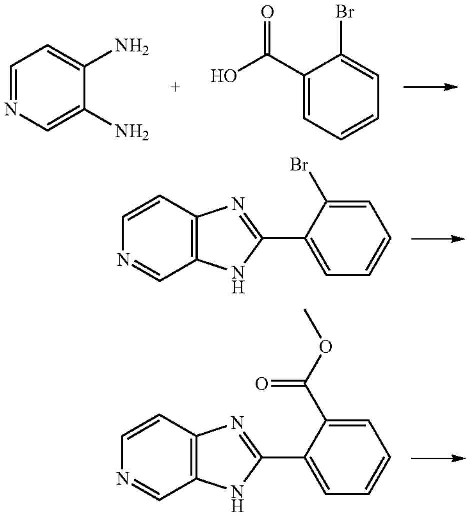

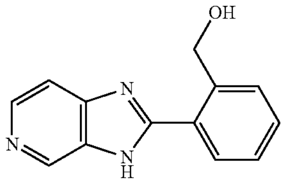

3m

Following general procedure 1, 2-(2-bromophenyl)-3H-imidazo[4,5-c]pyridine was obtained as solid (1.9 g, 72%).

Subsequently, to a solution of 2-(2-bromophenyl)-3H-imidazo[4,5-c]pyridine (0.400 g, 1.0 eq.) in methanol (24 ml, 60 V) potassium acetate (0.284 g, 2.0 eq.), Xantphos (0.167 mg, 0.2 eq.) and $Pd_2(dba)_3$ were added at room temperature. The resulting mixture was stirred under 2 kg/cm$^2$ carbon monoxide pressure at 120° C. for 12 h. The reaction mass was passed through celite, washed with methanol and the filtrate was concentrated. Crude product was purified by column chromatography to obtain methyl 2-(3H-imidazo[4,5-c]pyridin-2-yl)benzoate as white solid (300 mg, 81%).

Then, to a stirred solution of methyl 2-(3H-imidazo[4,5-c]pyridin-2-yl)benzoate (0.300 g, 1.0 eq.) in tetrahydrofuran (30 mL, 100 V) was added lithium aluminium hydride (90 mg, 2.0 eq.) under inert atmosphere at −20° C. The resulting mixture was stirred for 4 h. Then saturated ammonium chloride solution was added and the mixture was extracted with dichloromethane (10% methanol). The separated organic layer was filtered through celite pad. Filtrate was concentrated and the crude was purified by column chromatography to obtain (2-(3H-imidazo[4,5-c]pyridin-2-yl)phenyl)methanol 3m as off-white solid (200 mg, 75%). $^1$H NMR (400 MHz, DMSO-d6) δ ppm: 8.99 (s, 1H), 8.35 (d, J=5.6 Hz, 1H), 7.94 (d, J=7.6 Hz, 1H), 7.69 (d, J=7.6 Hz, 1H), 7.65 (d, J=5.6 Hz, 1H), 7.60-7.52 (m, 1H), 7.52-7.44 (m, 1H), 4.81 (s, 2H). ES+MS m/z: 226.3 (M+1).

Synthesis of 2-(5-methylthiophen-2-yl)-3H-imidazo[4,5-c]pyridine 3n

3n

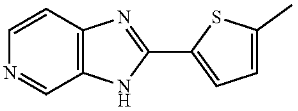

Following general procedure 1, 2-(5-methylthiophen-2-yl)-3H-imidazo[4,5-c]pyridine 3n was obtained as solid (230 mg, 30%). ES+MS m/z: 216.4 (M+1).

Synthesis of 2-(5-methylthiophen-3-yl)-3H-imidazo[4,5-c]pyridine 3o

3o

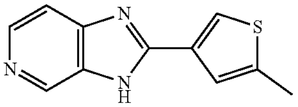

Following general procedure 1, 2-(5-methylthiophen-3-yl)-3H-imidazo[4,5-c]pyridine 30 was obtained as solid (150 mg, 20%).

Synthesis of 2-(4,5-dimethylthiophen-3-yl)-3H-imidazo[4,5-c]pyridine 3p

3p

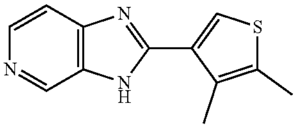

Following general procedure 1, 2-(4,5-dimethylthiophen-3-yl)-3H-imidazo[4,5-c]pyridine 3p was obtained as solid (130 mg, 12%). ES+MS m/z: 230.9 (M+1).

Synthesis of compounds CPD-1 to CPD-49 from 2-aryl-3H-imidazo[4,5-c]pyridine Intermediates General Procedure 2:

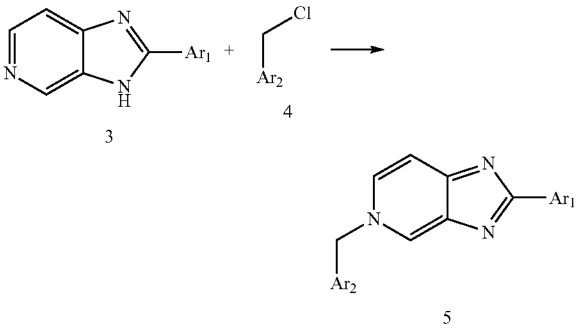

3 4 5

To a solution of 2-aryl-3H-imidazo[4,5-c]pyridine 3 (1.0 eq.) in dimethylformamide (5 V) was added sodium hydroxide (0.9 eq., 30% solution) and diisopropylethylamine (2.5 eq.) at 0° C. After 10 min stirring, 4 (1.2 eq.) was added and the reaction mixture was allowed to warm slowly to room temperature and stirred for 20 h.

In most examples, the reaction mass was added slowly to water (100 V), the precipitated solid was filtered, washed with diethyl ether and dried under vacuum. When necessary, the product was purified by re-precipitation and/or washing with methyl tert-butyl ether or isopropyl alcohol.

Alternatively, the reaction mixture was diluted with ethyl acetate (15 V) and water (2 V). The separated organic layer was washed with brine (2 V), dried over anhydrous sodium sulfate and concentrated under reduced pressure. The crude was purified by column chromatography.

Synthesis of 2-((2-(1,5-dimethyl-1H-pyrazol-4-yl)-5H-imidazo[4,5-c]pyridin-5-yl)methyl)-6-methylbenzo[d]thiazole CPD-1

Following general procedure 2, 2-((2-(1,5-dimethyl-1H-pyrazol-4-yl)-5H-imidazo[4,5-c]pyridin-5-yl)methyl)-6-methylbenzo[d]thiazole CPD-1 was obtained as off-white solid (230 mg, 65%). $^1$H NMR (300 MHz, DMSO-d6) δ ppm: 8.94 (s, 1H), 8.18 (d, J=6.9 Hz, 1H), 8.00-7.80 (m, 3H), 7.66 (d, J=6.6 Hz, 1H), 7.33 (d, J=8.1 Hz, 1H), 6.15 (s, 2H), 3.79 (s, 3H), 2.76 (s, 3H), 2.42 (s, 3H). ES+MS m/z: 375.3 (M+1).

Synthesis of 2-((2-(1,5-dimethyl-1H-pyrazol-4-yl)-5H-imidazo[4,5-c]pyridin-5-yl)methyl)-5-methylbenzo[d]thiazole CPD-2

Following general procedure 2, 2-((2-(1,5-dimethyl-1H-pyrazol-4-yl)-5H-imidazo[4,5-c]pyridin-5-yl)methyl)-5-methylbenzo[d]thiazole CPD-2 was obtained as off-white solid (60 mg, 42%). $^1$H NMR (300 MHz, DMSO-d8) δ ppm: 8.95 (s, 1H), 8.19 (d, J=6.3 Hz, 1H), 8.05-7.88 (m, 2H), 7.99 (s, 1H), 7.66 (d, J=6.6 Hz, 1H), 7.30 (d, J=8.1 Hz, 1H), 6.17 (s, 2H), 3.80 (s, 3H), 2.77 (s, 3H), 2.43 (s, 3H). ES+MS m/z: 375.3 (M+1).

Synthesis of 2-((2-(1,5-dimethyl-1H-pyrazol-4-yl)-5H-imidazo[4,5-c]pyridin-5-yl)methyl)benzo[d]thiazole CPD-3

Following general procedure 2, 2-((2-(1,5-dimethyl-1H-pyrazol-4-yl)-5H-imidazo[4,5-c]pyridin-5-yl)methyl)benzo[d]thiazole CPD-3 was obtained as off-white solid (140 mg, 25%). $^1$H NMR (400 MHz, DMSO-d6) 5 ppm: 8.97 (s, 1H), 8.22 (d, J=6.4 Hz, 1H), 8.13 (d, J=8.0 Hz, 1H), 7.99 (d, J=8.4 Hz, 1H), 7.94 (s, 1H), 7.68 (d, J=6.8 Hz, 1H), 7.50-7.44 (m, 2H), 6.19 (s, 2H), 3.79 (s, 3H), 2.76 (s, 3H). ES+MS m/z: 361.3 (M+1).

Synthesis of 5-chloro-2-((2-(1,5-dimethyl-1H-pyrazol-4-vi)-5H-imidazo[4,5-c]pyridin-5-yl)methyl)benzo[d]thiazole CPD-4

Following general procedure 2, 5-chloro-2-((2-(1,5-dimethyl-1H-pyrazol-4-yl)-5H-imidazo[4,5-c]pyridin-5-yl)methyl)benzo[d]thiazole CPD-4 was obtained as off-white solid (230 mg, 31%). $^1$H NMR (400 MHz, DMSO-d6) 0 ppm: 8.94 (s, 1H), 8.20-8.14 (m, 2H), 8.10 (d, J=2.0 Hz, 1H), 7.93 (s, 1H), 7.67 (d, J=6.8 Hz, 1H), 7.52 (dd, $J_1$=8.6 Hz, $J_2$=1.8 Hz, 1H), 6.19 (s, 2H), 3.79 (s, 3H), 2.76 (s, 3H). ES+MS m/z: 395.2 (M+1).

Synthesis of 6-chloro-2-((2-(1,5-dimethyl-1H-pyrazol-4-yl)-5H-imidazo[4,5-c]pyridin-5-yl)methyl) benzo[d]thiazole CPD-5

Following general procedure 2, 6-chloro-2-((2-(1,5-dimethyl-1H-pyrazol-4-yl)-5H-imidazo[4,5-c]pyridin-5-yl) methyl)benzo[d]thiazole CPD-5 was obtained as off-white solid (175 mg, 27%). $^1$H NMR (400 MHz, DMSO-d6) δ ppm: 8.94 (s, 1H), 8.28 (d, J=2.0 Hz, 1H), 8.19 (d, J=6.8 Hz, 1H), 7.99 (d, J=8.8 Hz, 1H), 7.93 (s, 1H), 7.67 (d, J=6.8 Hz, 1H), 7.55 (dd, $J_1$=8.8 Hz, $J_2$=2.0 Hz, 1H), 6.18 (s, 2H), 3.79 (s, 3H), 2.76 (s, 3H). ES+MS m/z: 395.3 (M+1).

Synthesis of 2-((2-(1,5-dimethyl-1H-pyrazol-4-v0-5H-imidazo[4,5-c]pyridin-5-yl)methyl)naphtho[2,1-d]thiazole CPD-6

Following general procedure 2, 2-((2-(1,5-dimethyl-1H-pyrazol-4-yl)-5H-imidazo[4,5-c]pyridin-5-yl)methyl)naphtho[2,1-d]thiazole CPD-6 was obtained as off-white solid (90 mg, 27%). $^1$H NMR (400 MHz, DMSO-d6) δ ppm: 9.03 (s, 1H), 8.24 (d, J=1.2 Hz, 1H), 8.18-8.00 (m, 4H), 7.95 (s, 1H), 7.75-7.57 (m, 3H), 6.27 (s, 2H), 3.79 (s, 3H), 2.77 (s, 3H). ES+MS m/z: 411.4 (M+1).

Synthesis of 3-(2,5-difluorophenyl)-5-((2-(1,5-dimethyl-1H-pyrazol-4-yl)-5H-imidazo[4,5-c]pyridin-5-yl)methyl)isoxazole CPD-7

Following general procedure 2, 3-(2,5-difluorophenyl)-5-((2-(1,5-dimethyl-1H-pyrazol-4-yl)-5H-imidazo[4,5-c]pyridin-5-yl)methyl)isoxazole CPD-7 was obtained as off-white solid (55 g, 46%). $^1$H NMR (400 MHz, DMSO-d6) δ ppm: 8.92 (s, 1H), 8.18 (d, J=1.2 Hz, 1H), 8.16 (s, 1H), 7.93-7.65 (m, 2H), 7.51-7.41 (m, 2H), 7.09 (d, J=2.8 Hz, 1H), 5.97 (s, 2H), 3.78 (s, 3H), 2.75 (s, 3H). ES+MS m/z: 407.3 (M+1).

Synthesis of 2-((2-(1,5-dimethyl-1H-pyrazol-4-yl-5H-imidazo[4,5-c]pyridin-5-yl)methyl)-5-methylbenzo[d]oxazole CPD-8

Following general procedure 2, 2-((2-(1,5-dimethyl-1H-pyrazol-4-yl)-5H-imidazo[4,5-c]pyridin-5-yl)methyl)-5-methylbenzo[d]oxazole CPD-8 was obtained as off-white solid (40 mg, 12%). $^1$H NMR (400 MHz, DMSO-d6) δ ppm: 8.90 (s, 1H), 8.15 (d, J=6.8 Hz, 1H), 7.94 (s, 1H), 7.66 (d, J=6.8 Hz, 1H), 7.62 (d, J=8.4 Hz, 1H), 7.51 (s, 1H), 7.22 (d, J=8.4 Hz, 1H), 6.08 (s, 2H), 3.79 (s, 3H), 2.77 (s, 3H), 2.39 (s, 3H). ES−MS m/z: 357.2 (M−1).

Synthesis of 1-((2-(1,5-dimethyl-1H-pyrazol-4-yl-5H-imidazo[4,5-c]pyridin-5-ylmethyl)-1H-benzo[d][1,2,3]triazole CPD-9

Following general procedure 2, 1-((2-(1,5-dimethyl-1H-pyrazol-4-yl)-5H-imidazo[4,5-c]pyridin-5-yl)methyl)-1H-benzo[d][1,2,3]triazole CPD-9 was obtained as off-white solid (165 mg, 51%). $^1$H NMR (400 MHz, DMSO-d6) δ ppm: 9.10 (s, 1H), 8.32-8.28 (m, 2H), 8.12 (d, J=8.4 Hz, 1H), 7.90 (s, 1H), 7.72 (m, 1H), 7.68 (d, J=0.8 Hz, 1H), 7.50-7.46 (m, 1H), 7.41 (s, 2H), 3.77 (s, 3H), 2.73 (s, 3H). ES+MS m/z: 345.4 (M+1).

Synthesis of 2-((2-(1,3-dimethyl-1H-pyrazol-4-yl)-5H-imidazo[4,5-c]pyridin-5-yl)methyl)-6-methylbenzo[d]thiazole CPD-10

Following general procedure 2, 2-((2-(1,3-dimethyl-1H-pyrazol-4-yl)-5H-imidazo[4,5-c]pyridin-5-yl)methyl)-6-methylbenzo[d]thiazole CPD-10 was obtained as pale yellow solid (5.1 g, 43%). $^1$H NMR (400 MHz, DMSO-d6) δ ppm: 8.94 (s, 1H), 8.20 (s, 1H), 8.20-8.13 (m, 1H), 7.93-7.82 (m, 2H), 7.64 (d, J=6.8 Hz, 1H), 7.35-7.30 (m, 1H), 6.14 (s, 2H), 3.82 (s, 3H), 2.57 (s, 3H), 2.42 (s, 3H). ES+MS m/z: 375.3 (M+1).

Synthesis of 2-((2-(1,3-dimethyl-1H-pyrazol-4-yl)-5H-imidazo[4,5-c]pyridin-5-yl)methyl)-5-methylbenzo[d]thiazole CPD-11

Following general procedure 2, 2-((2-(1,3-dimethyl-1H-pyrazol-4-yl)-5H-imidazo[4,5-c]pyridin-5-yl)methyl)-5-methylbenzo[d]thiazole CPD-11 was obtained as pale yellow solid (90 mg, 64%). $^1$H NMR (400 MHz, DMSO-d6) 5 ppm: 8.94 (s, 1H), 8.19 (s, 1H), 8.18 (d, J=6.8 Hz, 1H), 7.97 (d, J=8.4 Hz, 1H), 7.80 (s, 1H), 7.64 (d, J=6.8 Hz, 1H), 7.29 (d, J=8.0 Hz, 1H), 6.15 (s, 2H), 3.82 (s, 3H), 2.57 (s, 3H), 2.42 (s, 3H). ES+MS m/z: 375.3 (M+1).

Synthesis of 2-((2-(1,3-dimethyl-1H-pyrazol-4-yl)-5H-imidazo[4,5-c]pyridin-5-yl)methyl)-5-methylbenzo[d]oxazole CPD-12

Following general procedure 2, 2-((2-(1,3-dimethyl-1H-pyrazol-4-yl)-5H-imidazo[4,5-c]pyridin-5-yl)methyl)-5-methylbenzo[d]oxazole CPD-12 was obtained as pale yellow solid (80 mg, 24%). $^1$H NMR (400 MHz, DMSO-d6) δ ppm: 8.90 (s, 1H), 8.21 (s, 11H), 8.14 (d, J=6.8 Hz, 1H), 7.70-7.60 (m, 2H), 7.51 (s, 1H), 7.23 (d, J=8.0 Hz, 1H), 6.07 (s, 2H), 3.82 (s, 3H), 2.57 (s, 3H), 2.39 (s, 3H). ES+MS m/z: 359.3 (M+1).

Synthesis of 3-(2,5-difluorophenyl)-5-((2-(1,3,5-trimethyl-1H-pyrazol-4-yl)-5H-imidazo[4,5-c]pyridin-5-yl)methyl)isoxazole CPD-13

Following general procedure 2, 3-(2,5-difluorophenyl)-5-((2-(1,3,5-trimethyl-1H-pyrazol-4-yl)-5H-imidazo[4,5-c] pyridin-5-yl)methyl)isoxazole CPD-13 was obtained as white solid (17 mg, 7%). $^1$H NMR (400 MHz, DMSO-d6) δ ppm: 8.96 (s, 1H), 8.16 (s, 1H), 7.76-7.63 (m, 2H), 7.54-7.40 (m, 2H), 7.10 (s, 1H), 5.97 (s, 2H), 3.71 (s, 3H), 2.72 (s, 3H), 2.52 (s, 3H). ES+MS m/z: 421.4 (M+1).

Synthesis of 2-((2-(2-methoxypyridin-3-yl)-5H-imidazo[4,5-c]pyridin-5-yl)methyl)-6-methylbenzo [d]thiazole CPD-14

Following general procedure 2, 2-((2-(2-methoxypyridin-3-yl)-5H-imidazo[4,5-c]pyridin-5-yl)methyl)-6-methylbenzo[d]thiazole CPD-14 was obtained as off-white solid (70 mg, 18%). $^1$H NMR (400 MHz, DMSO-d6) δ ppm: 9.19 (s, 1H), 8.43 (d, J=6.0 Hz, 1H), 8.28-8.25 (m, 2H), 7.90 (s, 1H), 7.87-7.81 (m, 2H), 7.34 (d, J=8.0 Hz, 1H), 7.13-7.09 (m, 1H), 6.22 (s, 2H), 3.94 (s, 3H), 2.42 (s, 3H). ES+MS m/z: 388.6 (M+1).

Synthesis of 2-((2-(2-methoxypyridin-3-yl)-5H-imidazo[4,5-c]pyridin-5-yl)methyl)-5-methylbenzo [d]thiazole CPD-15

Following general procedure 2, 2-((2-(2-methoxypyridin-3-yl)-5H-imidazo[4,5-c]pyridin-5-yl)methyl)-5-methylbenzo[d]thiazole CPD-15 was obtained as light brown solid (20 mg, 16%). $^1$H NMR (400 MHz, DMSO-d8) δ ppm: 9.18 (s, 1H), 8.42 (dd, $J_1$=7.6 Hz, $J_2$=2.0 Hz, 1H), 8.28-8.24 (m, 2H), 7.98 (d, J=8.0 Hz, 1H), 7.85-7.79 (m, 2H), 7.30 (d, J=8.0 Hz, 1H), 7.12 (d, J=7.4 Hz, 1H), 6.22 (s, 2H), 3.94 (s, 3H), 2.42 (s, 3H). ES+MS m/z: 388.6 (M+1).

Synthesis of 2-((2-(2-methoxypyridin-3-yl)-5H-imidazo[4,5-c]pyridin-5-yl)methyl)-5-methylbenzo[d]oxazole CPD-16

Following general procedure 2, 2-((2-(2-methoxypyridin-3-yl)-5H-imidazo[4,5-c]pyridin-5-yl)methyl)-5-methyl-benzo[d]oxazole CPD-16 was obtained as white solid (70 mg, 17%).

$^1$H NMR (400 MHz, DMSO-d6) δ ppm: 9.14 (s, 1H), 8.42 (dd, $J_1$=7.2 Hz, $J_2$=1.6 Hz, 1H), 8.26-8.23 (m, 2H), 7.82 (d, J=6.8 Hz, 1H), 7.64 (d, J=8.4 Hz, 1H), 7.51 (s, 1H), 7.24 (d, J=8.0 Hz, 1H), 7.12 (dd, $J_1$=7.2 Hz, $J_2$=4.8 Hz, 1H), 6.14 (s, 2H), 3.94 (s, 3H), 2.39 (s, 3H).

ES+MS m/z: 372.4 (M+1).

Synthesis of 3-(2,5-difluorophenyl)-5-((2-(2-methoxypyridin-3-yl)-5H-imidazo[4,5-c]pyridin-5-yl)methyl)isoxazole CPD-17

Following general procedure 2, 3-(2,5-difluorophenyl)-5-((2-(2-methoxypyridin-3-yl)-5H-imidazo[4,5-c]pyridin-5-yl)methyl)isoxazole CPD-17 was obtained as off-white solid (1.64 g, 45%). $^1$H NMR (400 MHz, DMSO-d8) δ ppm: 9.16 (s, 1H), 8.42 (dd, $J_1$=7.2 Hz, $J_2$=1.6 Hz, 1H), 8.26-8.23 (m, 2H), 7.82 (d, J=6.8 Hz, 1H), 7.73-7.60 (m, 1H), 7.52-7.42 (m, 2H), 7.12-7.09 (m, 2H), 6.04 (s, 2H), 3.93 (a, 3H). ES+MS m/z: 420.7 (M+1).

Synthesis of 2-((2-(2-methoxyphenyl)-5H-imidazo[4,5-c]pyridin-5-yl)methyl)-6-methylbenzo[d]thiazole CPD-18

Following general procedure 2, 2-((2-(2-methoxyphenyl)-5H-imidazo[4,5-c]pyridin-5-yl)methyl)-6-methylbenzo[d]thiazole CPD-18 was obtained as light pink solid (240 mg, 32%). $^1$H NMR (400 MHz, DMSO-d8) 5 ppm: 9.14 (s, 1H), 8.26 (d, J=6.4 Hz, 1H), 7.96-7.85 (m, 3H), 7.79 (d, J=6.8 Hz, 1H), 7.45-7.35 (m, 1H), 7.33 (d, J=8.0 Hz, 1H), 7.13 (d, J=8.0 Hz, 1H), 7.03 (t, J=7.2 Hz, 1H), 6.21 (s, 2H), 3.82 (s, 3H), 2.43 (s, 3H). ES+MS m/z: 387.3 (M+1).

Synthesis of 3-(2,5-difluorophenyl)-5-((2-(2-methoxyphenyl)-5H-imidazo[4,5-c]pyridin-5-yl)methyl)isoxazole CPD-19

Following general procedure 2, 3-(2,5-difluorophenyl)-5-((2-(2-methoxyphenyl)-5H-imidazo[4,5-c]pyridin-5-yl)methyl)isoxazole CPD-19 was obtained as white solid (150 mg, 32%). $^1$H NMR (400 MHz, DMSO-d6) δ ppm: 9.10 (s, 1H), 8.23 (dd, $J_1$=6.8 Hz, $J_2$=1.6 Hz, 1H), 7.98-7.90 (m, 1H), 7.78 (d, J=6.8 Hz, 1H), 7.73-7.69 (m, 1H), 7.50-7.37 (m, 3H), 7.13-7.10 (m, 2H), 7.04 (t, J=7.4 Hz, 1H), 6.03 (s, 2H), 3.80 (s, 3H). ES+MS m/z: 419.6 (M+1).

Synthesis of 1-((2-(2-methoxyphenyl)-5H-imidazo[4,5-c]pyridin-5-yl)methyl)-1H-benzo[d][1,2,3]triazole CPD-20

Following general procedure 2, 1-((2-(2-methoxyphenyl)-5H-imidazo[4,5-c]pyridin-5-yl)methyl)-1H-benzo[d][1,2,3]triazole CPD-20 was obtained as light pink solid (95 mg, 15%). $^1$H NMR (400 MHz, DMSO-d6) δ ppm: 9.31 (s, 1H), 8.38 (d, J=6.8 Hz, 1H), 8.32 (d, J=8.4 Hz, 1H), 8.13 (d, J=8.4 Hz, 1H), 7.93 (d, J=7.2 Hz, 1H), 7.80-7.65 (m, 2H), 7.55-7.42 (m, 3H), 7.40 (t, J=7.0 Hz, 1H), 7.12 (d, J=8.4 Hz, 1H), 7.01 (t, J=7.4 Hz, 1H), 3.79 (s, 3H).

ES+MS m/z: 357.4 (M+1).

Synthesis of 2-((2-(2-(difluoromethoxy)phenyl)-5H-imidazo[4,5-c]pyridin-5-yl)methyl)-6-methylbenzo[d]thiazole CPD-21

Following general procedure 2, 2-((2-(2-(difluoromethoxy)phenyl)-5H-imidazo[4,5-c]pyridin-5-yl)methyl)-6-methylbenzo[d]thiazole CPD-21 was obtained as off-white solid (0.120 g, 21%). $^1$H NMR (400 MHz, DMSO-d6) δ ppm: 9.24 (s, 1H), 8.35-8.23 (m, 2H), 7.91 (s, 1H), 7.87-7.83 (m, 2H), 7.52-7.48 (m, 1H), 7.43-7.37 (m, 1H), 7.35-7.27 (m, 2H), 7.32 (t, J=76 Hz, 1H), 6.23 (s, 2H), 2.43 (s, 3H). ES+MS m/z: 423.4 (M+1).

Synthesis of 2-((2-(2-fluorophenyl-5H-imidazo[4,5-c]pyridin-5-yl)methyl)-6-methylbenzo[d]thiazole CPD-22

Following general procedure 2, 2-((2-(2-fluorophenyl)-5H-imidazo[4,5-c]pyridin-5-yl)methyl)-6-methylbenzo[d]thiazole CPD-22 was obtained as off-white solid (30 mg, 11%). $^1$H NMR (400 MHz, DMSO-d6) δ ppm: 9.21 (s, 1H), 8.38-8.25 (m, 2H), 7.90 (s, 1H), 7.88-7.80 (m, 2H), 7.52-7.45 (m, 1H), 7.38-7.25 (m, 3H), 6.22 (s, 2H), 2.43 (s, 3H). ES+MS m/z: 375.6 (M+1).

Synthesis of 2-((2-(2-fluorophenyl)-5H-imidazo[4,5-c]pyridin-5-yl)methyl)-5-methylbenzo[d]thiazole CPD-23

Following general procedure 2, 2-((2-(2-fluorophenyl)-5H-imidazo[4,5-c]pyridin-5-yl)methyl)-5-methylbenzo[d]thiazole CPD-23 was obtained as off-white solid (70 mg, 26%). $^1$H NMR (400 MHz, DMSO-d8) 5 ppm: 9.22 (s, 1H), 8.37-8.26 (m, 2H), 7.98 (d, J=8.4 Hz, 1H), 7.85 (d, J=6.8 Hz, 1H), 7.80 (s, 1H), 7.53-7.42 (m, 1H), 7.36-7.25 (m, 3H), 6.23 (s, 2H), 2.42 (s, 3H). ES+MS m/z: 375.5 (M+1).

Synthesis of 2-((2-(2-fluorophenyl)-5H-imidazo[4,5-c]pyridin-5-yl)methyl)benzo[d]thiazole CPD-24

Following general procedure 2, 2-((2-(2-fluorophenyl)-5H-imidazo[4,5-c]pyridin-5-yl)methyl)benzo[d]thiazole CPD-24 was obtained as off-white solid (90 mg, 17%). $^1$H NMR (400 MHz, DMSO-d6) δ ppm: 9.23 (s, 1H), 8.38-8.27 (m, 2H), 8.12 (d, J=8.0 Hz, 1H), 7.98 (d, J=8.0 Hz, 1H), 7.85 (d, J=6.8 Hz, 1H), 7.56-7.42 (m, 3H), 7.33-7.27 (m, 2H), 6.26 (s, 2H). ES+MS m/z: 361.3 (M+1).

Synthesis of 6-chloro-2-((2-(2-fluorophenyl)-5H-imidazo[4,5-c]pyridin-5-yl)methyl)benzo[d]thiazole CPD-25

Following general procedure 2, 6-chloro-2-((2-(2-fluorophenyl)-5H-imidazo[4,5-c]pyridin-5-yl)methyl)benzo[d]thiazole CPD-25 was obtained as off-white solid (44 mg, 6%). $^1$H NMR (400 MHz, DMSO-d5) δ ppm: 9.22 (s, 1H), 8.38-8.25 (m, 3H), 7.98 (d, J=8.8 Hz, 1H), 7.85 (d, J=6.8 Hz, 1H), 7.55 (d, J=8.4 Hz, 1H), 7.51-7.43 (m, 1H), 7.38-7.25 (m, 2H), 6.25 (s, 2H). ES+MS m/z: 395.2 (M+1).

Synthesis of 5-chloro-2-((2-(2-fluorophenyl)-5H-imidazo[4,5-c]pyridin-5-yl)methyl)benzo[d]thiazole CPD-26

Following general procedure 2, 5-chloro-2-((2-(2-fluorophenyl)-5H-imidazo[4,5-c]pyridin-5-yl)methyl)benzo[d]thiazole CPD-26 was obtained as off-white solid (230 mg, 31%). $^1$H NMR (400 MHz, DMSO-d6) δ ppm: 9.23 (s, 1H), 8.37-8.25 (m, 2H), 8.17 (d, J=8.8 Hz, 1H), 8.10 (s, 1H), 7.86 (d, J=6.8 Hz, 1H), 7.56-7.42 (m, 2H), 7.37-7.26 (m, 2H), 6.27 (s, 2H). ES+MS m/z: 395.3 (M+1).

Synthesis of (2-((2-(2-fluorophenyl)-5H-imidazo[4,5-c]pyridin-5-yl)methyl)benzo[d]thiazol-6-yl)methanol CPD-27

Following general procedure 2, 6-bromo-2-((2-(2-fluorophenyl)-5H-imidazo[4,5-c]pyridin-5-yl)methyl)benzo[d]thiazole was obtained (0.600 g, 52%).

Step 3

6-bromo-2-((2-(2-fluorophenyl)-5H-imidazo[4,5-c]pyridin-5-yl)methyl)benzo[d]thiazole (0.600 g, 1.0 eq.) was dissolved in methanol (30 mL, 50 V) and potassium acetate (0.266 g, 2 eq.), Xantphos (0.157 g, 0.2 eq.) and $Pd_2(dba)_3$ (0.125 g, 0.1 eq.) were added at room temperature. The resulting reaction mixture was degassed for 20 min and stirred under 2 kg/cm$^3$ carbon monoxide pressure for 12 h at 120° C. The reaction mixture was then allowed to cool to room temperature and filtered through celite pad. The celite pad was washed with methanol and the filtrate was concentrated under reduced pressure. The crude product was purified by column chromatography to get the methyl 2-((2-(2-fluorophenyl)-5H-imidazo[4,5-c]pyridin-5-yl)methyl)benzo[d]thiazole-6-carboxylate (380 mg, 66%).

Step 4

Methyl 2-((2-(2-fluorophenyl)-5H-imidazo[4,5-c]pyridin-5-yl)methyl)benzo[d]thiazole-6-carboxylate (0.380 g, 1.0 eq.) was dissolved in tetrahydrofuran (38 mL, 100V) cooled to −20° C. and lithium aluminium hydride (0.068 g, 2.0 eq.) was added. The resulting reaction mass was stirred for 3 h at −20° C. The reaction was quenched with ammonium chloride solution and extracted with dichloromethane (10% methanol). The separated organic layer was filtered through celite pad and the filtrate was concentrated under reduced pressure. The crude was purified by column chromatography to obtain (2-((2-(2-fluorophenyl)-5H-imidazo[4,5-c]pyridin-5-yl)methyl)benzo[d]thiazol-6-yl)methanol CPD-27 as off-white solid (100 mg, 28%). $^1$H NMR (400 MHz, DMSO-d6) δ ppm: 9.23 (s, 1H), 8.38-8.25 (m, 2H), 8.04 (s, 1H), 7.92 (d, J=8.4 Hz, 1H), 7.85 (d, J=6.8 Hz, 1H), 7.53-7.38 (m, 2H), 7.35-7.22 (m, 2H), 6.24 (s, 2H), 5.38 (brs, 1H), 4.61 (s, 2H). ES+MS m/z: 391.6 (M+1).

Synthesis of 2-((2-(2-fluorophenyl)-5H-imidazo[4,5-c]pyridin-5-yl)methyl)-5-phenylthiazole CPD-28

Following general procedure 2, 2-((2-(2-fluorophenyl)-5H-imidazo[4,5-c]pyridin-5-yl)methyl)-5-phenylthiazole CPD-28 was obtained as off-white solid (190 mg, 41%). $^1$H NMR (400 MHz, DMSO-d8) δ ppm: 9.21 (s, 1H), 8.34-8.25 (m, 2H), 8.22 (s, 1H), 7.84 (d, J=6.8 Hz, 1H), 7.65 (d, J=7.2 Hz, 2H), 7.54-7.38 (m, 3H), 7.37-7.26 (m, 3H), 6.11 (s, 2H). ES+MS m/z: 387.3 (M+1).

Synthesis of 2-((2-(2-fluorophenyl)-5H-imidazo[4,5-c]pyridin-5-yl)methyl)-4-methyl-5-phenylthiazole CPD-29

Following general procedure 2, 2-((2-(2-fluorophenyl)-5H-imidazo[4,5-c]pyridin-5-yl)methyl)-4-methyl-5-phenylthiazole CPD-29 was obtained as off-white solid (100 mg, 28%). $^1$H NMR (400 MHz, DMSO-d6) δ ppm: 9.19 (s, 1H), 8.38-8.23 (m, 2H), 7.84 (d, J=6.8 Hz, 1H), 7.52-7.42 (m, 5H), 7.42-7.33 (m, 1H), 7.33-7.24 (m, 2H), 6.06 (s, 2H), 2.39 (s, 3H). ES+MS m/z: 401.3 (M+1).

Synthesis of 5-((5-chlorothiophen-2-yl)methyl)-2-(2-fluorophenyl-5H-imidazo[4,5-c]pyridine CPD-30

Following general procedure 2, 5-((5-chlorothiophen-2-yl)methyl)-2-(2-fluorophenyl)-5H-imidazo[4,5-c]pyridine CPD-30 was obtained as off-white solid (140 mg, 35%). $^1$H NMR (400 MHz, DMSO-d6) δ ppm: 9.17 (s, 1H), 8.30 (t, J=7.6 Hz, 1H), 8.24 (d, J=6.8 Hz, 1H), 7.80 (d, J=6.8 Hz, 1H), 7.53-7.42 (m, 1H), 7.35-7.27 (m, 3H), 7.09 (d, J=4.0 Hz, 1N), 5.83 (s, 2H). ES+MS m/z: 344.1 (M+1).

Synthesis of 2-((2-(2-fluorophenyl-5H-imidazo[4,5-c]pyridin-5-yl)methyl)-5-methylbenzo[d]oxazole CPD-31

Following general procedure 2, 2-((2-(2-fluorophenyl)-5H-imidazo[4,5-c]pyridin-5-yl)methyl)-5-methylbenzo[d]oxazole CPD-31 was obtained as white solid (115 mg, 27%). $^1$H NMR (400 MHz, DMSO-d8) δ ppm: 9.18 (s, 1H), 8.33 (t, J=7.8 Hz, 1H), 8.26 (d, J=6.8 Hz, 1H), 7.85 (d, J=6.8 Hz, 1H), 7.63 (d, J=8.4 Hz, 1H), 7.58-7.44 (m, 2H), 7.31 (t, J=8.5 Hz, 2H), 7.23 (d, J=8.4 Hz, 1H), 6.15 (s, 2H), 2.39 (s, 3H). ES+MS m/z: 359.5 (M+1).

Synthesis of 2-((2-(2-fluorophenyl)-5H-imidazo[4,5-c]pyridin-5-yl)methyl)-6-methylbenzo[d]oxazole CPD-32

Following general procedure 2, 2-((2-(2-fluorophenyl)-5H-imidazo[4,5-c]pyridin-5-yl)methyl)-6-methylbenzo[d]oxazole CPD-32 was obtained as white solid (125 mg, 29%). $^1$H NMR (400 MHz, DMSO-d8) δ ppm: 9.17 (s, 1H), 8.33 (t, J=7.8 Hz, 1H), 8.26 (d, J=6.8 Hz, 1N), 7.85 (d, J=6.8 Hz, 1H), 7.64-7.53 (m, 2H), 7.52-7.42 (m, 1H), 7.31 (t, J=8.0 Hz, 2H), 7.20 (d, J=8.4 Hz, 1H), 6.14 (s, 2H), 2.43 (s, 3H). ES+MS m/z: 359.6 (M+1).

Synthesis of 2-((2-(2-fluorophenyl)-5H-imidazo[4,5-c]pyridin-5-yl)methyl)-5-methoxybenzo[d]oxazole CPD-33

Following general procedure 2, 2-((2-(2-fluorophenyl)-5H-imidazo[4,5-c]pyridin-5-yl)methyl)-5-methoxybenzo[d]oxazole CPD-33 was obtained as off-white solid (30 mg, 24%). $^1$H NMR (400 MHz, DMSO-d6) δ ppm: 9.17 (s, 1N), 8.33 (t, J=7.8 Hz, 1H), 8.26 (d, J=6.0 Hz, 1H), 7.85 (d, J=6.8 Hz, 1H), 7.66 (d, J=9.2 Hz, 1H), 7.54-7.43 (m, 1H), 7.37-7.26 (m, 3H), 6.99 (d, J=8.8 Hz, 1N), 6.14 (s, 2H), 3.76 (s, 3H). ES+MS m/z: 375.2 (M+1).

Synthesis of 3-(2,4-difluorophenyl)-5-((2-(2-fluorophenyl)-5H-imidazo[4,5-c]pyridin-5-yl)methyl)isoxazole CPD-34

Following general procedure 2, 3-(2,4-difluorophenyl)-5-((2-(2-fluorophenyl)-5H-imidazo[4,5-c]pyridin-5-yl)methyl)isoxazole CPD-34 was obtained as off-white solid (3.2 g, 33%). $^1$H NMR (400 MHz, DMSO-d6) 5 ppm: 9.20 (s, 1H), 8.32 (t, J=7.7 Hz, 1H), 8.27 (d, J=7.0 Hz, 1H), 8.00-7.90 (m, 1H), 7.84 (d, J=6.8 Hz, 1H), 7.55-7.43 (m, 2H), 7.36-7.22 (m, 3H), 7.08 (s, 1H), 6.04 (s, 2H). ES+MS m/z: 407.5 (M+1).

Synthesis of 3-(2,5-difluorophenyl)-5-((2-(2-fluorophenyl)-5H-imidazo[4,5-c]pyridin-5-yl)methyl)isoxazole CPD-35

Following general procedure 2, 3-(2,5-difluorophenyl)-5-((2-(2-fluorophenyl)-5H-imidazo[4,5-c]pyridin-5-yl)methyl)isoxazole 35 was obtained as off-white solid (110 mg, 11%). $^1$H NMR (400 MHz, DMSO-d6) 5 ppm: 9.20 (s, 1H), 8.38-8.23 (m, 2H), 7.85 (d, J=6.8 Hz, 1H), 7.80-7.67 (m, 1H), 7.56-7.40 (m, 3H), 7.35-7.26 (m, 2H), 7.12 (s, 1H), 6.05 (s, 2H). ES+MS m/z: 407.1 (M+1).

Synthesis of 2-(2-fluorophenyl-5-((6-methyl-1H-benzo[d]imidazol-2-yl)methyl)-5H-imidazo[4,5-c]pyridine CPD-36

Following general procedure 2, 2-(2-fluorophenyl)-5-((6-methyl-1H-benzo[d]imidazol-2-yl)methyl)-5H-imidazo[4,5-c]pyridine CPD-36 was obtained as white solid (50 mg, 25%).

$^1$H NMR (400 MHz, DMSO-d5) δ ppm: 12.58 (s, 1H), 9.12 (s, 1H), 8.32 (t, J=8.0 Hz, 1H), 8.17 (d, J=8.0 Hz, 1H), 7.80 (d, J=8.0 Hz, 1H), 7.53-7.23 (m, 5H), 7.01 (s, 1H), 5.95 (s, 2H), 2.38 (s, 3H). ES+MS m/z: 358.1 (M+1).

Synthesis of 5-((6-fluoro-1H-benzo[d]imidazol-2-yl)methyl)-2-(2-fluorphenyl)-5H-imidazo[4,5-c]pyridine CPD-37

Following general procedure 2, 5-((6-fluoro-1H-benzo[d]imidazol-2-yl)methyl)-2-(2-fluorophenyl)-5H-imidazo[4,5-c]pyridine CPD-37 was obtained as white solid (65 mg, 10%). $^1$H NMR (400 MHz, DMSO-d8) δ ppm: 12.83 (s, 1H), 9.13 (s, 1H), 8.38-8.26 (m, 1H), 8.23-8.15 (m, 1H), 7.87-7.78 (m, 1H), 7.68-7.23 (m, 5H), 7.18-6.97 (m, 1H), 5.98 (s, 2H). ES+MS m/z: 362.5 (M+1).

Synthesis of 1-((2-(2-fluorophenyl-5H-imidazo[4,5-c]pyridin-5-yl)methyl)-1H-benzo[d][1,2,3]triazole CPD-38

Following general procedure 2, 1-((2-(2-fluorophenyl)-5H-imidazo[4,5-c]pyridin-5-yl)methyl)-1H-benzo[d][1,2,3]triazole CPD-38 was obtained as white solid (104 mg, 26%).

$^1$H NMR (400 MHz, DMSO-d6) δ ppm: 9.41 (s, 1H), 8.41 (d, J=7.8 Hz, 1H), 8.35-8.24 (m, 2H), 8.13 (d, J=8.4 Hz, 1H), 7.82 (d, J=6.8 Hz, 1H), 7.71 (t, J=7.6 Hz, 1H), 7.54-7.42 (m, 4H), 7.35-7.23 (m, 2H). ES+MS m/z: 345.1 (M+1).

Synthesis of 3-(2,5-difluorophenyl)-5-((2-(3-fluorophenyl)-5H-imidazo[4,5-c]pyridin-5-yl)methyl)isoxazole CPD-39

Following general procedure 2, 3-(2,5-difluorophenyl)-5-((2-(3-fluorophenyl)-5H-imidazo[4,5-c]pyridin-5-yl)methyl)isoxazole CPD-39 was obtained as light yellow solid (0.13 g, 17%). $^1$H NMR (400 MHz, DMSO-d6) δ ppm: 9.19 (s, 1H), 8.27 (d, J=7.6 Hz, 1H), 8.21 (d, J=7.6 Hz, 1H), 8.08 (d, J=9.2 Hz, 1H), 7.83 (d, J=6.8 Hz, 1H), 7.78-7.67 (m, 1H), 7.58-7.41 (m, 3H), 7.32-7.23 (m, 1H), 7.12 (s, 1H), 6.04 (s, 2H). ES+MS m/z: 407.5 (M+1).

Synthesis of 1-((2-(2-fluoro-5-(trifluoromethoxy)phenyl)-5H-imidazo[4,5-c]pyridin-5-yl)methyl)-1H-benzo[d][1,2,3]triazole CPD-40

Following general procedure 2, 1-((2-(2-fluoro-5-(trifluoromethoxy)phenyl)-5H-imidazo[4,5-c]pyridin-5-yl)methyl)-1H-benzo[d][1,2,3]triazole CPD-40 (1.0 g, 63%) was obtained as off-white solid. $^1$H NMR (400 MHz, DMSO-d6) δ ppm: 9.48 (s, 1H), 8.43 (d, J=7.2 Hz, 1H), 8.31 (d, J=8.4 Hz, 1H), 8.25-8.18 (m, 1H), 8.13 (d, J=8.0 Hz, 1H), 7.87 (d, J=6.8 Hz, 1H), 7.71 (t, J=7.2 Hz, 1H), 7.55-7.40 (m, 5H). ES+MS m/z 429.1 (M+1).

Synthesis of 2-(4-fluoro-3-(5-((6-methylbenzo[d]thiazol-2-yl)methyl)-5H-imidazo[4,5-c]pyridin-2-yl)phenoxy)ethan-1-ol CPD-41

Following general procedure 2, 2-((2-(5-(2-(benzyloxy)ethoxy)-2-fluorophenyl)-5H-imidazo[4,5-c]pyridin-5-yl)methyl)-6-methylbenzo[d]thiazole was prepared. The crude product was dissolved in dichloromethane (20 V) and treated with boron trichloride (3.0 eq. 1.0 M in dichloromethane) dropwise at 0° C. The resulting suspension was stirred at room temperature for 30 min. The reaction was quenched with methanol at 0° C. The volatiles were evaporated under reduced pressure and the obtained crude was purified by column chromatography. 2-(4-fluoro-3-(5-((6-methylbenzo[d]thiazol-2-yl)methyl)-5H-imidazo[4,5-c]pyridin-2-yl)phenoxy)ethan-1-ol CPD-41 was obtained as off-white solid (50 mg, 21% over 2 steps). $^1$H NMR (400 MHz, DMSO-d6) δ ppm: 9.22 (s, 1H), 8.29 (d, J=6.8 Hz, 1H), 7.98-7.80 (m, 4H), 7.33 (d, J=8.0 Hz, 1H), 7.23 (t, J=9.6 Hz, 1H), 7.10-6.98 (m, 1H), 6.22 (s, 2H), 4.90 (t, J=5.4 Hz, 1H), 4.15-4.00 (m, 2H), 3.84-3.65 (m, 2H), 2.43 (s, 3H). ES+MS m/z: 435.7 (M+1).

Synthesis of 2-(3-(5-((3-(2,5-difluorophenyl)isoxazol-5-yl)methyl)-5H-imidazo[4,5-c]pyridin-2-yl)-4-fluorophenoxy)ethan-1-ol CPD-42

Following general procedure 2, 5-((2-(5-(2-(benzyloxy)ethoxy)-2-fluorophenyl)-5H-imidazo[4,5-c]pyridin-5-yl)meth)-3-(2,5-difluorophenyl)isoxazole was prepared. The crude product was dissolved in dichloromethane (20 V) and treated with boron trichloride (3.0 eq. 1.0 M in DCM) dropwise at 0° C. The resulting suspension was stirred at room temperature for 30 min. The reaction was quenched with methanol at 0° C. The volatiles were evaporated under reduced pressure and the obtained crude was purified by column chromatography. 2-(3-(5-((3-(2,5-difluorophenyl)isoxazol-5-yl)methyl)-5H-imidazo[4,5-c]pyridin-2-yl)-4-fluorophenoxy)ethan-1-ol CPD-42 was obtained as off-white solid (35 mg, 9% over 2 steps). $^1$H NMR (400 MHz, DMSO-d6) 5 ppm: 9.20 (s, 1H), 8.28 (d, J=6.4 Hz, 1H), 7.95-7.80 (m, 2H), 7.78-7.66 (m, 1H), 7.57-7.40 (m, 2H), 7.23 (t, J=9.6 Hz, 1H), 7.12 (s, 1H), 7.08-8.98 (m, 1H), 6.05 (s, 2H), 4.91 (t, J=5.4 Hz, 1H), 4.10-4.02 (m, 2H), 3.83-3.68 (m, 2H). ES+MS m/z: 467.6 (M+1).

Synthesis of 4-(5-((3-(2,5-difluorophenyl)isoxazol-5-yl)methyl)-5H-imidazo[4,5-c]pyridin-2-yl)benzonitrile CPD-43

Following general procedure 2, 4-(5-((3-(2,5-difluorophenyl)isoxazol-5-yl)methyl)-5H-imidazo[4,5-c]pyridin-2-yl)benzonitrile CPD-43 was obtained as off-white solid (180 mg, 45%). $^{1}$H NMR (400 MHz, DMSO-d6) δ ppm: 9.26 (s, 1H), 8.52 (d, J=8.4 Hz, 2H), 8.30 (d, J=6.4 Hz, 1H), 7.95 (d, J=8.4 Hz, 2H), 7.88 (d, J=6.8 Hz, 1H), 7.78-7.66 (m, 1H), 7.58-7.42 (m, 2H), 7.12 (s, 1H), 6.05 (s, 2H). ES+MS m/z: 414.6 (M+1).

Synthesis of 3-(5-((3-(2,5-difluorophenyl)isoxazol-5-yl)methyl)-5H-imidazo[4,5-c]pyridin-2-yl)-N,N-dimethylaniline CPD-44

Following general procedure 2, 3-(5-((3-(2,5-difluorophenyl)isoxazol-5-yl)methyl)-5H-imidazo[4,5-c]pyridin-2-yl)-N,N-dimethylaniline CPD-44 was obtained as off-white solid (120 mg, 25%). $^{1}$H NMR (400 MHz, DMSO-d6) δ ppm: 9.08 (s, 1H), 8.22 (d, J=8.0 Hz, 1H), 7.82-7.75 (m, 2H), 7.73-7.67 (m, 2H), 7.53-7.42 (m, 2H), 7.27 (t, J=8.0 Hz, 1H), 7.10 (s, 1H), 6.82 (d, J=8.0 Hz, 1H), 6.02 (s, 2H), 2.97 (s, 6H). ES+MS m/z: 432.2 (M+1).

Synthesis of (2-(5-((6-methylbenzo[d]thiazol-2-yl)methyl)-5H-imidazo[4,5-c]pyridin-2-yl)phenyl)methanol CPD-45

Following general procedure 2, (2-(5-((6-methylbenzo[d]thiazol-2-yl)methyl)-5H-imidazo[4,5-c]pyridin-2-yl)phenyl)methanol CPD-45 was obtained as white solid (150 mg, 38%). $^{1}$H NMR (400 MHz, DMSO-d6) δ ppm: 9.29 (s, 1H), 8.43-8.32 (m, 2H), 7.96-7.83 (m, 3H), 7.58-7.48 (m, 1H), 7.45-7.38 (m, 2H), 7.37-7.31 (m, 1H), 7.22-7.13 (m, 1H), 6.23 (s, 2H), 4.71 (d, J=6.0 Hz, 2H), 2.43 (s, 3H). ES+MS m/z: 387.7 (M+1).

Synthesis of (2-(5-((3-(2,5-difluorophenyl)isoxazol-5-yl)methyl)-5H-imidazo[4,5-c]pyridin-2-yl)phenyl)methanol CPD-46

Following general procedure 2, (2-(5-((3-(2,5-difluorophenyl)isoxazol-5-yl)methyl)-5H-imidazo[4,5-c]pyridin-2-yl)phenyl)methanol CPD-46 was obtained as off-white solid (100 mg, 27%). $^{1}$H NMR (400 MHz, DMSO-d6) δ ppm: 9.27 (s, 1H), 8.46-8.32 (m, 2H), 7.90 (d, J=6.8 Hz, 1H), 7.78-7.67 (m, 1H), 7.59-7.36 (m, 5H), 7.25-7.10 (m, 2H), 6.06 (s, 2H), 4.70 (s, 2H). ES+MS m/z: 419.7 (M+1).

Synthesis of 3-(2,5-difluorophenyl)-5-((2-(5-methylthiophen-2-yl)-5H-imidazo[4,5-c]pyridin-5-yl)methyl)isoxazole CPD-47

Following general procedure 2, 3-(2,5-difluorophenyl)-5-((2-(5-methylthiophen-2-yl)-5H-imidazo[4,5-c]pyridin-5-yl)methyl)isoxazole CPD-47 was obtained as off-white solid (30 mg, 11%). $^{1}$H NMR (400 MHz, $CDCl_3$) δ ppm: 8.51 (s, 1H), 7.89 (d, J=3.6 Hz, 1H), 7.76 (s, 2H), 7.72-7.65 (m, 1H), 7.22-7.12 (m, 2H), 6.88-6.80 (m, 2H), 5.62 (s, 2H), 2.58 (s, 3H).

ES+MS m/z: 409.8 (M+1).

Synthesis of 3-(2,5-difluorophenyl)-5-((2-(5-methylthiophen-3-yl)-5H-imidazo[4,5-c]pyridin-5-yl)methyl)isoxazole CPD-48

Following general procedure 2, 3-(2,5-difluorophenyl)-5-((2-(5-methylthiophen-3-yl)-5H-imidazo[4,5-c]pyridin-5-yl)methyl)isoxazole CPD-48 was obtained as off-white solid (80 mg, 28%). $^{1}$H NMR (400 MHz, MeOH-d4) δ ppm: 9.02 (s, 1H), 8.32 (d, J=6.8 Hz, 1H), 8.06 (s, 1H), 7.83 (d, J=6.8 Hz, 1H), 7.72-7.62 (m, 1H), 7.54 (s, 1H), 7.38-7.24 (m, 2H), 7.09 (s, 1H), 6.03 (s, 2H), 2.56 (s, 3H). ES+MS m/z: 409.8 (M+1).

Synthesis of 3-(2,5-difluorophenyl)-5-((2-(4,5-dimethylthiophen-3-yl)-5H-imidazo[4,5-c]pyridin-5-yl)methyl)isoxazole CPD-49

Following general procedure 2, 3-(2,5-difluorophenyl)-5-((2-(4,5-dimethylthiophen-3-yl)-5H-imidazo[4,5-c]pyridin-5-yl)methyl)isoxazole CPD-49 was obtained as off-white solid (35 mg, 15%). $^{1}$H NMR (400 MHz, DMSO-d8) δ ppm: 9.06 (s, 1H), 8.21 (d, J=6.4 Hz, 1H), 7.98 (s, 1H), 7.80-7.66 (m, 2H), 7.58-7.40 (m, 2H), 7.11 (s, 1H), 5.99 (s, 2H), 2.57 (s, 3H), 2.38 (s, 3H). ES+MS m/z: 423.6 (M+1).

Example 18. In Vitro Biological Evaluation of the Compounds

Suspensions of MDBK cells (Madin-Darby bovine kidney) were treated with serial dilutions of the compounds of the invention in a 96-well assay. Bovine viral diarrhea (BVD) virus was added at an approximately 100 $TCID_{50}$ (50% tissue culture infective dose). Following four days of incubation, cythopathic effects (CPE) were read visually using a microscope. $EC_{50}$ (50% effective concentration) values were calculated as the compound concentration that caused 50% inhibition of CPE using linear interpolation. Parallel conditions of cells treated with the same drug dilution were assayed for cytotoxicity (no BVD virus added). $CC_{50}$ (50% cytotoxic concentration) values were calculated as the compound concentration that caused 50% toxic effects to the cells using linear interpolation.

Tables 4 and 5 show the results of the in vitro $EC_{50}$ and $CC_{50}$ values for compounds of the invention, and the selectivity index (SI), which corresponds to the ratio of $CC_{50}$ and $EC_{50}$ values.

TABLE 4

| Compound | $EC_{50}$ (nM) | $CC_{50}$ (μM) | SI |
|---|---|---|---|
| I | 9 ± 8 | 22 | 2444 |
| II | 23 ± 0 | 20 | 870 |
| III | 19 ± 7 | 22 | 1158 |
| IV | 8 ± 5 | 22 | 2750 |
| V | 81 ± 1 | >50 | >614 |
| VI | 16 ± 0 | >50 | >3125 |
| VII | 16 ± 1 | 22 | 1375 |
| VIII | 335 ± 80 | >50 | >149 |
| IX | 1.2 ± 1.5 | 5 | 4167 |
| X | 7 ± 4 | 4 | 571 |
| XI | 8 ± 0 | 4 | 500 |
| XII | 20 ± 7 | 5 | 250 |
| XIII | 9 ± 8 | 18 | 2000 |
| XIV | 17 ± 0 | 4 | 235 |
| XV | 16 ± 1 | 17 | 1063 |
| XVI | 294 ± 70 | 22 | 75 |
| XVII | 12 ± 6 | 19 | 1583 |
| XVIII | 76 ± 19 | 12 | 158 |
| XIX | 97 ± 15 | >50 | >515 |
| XX | 82 ± 0 | 39 | 476 |
| XXI | 387 ± 22 | >50 | >129 |
| XXII | 7 ± 5 | 21 | 3000 |
| XXIII | 82 ± 0 | 32 | 390 |
| XXIV | 76 ± 19 | 12 | 158 |
| XXV | 4 ± 2 | 7 | 1750 |
| XXVI | 311 ± 78 | 22 | 71 |
| XXVII | 16 ± 1 | 21 | 1313 |

TABLE 4-continued

| Compound | $EC_{50}$ (nM) | $CC_{50}$ (μM) | SI |
|---|---|---|---|
| XXVIII | 16 ± 0 | 3 | 188 |
| XXIX | 37 ± 30 | 16 | 432 |
| XXX | 19 ± 7 | 20 | 1053 |
| XXXI | 6 ± 6 | 10 | 1667 |
| XXXII | 12 ± 8 | 21 | 1750 |
| XXXIII | 1901 ± 102 | >50 | >26 |
| XXXIV | 395 ± 20 | >50 | >127 |

TABLE 5

| Compound | $EC_{50}$ (nM) | $CC_{50}$ (μM) | SI |
|---|---|---|---|
| CPD-1 | 13 ± 5 | 231 | 17769 |
| CPD-2 | 79 ± 4 | >50 | >633 |
| CPD-3 | 78 ± 5 | >50 | >641 |
| CPD-4 | 84 ± 3 | >50 | >595 |
| CPD-5 | 27 ± 27 | >50 | >1852 |
| CPD-6 | 14 ± 1 | >50 | >3571 |
| CPD-7 | 53 ± 25 | 212 | 4000 |
| CPD-8 | 79 ± 4 | >50 | >633 |
| CPD-9 | 346 ± 86 | 22 | 64 |
| CPD-10 | 80 ± 32 | 231 | 2888 |
| CPD-11 | 300 ± 100 | >50 | >167 |
| CPD-12 | 256 ± 111 | >50 | >195 |
| CPD-13 | 95 ± 22 | >50 | >526 |
| CPD-14 | 20 ± 4 | >50 | >2500 |
| CPD-15 | 86 ± 4 | >50 | >581 |
| CPD-16 | 117 ± 0 | >50 | >427 |
| CPD-17 | 72 ± 2 | 100 | 1389 |
| CPD-18 | 2 ± 1 | 20 | 10000 |
| CPD-19 | 4 ± 1 | 19 | 4750 |
| CPD-20 | 87 ± 3 | >50 | >575 |
| CPD-21 | 409 ± 0 | 31 | 76 |
| CPD-22 | 19 ± 5 | >100 | >5263 |
| CPD-23 | 84 ± 29 | >50 | >595 |
| CPD-24 | 299 ± 91 | >50 | >167 |
| CPD-25 | 78 ± 4 | >50 | >641 |
| CPD-26 | 96 ± 6 | >50 | >521 |
| CPD-27 | 366 ± 0 | >50 | >137 |
| CPD-28 | 82 ± 0 | >50 | >610 |
| CPD-29 | 257 ± 107 | >50 | >195 |
| CPD-30 | 129 ± 61 | >50 | >388 |
| CPD-31 | 306 ± 98 | >50 | >163 |
| CPD-32 | 377 ± 16 | >50 | >133 |
| CPD-33 | 447 ± 0 | >50 | >112 |
| CPD-34 | 92 ± 49 | >50 | >543 |
| CPD-35 | 75 ± 24 | >50 | >667 |
| CPD-36 | 403 ± 129 | >50 | >124 |
| CPD-37 | 370 ± 74 | >50 | >135 |
| CPD-38 | 336 ± 103 | >50 | >149 |
| CPD-39 | 84 ± 8 | >50 | >595 |
| CPD-40 | 89 ± 18 | 48 | 539 |
| CPD-41 | 223 ± 143 | >50 | >224 |
| CPD-42 | 460 ± 48 | >50 | >109 |
| CPD-43 | 81 ± 8 | >50 | >617 |
| CPD-44 | 88 ± 17 | >50 | >568 |
| CPD-45 | 297 ± 107 | >50 | >168 |
| CPD-46 | 465 ± 26 | >50 | >108 |
| CPD-47 | 341 ± 25 | 24 | 70 |
| CPD-48 | 395 ± 22 | 27 | 68 |
| CPD-49 | 409 ± 0 | 31 | 76 |

The antiviral properties of the compounds of the invention were also tested against classical swine fever virus (CSFV). Briefly, porcine kidney (PK15) cells were seeded in 96-Well plates at a density of 5000 cells/well. Following a 24-h incubation period at 37° C., cells were infected with CSFV strain Alfort 187 at 100 $TCID_{50}$ (50% tissue culture infective dose).

Plates were incubated for 1 h after which serial dilutions of the test compounds were added to the infected cell culture. Following another 48-h of incubation at 37° C., cells were fixed and read. Individual wells were scored as a percentage of positive cells in a well using the following scoring system:

0%
0-25%
25-50%
50-75%
75-100%

As validation criteria, the virus control (no test compound added) must score 100% and the cell control (no virus or test compound added) must score 0%.

Table 6 shows the results of the in vitro $EC_{50}$ values against classical swine fever virus (CSFV) for selected compounds of the invention.

TABLE 6

| Compound | $EC_{50}$ (μM) |
|---|---|
| CPD-1 | 0.3 ± 0.1 |
| CPD-7 | 1.3 ± 0.5 |
| CPD-10 | 4.3 ± 1.9 |
| CPD-29 | 2.8 ± 1.4 |
| CPD-40 | 5.9 ± 0 |

Example 19. Proof-of-Concept Efficacy and Safety Study in Calves

A first-in-calf study was performed with the Compound I

I

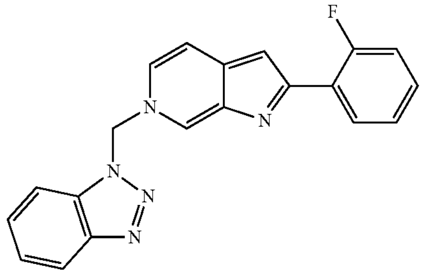

Compound I was administered at a dose rate of 2 mg/kg bodyweight three times daily at 8 h intervals. Dosing was administered for 7 consecutive days via intravenous route (10 min infusion).

A total of ten 7-month old calves (200-250 kg at study initiation) were randomly divided in two groups consisting each of five animals. All animals were healthy and free of anti-bovine viral diarrhea virus (anti-BVDV) antibodies at study initiation. One group was mock-treated and served as control group, whereas the other group was treated intravenously with Compound I according to the above treatment regimen (2 mg/kg bodyweight, 3× daily, 7 consecutive days, first dosing day denoted as Day 0). Compound I was formulated at 25 mg/mL at 30% w/v Captisol® in water for injection.

Thirty to sixty minutes after administration of the first dose on Day 0, all calves were challenged using BVDV type 1 strain SD1. Challenge was done by inoculating each animal intranasally with $10^5$ cell culture infective dose by aerosol inoculation using a DeVilbiss aerosolizer. The animals were kept for 28 days post challenge.

Animals were clinically monitored daily from Day 0 to Day 28. No signs of adverse drug reactions were observed throughout the study in any of the treated animals, indicating that Compound I was safe and very well-tolerated in calves.

Blood samples were collected on Day 0, 3, 7, 8, 9, 10, 11, 14, 21 and 28. Virus isolation was performed on resulting buffy coat for all collection time points, whereas serum samples from Day 0, 7, 14, 21 and 28 were subjected to virus neutralization testing for the presence of anti-BVDV antibodies. Haematology and clinical chemistry panels were also performed on whole blood/serum samples collected on Day 0, 7, 14, 21 and 28.

Virus isolation and virus neutralization testing were performed according to the methodology described by Newcomer et al. (Can J Vet Res. 77(3):170-6, 2013).

Haematology and clinical chemistry results (both standard assays that are performed in clinical laboratories) did not reveal any difference between both treatment groups, indicating that Compound I was safe and very well-tolerated in calves. Virus isolation results obtained from buffy coat samples (i.e., the preferred cell type for BVDV replication) are depicted in FIG. 1. During treatment with Compound I (i.e., from Day 0 to Day 6), BVDV could not be detected in buffy coat samples from Compound I treated calves, whereas virus was found in 80% of the control animals, indicating a clear antiviral effect of the compound.

Figure 2:
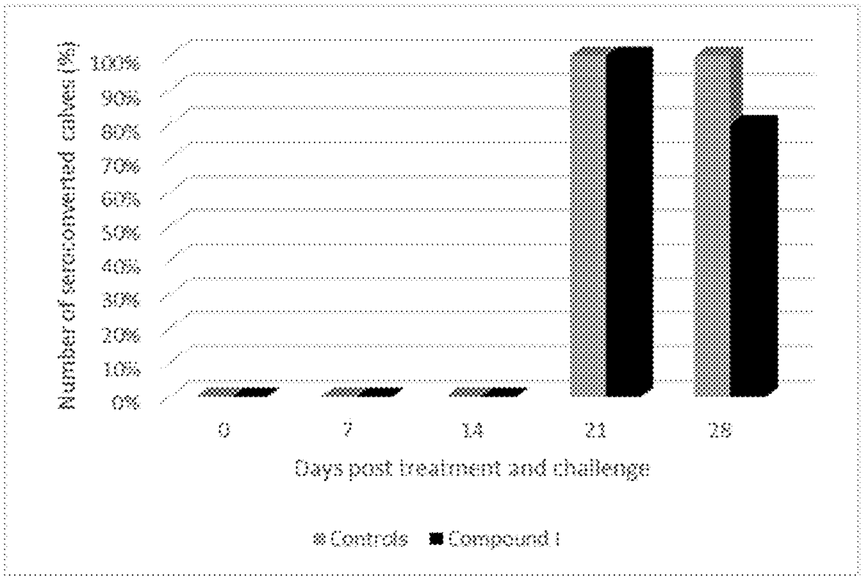
FIG. 2 represents a graph plotting the number of seroconverted calves (%) against the days post treatment with Compound I (2 mg/kg bodyweight three times daily at 8 h intervals) and untreated controls following challenge with BVDV. The compound was administered for 7 consecutive days.

The anti-BVDV antiviral effect of Compound I was further substantiated by virus neutralisation results (FIG. 2). Anti-BVDV neutralizing antibodies were first detected as of Day 14 post challenge. However, only 1 out of 5 calves treated with Compound I seroconverted by Day 14 with an antibody titre of 16 only, whereas 60% of the control animals seroconverted with antibody titres ranging between 16 and 64. Serum titres increased from Day 21 onwards with anti-BVDV neutralising antibody titres for Compound I treated calves averaging 64 on Day 28, whereas anti-BVDV neutralising antibody titres for the mock-treated calves averaged substantially higher at 205.

The results from FIGS. 1 and 2 clearly show that Compound I decreased viral load in BVDV-infected calves as compared to a control group as evidenced by the virus isolation results and substantiated by lower anti-BVDV neutralising antibody titres. Hence, Compound I is safe and effective for treatment of calves infected with BVDV.

Example 20. Proof-of-Concept Efficacy and Safety Study in Calves

A first-in-calf study was performed with the Compound CPD-7

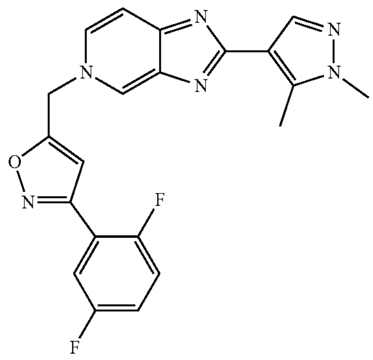 [SMILES: Cc1c(-c2nc3ccn(Cc4cc(-c5cc(F)ccc5F)no4)cc-3n2)cnn1C]

and

Compound CPD-10

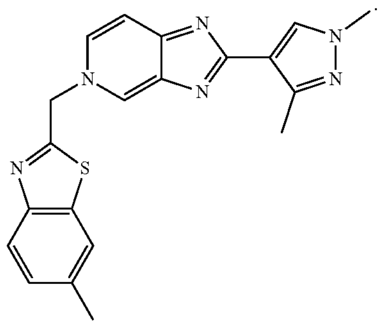 [SMILES: Cc1ccc2nc(Cn3ccc4nc(-c5cn(C)nc5C)nc-4c3)sc2c1]

Both Compound CPD-7 and Compound CPD-were administered at a dose rate of 5 mg/kg bodyweight twice daily at 12-h intervals. Dosing was administered for 10 consecutive days via intravenous route (10-min infusion).

A total of twelve 4-6-month old calves (circa 250 kg at study initiation) were randomly divided in three groups consisting of four animals each. All animals were healthy and free of anti-bovine viral diarrhea virus (anti-BVDV) antibodies at study initiation. One group was mock-treated and served as control group, whereas a second group was treated intravenously with Compound CPD-7 and a third group with Compound CPD-10 according to the above treatment regimen (5 mg/kg bodyweight, 2× daily, 10 consecutive days, first dosing day denoted as Day 0). Compound CPD-7 and Compound CPD-10 were formulated at 20 mg/mL at 30% w/v Captisol in water for injection.

Thirty to sixty minutes after administration of the first dose on Day 0, all calves were challenged with a virulent BVDV type 2 strain 1373. Challenge was done by inoculating each animal intranasally with $1.0\times10^6$/mL cell culture infective dose 50% by aerosol inoculation using a syringe-tip aerosolizer. The inoculum was split approximately evenly between the left and right nostrils. The animals were kept for 28 days post challenge.

Animals were clinically monitored daily from Day 0 to Day 28. No signs of adverse drug reactions were observed throughout the study in any of the treated animals, indicating that Compound CPD-7 and Compound CPD-10 were safe and very well-tolerated in calves.

Blood samples were collected on Day 0, 3, 6, 7, 8, 9, 10, 12, 14, 16, 21 and 28. Virus isolation was performed on resulting buffy coat and nasal swabs for all collection time points, whereas serum samples from Day 0, 7, 14, 21 and 28 were additionally subjected to virus neutralization testing for the presence of anti-BVDV antibodies. Haematology and clinical chemistry panels were also performed on whole blood/serum samples collected on Day 0, 7, 14, 21 and 28.

Virus isolation and virus neutralization testing were performed according to the methodology described by Newcomer at al. (Can J Vet Res. 77(3):170-6, 2013). Briefly, samples were assayed for the presence of BVDV by passage through, or co-cultivation with, Madin Darby bovine kidney (MDBK) cells. Samples were suspended in minimum essential medium and added to a previously-seeded layer of MDBK cells. After a one-hour adsoprtion period, additional MEM was added and the plates were incubated. Following incubation, a single freeze-thaw cycle was performed to release intracellular virus and the resulting lysate was tested in triplicate using an immunoperoxidase monolayer assay. A standard virus neutralization microtiter assay was performed to test for neutralizing antibodies to both BVDV1 (NADL) and BVDV2 (125C). Briefly, sera were heat-inactivated before making serial 2-fold dilutions for each sample, beginning at 1:2. Following incubation, the immunoperoxidase labeling was performed; the titer was expressed as the greatest dilution at which two of three wells were free of virus.

Haematology and clinical chemistry parameters (all standard assays that are performed in clinical laboratories), other than white blood cell counts (see below), were largely unremarkable. No evidence of adverse side effects of either compound, or the vehicle alone, were noted on serial complete blood cell counts or serum chemistry panels, indicating that Compound CPD-7 and Compound CPD-10 were safe and very well-tolerated in calves.

Viral challenge with BVDV type 2 strain 1373 was associated with leukopenia in this study, which is consistent with BVDV infection in general. With the exception of one calf receiving Compound CPD-7, all calves developed a leukopenia (i.e., <5000 leukocytes/μL) evident on at least one sampling day. The four untreated calves all had sustained leukopenia of at least four consecutive days' duration, primarily between Days 7-12, with the nadir for most calves seen on Days 9 and 10. One calf had a sustained leukopenia from Day 3 through Day 16. Three treated calves had a sustained leukopenia of at least three days' duration: one calf receiving Compound CPD-10 was leukopenic between Days 6 and 8; two calves receiving Compound CPD-7 were leukopenic between Days 6 and 12 with the exception of one of the two calves on Day 9. Four additional treated calves were leukopenic on a single sample day: three calves receiving Compound CPD-10 were leukopenic on Day 7 or 8 only, one calf receiving Compound CPD-7 was leukopenic on Day 10 only. Leukopenia was seen in Compound CPD-10 treated calves between Days 6-8, for Compound CPD-7 treated calves between Days 6-12, and for untreated calves from Days 3-16. The white cell count nadirs were the lowest for the untreated calves with all four calves having a white blood cell count below 3000 leukocytes/μL on at least one sampling day. Only one calf receiving Compound CPD-7 had a white cell blood count this low; one additional calf from each Compound treated group had a call count below 4000 leukocytes/μL. Hence, antiviral treatment was clearly associated with reduced duration and severity of leukopenia following BVD viral challenge.

Overall, more samples from untreated calves were virus isolation positive for BVDV (in casu 56 samples in total) than samples from calves receiving either Compound CPD-10 or Compound CPD-7 (32 and 28 samples virus isolation positive in total, respectively). Positive virus isolation samples were, in general, detected earlier and more consistently in untreated calves than in Compound treated calves. Prior to BVDV challenge, all calves were virus isolation negative for all samples on Day 0. By Day 3, three of four untreated calves were virus isolation positive on at least one sample type and all four calves were positive on at least one sample type for five consecutive sampling days beginning on Day 6. In Compound CPD-10 receiving calves, one calf was positive for the first time on Day 3, a second calf was positive for the first time on Day 6, and the remaining two calves were virus isolation positive for the first time on Day 7. Similarly, in Compound CPD-7 receiving calves, one calf was positive for the first time on Day 3 and two calves were positive for the first time on Day 6. The fourth calf in Group 2 remained 7 negative on all samples until Day 9 when virus was isolated from both serum and nasal secretions. This calf was the only calf in the study from which virus was never isolated from the buffy coat. Thus, there was a tendency toward less and delayed isolation of virus in Compound treated calves. When examining only buffy coat samples (the preferred cell type for BVDV replication) during the peak period of expected viremia (Days 6-10), 11/20 (55%) samples from Compound CPD-10 receiving calves were virus isolation positive, 10/20 (50%) samples from Compound CPD-7 receiving calves were virus isolation positive, and 16/20 (80%) samples from untreated calves were positive. The most common route of natural BVDV infection is through nasal secretions; thus, isolation of virus from nasal swabs indicates active viral shedding and increased transmission potential. A tendency toward delayed and decreased viral shedding in nasal secretions was noticed in Compound CPD-10 and Compound CPD-7 receiving calves compared to untreated calves. For all animals, most virus isolation positive nasal swabs were found by Day 12. In this period, 12/28 (43%) samples were virus isolation positive for calves receiving Compound CPD-10, 8/28 (29%) were virus isolation positive for calves receiving Compound CPD-7, and 22/28 (79%) were virus isolation positive for untreated calves, again indicating a clear antiviral effect of both Compound CPD-10 and Compound CPD-7.

Figure 3:
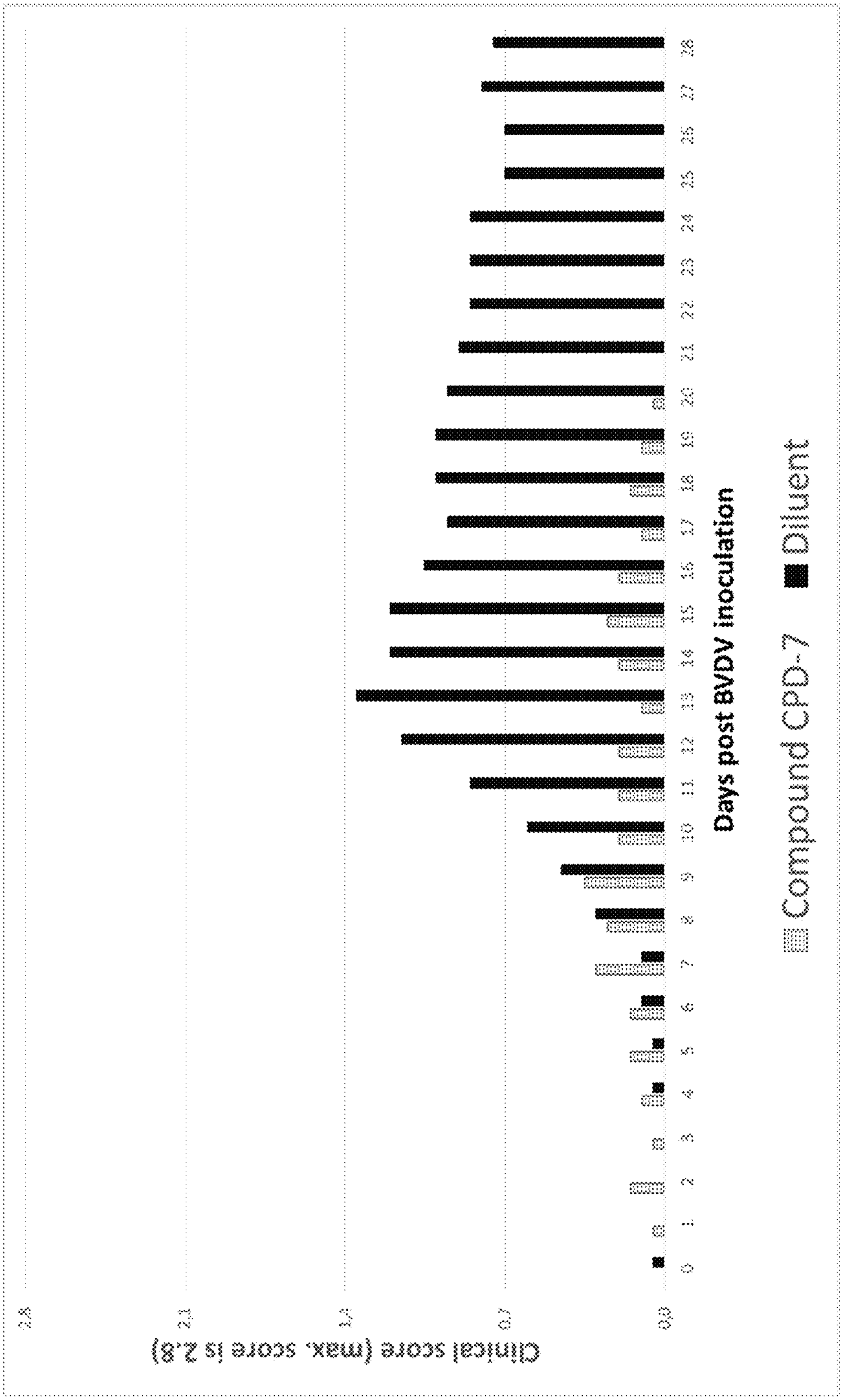
FIG. 3 represents a graph plotting the clinical score of calves post virulent BVDV challenge (the maximum clinical score is 2.8) against days post virulent BVDV challenge in calves treated with compound CPD-7 (5 mg/kg bodyweight, 2× daily, 10 consecutive days) and calves receiving diluent only.
Figure 4:
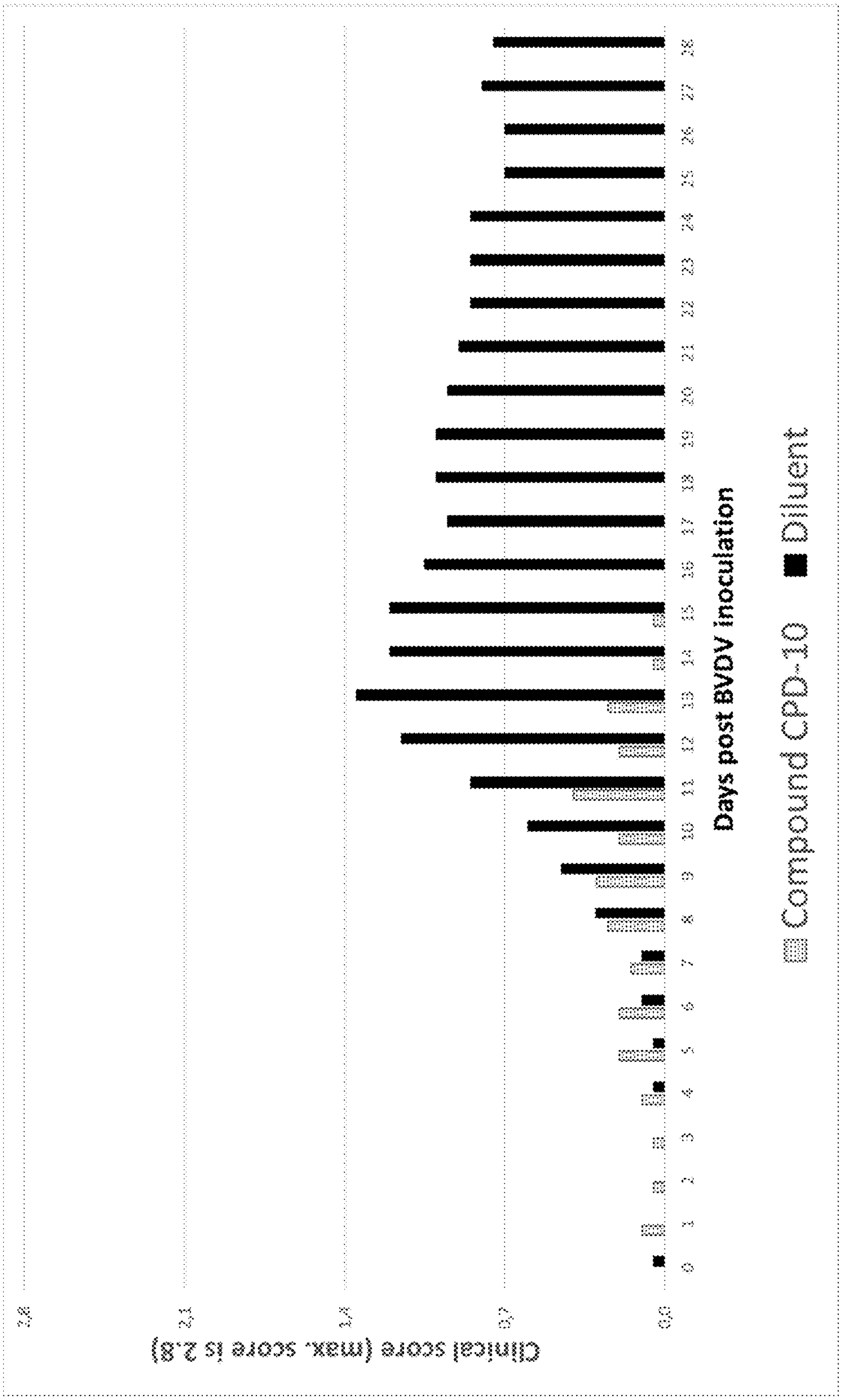
FIG. 4 represents a graph plotting the clinical score of calves post virulent BVDV challenge (the maximum clinical score is 2.8) against days post virulent BVDV challenge in calves treated with compound CPD-10 (5 mg/kg bodyweight, 2× daily, 10 consecutive days) and calves receiving diluent only.

The inoculation strain, BVDV type 2 strain 1373, was specifically chosen to test the efficacy of both Compounds against the development of clinical signs following BVDV infection as infection was expected to result in morbidity, and potentially mortality, in untreated calves. Indeed, a marked difference in clinical signs (i.e., dehydration, appearance, appetite and diarrhea) was noted between the untreated calves and those receiving Compound CPD-10 and Compound CPD-7. The daily composite clinical scores (sum of scores for dehydration, appearance, appetite and diarrhea) for the untreated calves were markedly higher than in the cohorts receiving either Compound (FIG. 3 and FIG. 4). Humane guidelines indicated that oral electrolytes were to be administered anytime dehydration score was 0.2. This was the case for three of the four untreated calves. The provision of oral electrolytes resulted in clinical improvement of two of these calves avoiding euthanasia. However, clinical improvement was not seen on the third calf, which was euthanized on Day 13. None of the Compound CPD-10 or Compound CPD-7 receiving animals showed signs of dehydration. Hence, these animals did not receive oral electrolytes nor was euthanasia a needed consideration. Furthermore, sustained (>2 consecutive days) increased appearance scores were present in all four untreated calves (100% of the animals) and in only four of eight Compound receiving calves (50% of the animals). Complete and sustained anorexia was seen in all four untreated calves whereas complete anorexia was seen in only five of eight Compound receiving calves. Sustained diarrhea was seen in all four untreated calves (100% of the animals); bloody diarrhea developed in the calf that was eventually euthanized. Neither sustained, nor bloody, diarrhea was seen in any of the Compound receiving calves.

Clinical scores for dehydration, appearance, appetite, and fecal score were recorded daily for all calves based on predefined scoring standards (see below). Scores were recorded at the time of morning feeding by the assigned attendant for that treatment period. Animal handlers were blinded to group assignment.

Scoring Standards

Dehydration Status:

0.0 Normal. Capillary refill time (CRT)<2.0 seconds.

0.2 CRT 2-3 seconds; Slight depression of eyes into the orbit; tacky mucous membranes.

1.0 CRT>3 seconds; sunken eyes, severe loss of skin elasticity (skin tent>10 seconds), cold extremities.

Appearance 0.0 Bright, alert, active.

0.2 Inactive, depressed, will move or get up with encouragement.

0.4 Inactive, depressed, increased recumbency, will move/get up with moderate encouragement.

1.0 Recumbent, severely depressed, will not move or get up even with encouragement.

Appetite 0.0 Normal, eating fine.

0.2 Decreased appetite, limited interest in eating.

0.4 Not eating.

Fecal Score 0.0 Normal.

0.2 Watery diarrhea.

0.4 Bloody feces.

In short, administration of Compound CPD-10 or Compound CPD-7 was associated with a clear antiviral effect in susceptible calves exposed to virulent BVDV challenge. Compound CPD-10 or Compound CPD-7 receiving calves had attenuated clinical scores compared to those receiving with diluent only and experienced less morbidity and mortality. Clinical signs of disease were both more prevalent and more severe in untreated calves with one calf euthanized for humane reasons and two more strongly considered as candidates for euthanasia but improved after provision of oral electrolytes. Though live virus was isolated from Compound receiving calves, it was done so less commonly and less consistently than in untreated calves. Moreover, administration of Compound CPD-10 or Compound CPD-7 was well tolerated and did not result in adverse side effects or negative haematological changes.

The invention claimed is:

1. A compound of formula (IC) or a stereoisomer, or tautomer thereof, (IC)

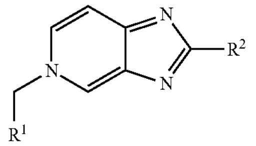

wherein, $R^1$ is selected from the group consisting of

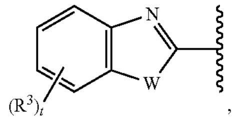

,

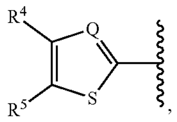

,

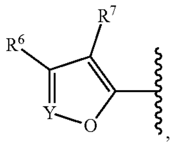

,

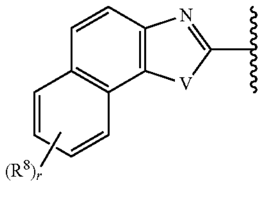

and

-continued

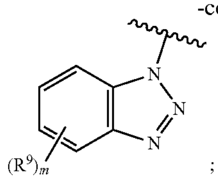

;

wherein the wavy line (  ) indicates the point of attachment to the methylene linker of the main formula (IC);

t is an integer selected from 0, 1, 2, 3 and 4;

r is an integer selected from 0, 1, 2, 3 and 4;

m is an integer selected from 0, 1, 2, 3 and 4;

W is selected from the group consisting of $NR^{10}$, S and O;

Q is selected from the group consisting of $CR^{11}$ and N;

Y is selected from the group consisting of N and $CR^{12}$;

V is selected from the group consisting of $NR^{13}$, S and O;

$R^2$ is selected from the group consisting of biphenylenyl, 1-naphthalenyl, 2-naphthalenyl, 5-tetralinyl, 6-tetralinyl, 1-azulenyl, 2-azulenyl, 3-azulenyl, 4-azulenyl, 5-azulenyl, 6-azulenyl, 7-azulenyl, 8-azulenyl, 4-indenyl, 5-indenyl, 6-indenyl, 7-indenyl, 4-indanyl, 5-indanyl, 5-tetrahydronaphthyl, 6-tetrahydronaphthyl, 7-tetrahydronaphthyl, 8-tetrahydronaphthyl, 1,2,3,4-tetrahydronaphthyl, 1,4-dihydronaphthyl, 1-pyrenyl, 2-pyrenyl, 3-pyrenyl, 4-pyrenyl, 5-pyrenyl pyrazolyl and pyridyl; wherein said biphenylenyl, 1-naphthalenyl, 2-naphthalenyl, 5-tetralinyl, 6-tetralinyl, 1-azulenyl, 2-azulenyl, 3-azulenyl, 4-azulenyl, 5-azulenyl, 6-azulenyl, 7-azulenyl, 8-azulenyl, 4-indenyl, 5-indenyl, 6-indenyl, 7-indenyl, 4-indanyl, 5-indanyl, 5-tetrahydronaphthyl, 6-tetrahydronaphthyl, 7-tetrahydronaphthyl, 8-tetrahydronaphthyl, 1,2,3,4-tetrahydronaphthyl, 1,4-dihydronaphthyl, 1-pyrenyl, 2-pyrenyl, 3-pyrenyl, 4-pyrenyl, 5-pyrenyl, pyrazolyl or pyridyl are optionally substituted with one or more $Z^1$;

each $R^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $—CH_2OH$, amino, $—N(CH_3)_2$, $—CH_2N(CH_3)_2$, $—O(CH_2)_2OH$, $—O(CH_2)_2OCH_3$, cyano, nitro and —COOH;

$R^4$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl and thiophenyl; wherein said aryl, pyrazolyl, pyridyl, or thiophenyl are optionally substituted with one or more $Z^2$;

$R^5$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl and thiophenyl; wherein said aryl, pyrazolyl, pyridyl, or thiophenyl are optionally substituted with one or more $Z^3$;

$R^6$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl and thiophenyl; wherein said aryl, pyrazolyl, pyridyl, or thiophenyl are optionally substituted with one or more $Z^4$;

$R^7$ is selected from the group consisting of hydrogen, halo, $C_{1-6}$alkyl, aryl, trifluoromethyl, difluoromethyl, $C_{1-6}$alkoxy, trifluoromethoxy, difluoromethoxy, hydroxyl, pyrazolyl, pyridyl and thiophenyl; wherein said aryl, pyrazolyl, pyridyl, or thiophenyl are optionally substituted with one or more $Z^5$;

each $R^8$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $-CH_2OH$, amino, $-N(CH_3)_2$, $-CH_2N(CH_3)_2$, $-O(CH_2)_2OH$, $-O(CH_2)_2OCH_3$, cyano, nitro and $-COOH$;

each $R^9$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $-CH_2OH$, amino, $-N(CH_3)_2$, $-CH_2N(CH_3)_2$, $-O(CH_2)_2OH$, $-O(CH_2)_2OCH_3$, cyano, nitro and $-COOH$;

$R^{10}$ is selected from the group consisting of hydrogen, $C_{1-6}$alkyl and $C_{3-8}$cycloalkyl;

$R^{11}$ is selected from the group consisting of hydrogen, $C_{1-6}$alkyl and $C_{3-8}$cycloalkyl;

$R^{12}$ is selected from the group consisting of hydrogen, $C_{1-6}$alkyl and $C_{3-8}$cycloalkyl;

$R^{13}$ is selected from the group consisting of hydrogen, $C_{1-6}$alkyl and $C_{3-8}$cycloalkyl;

each $Z^1$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $-CH_2OH$, amino, $-N(CH_3)_2$, $-CH_2N(CH_3)_2$, $-O(CH_2)_2OH$, $-O(CH_2)_2OCH_3$, cyano, nitro and $-COOH$;

each $Z^2$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $-CH_2OH$, amino, $-N(CH_3)_2$, $-CH_2N(CH_3)_2$, $-O(CH_2)_2OH$, $-O(CH_2)_2OCH_3$, cyano, nitro and $-COOH$;

each $Z^3$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $-CH_2OH$, amino, $-N(CH_3)_2$, $-CH_2N(CH_3)_2$, $-O(CH_2)_2OH$, $-O(CH_2)_2OCH_3$, cyano, nitro and $-COOH$;

each $Z^4$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $-CH_2OH$, amino, $-N(CH_3)_2$, $-CH_2N(CH_3)_2$, $-O(CH_2)_2OH$, $-O(CH_2)_2OCH_3$, cyano, nitro and $-COOH$;

each $Z^5$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $-CH_2OH$, amino, $-N(CH_3)_2$, $-CH_2N(CH_3)_2$, $-O(CH_2)_2OH$, $-O(CH_2)_2OCH_3$, cyano, nitro and $-COOH$;

or a solvate, hydrate, salt or prodrug thereof.

2. The compound according to claim 1, wherein $R^1$ is selected from the group consisting of

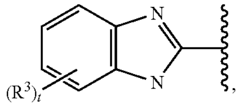

,

-continued

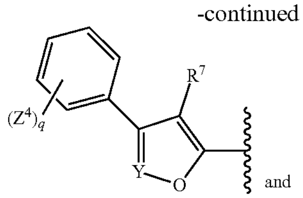

and

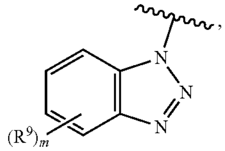

, wherein q is an integer selected from 0, 1, 2, 3, 4 and 5.

3. The compound according to claim 1, wherein W is NH, S or O.

4. The compound according to claim 1, wherein t is an integer selected from 0, 1, 2 and 3.

5. The compound according to claim 1, wherein Y is N or CH.

6. The compound according to claim 1, wherein q is an integer selected from 1, 2, 3 and 4.

7. The compound according to claim 1, wherein m is an integer selected from 0, 1, 2 and 3.

8. The compound according to claim 1, wherein $R^2$ is selected from the group consisting of biphenylenyl, 1-naphthalenyl, 2-naphthalenyl, 5-tetralinyl, 6-tetralinyl, 1-azulenyl, 2-azulenyl, 3-azulenyl, 4-azulenyl, 5-azulenyl, 6-azulenyl, 7-azulenyl, 8-azulenyl, 4-indenyl, 5-indenyl, 6-indenyl, 7-indenyl, 4-indanyl, 5-indanyl, 5-tetrahydronaphthyl, 6-tetrahydronaphthyl, 7-tetrahydronaphthyl, 8-tetrahydronaphthyl, 1,2,3,4-tetrahydronaphthyl, 1,4-dihydronaphthyl, 1-pyrenyl, 2-pyrenyl, 3-pyrenyl, 4-pyrenyl, 5-pyrenyl, pyrazolyl and pyridyl, wherein said biphenylenyl, 1-naphthalenyl, 2-naphthalenyl, 5-tetralinyl, 6-tetralinyl, 1-azulenyl, 2-azulenyl, 3-azulenyl, 4-azulenyl, 5-azulenyl, 6-azulenyl, 7-azulenyl, 8-azulenyl, 4-indenyl, 5-indenyl, 6-indenyl, 7-indenyl, 4-indanyl, 5-indanyl, 5-tetrahydronaphthyl, 6-tetrahydronaphthyl, 7-tetrahydronaphthyl, 8-tetrahydronaphthyl, 1,2,3,4-tetrahydronaphthyl, 1,4-dihydronaphthyl, 1-pyrenyl, 2-pyrenyl, 3-pyrenyl, 4-pyrenyl, 5-pyrenyl, pyrazolyl or pyridyl are optionally substituted with two or three $Z^1$.

9. The compound according to claim 1, wherein $R^2$ is pyrazolyl.

10. The compound according to claim 1, wherein each $Z^1$ is independently selected from the group consisting of halo, trifluoromethyl, difluoromethyl, $C_{1-6}$alkoxy, trifluoromethoxy, difluoromethoxy, hydroxyl, $C_{1-6}$alkyl, $-CH_2OH$, cyano, nitro and $-COOH$.

11. A pharmaceutical composition comprising one or more pharmaceutically acceptable excipients and a therapeutically effective amount of a compound according to claim 1.

* * * * *